(12) United States Patent
Shiga et al.

(10) Patent No.: US 9,732,226 B2
(45) Date of Patent: Aug. 15, 2017

(54) AZO COMPOUND, INK CONTAINING AZO COMPOUND, AND DISPLAY AND ELECTRONIC PAPER CONTAINING THE INK

(71) Applicant: MITSUBISHI CHEMICAL CORPORATION, Chiyoda-ku (JP)

(72) Inventors: Yasushi Shiga, Kanagawa (JP); Mitsuya Aoba, Kanagawa (JP); Yuki Tanaka, Kanagawa (JP); Mio Ishida, Kanagawa (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 134 days.

(21) Appl. No.: 14/610,412

(22) Filed: Jan. 30, 2015

(65) Prior Publication Data
US 2015/0191601 A1 Jul. 9, 2015

Related U.S. Application Data

(63) Continuation of application No. PCT/JP2013/070757, filed on Jul. 31, 2013.

(30) Foreign Application Priority Data

Aug. 1, 2012 (JP) .................................. 2012-171276
Nov. 28, 2012 (JP) .................................. 2012-260018

(51) Int. Cl.

| C09D 11/033 | (2014.01) |
|---|---|
| C09D 11/037 | (2014.01) |
| C09B 1/02 | (2006.01) |
| C09B 1/16 | (2006.01) |
| C09B 1/50 | (2006.01) |
| C09B 29/08 | (2006.01) |
| C09B 31/147 | (2006.01) |
| C07C 255/59 | (2006.01) |
| C07C 255/65 | (2006.01) |
| G02B 26/00 | (2006.01) |
| G02F 1/167 | (2006.01) |
| C09B 29/01 | (2006.01) |
| C09B 43/40 | (2006.01) |
| C09D 11/00 | (2014.01) |
| C07C 311/08 | (2006.01) |
| C09B 31/043 | (2006.01) |

(52) U.S. Cl.
CPC ........ *C09B 29/0003* (2013.01); *C07C 255/59* (2013.01); *C07C 255/65* (2013.01); *C07C 311/08* (2013.01); *C09B 1/02* (2013.01); *C09B 1/16* (2013.01); *C09B 1/50* (2013.01); *C09B 29/081* (2013.01); *C09B 29/0813* (2013.01); *C09B 29/0816* (2013.01); *C09B 29/0823* (2013.01); *C09B 31/043* (2013.01); *C09B 31/147* (2013.01); *C09B 43/40* (2013.01); *C09D 11/00* (2013.01); *C09D 11/033* (2013.01); *C09D 11/037* (2013.01); *G02F 1/167* (2013.01); *C07C 2101/14* (2013.01); *G02B 26/005* (2013.01); *G02F 2001/1678* (2013.01)

(58) Field of Classification Search
CPC ....... C09D 11/033; C09D 11/037; C09B 1/02; C09B 1/16; C09B 1/50; C09B 29/0003; C09B 29/081; C09B 31/147; C07C 255/59; C07C 255/65; G02B 26/005; G02F 1/167
USPC ................ 106/31.45; 534/851; 359/290, 296
See application file for complete search history.

(56) References Cited

U.S. PATENT DOCUMENTS

| 5,302,573 | A | 4/1994 | Ohyama et al. | |
|---|---|---|---|---|
| 6,866,706 | B2 * | 3/2005 | Ishida | B41M 5/345 106/31.47 |
| 8,143,382 | B2 * | 3/2012 | Shiga | C09D 11/037 106/31.5 |
| 8,747,537 | B2 * | 6/2014 | Shiga | C09D 11/037 106/31.44 |
| 8,999,050 | B2 * | 4/2015 | Ishida | C09D 11/033 106/31.44 |
| 2008/0225374 | A1 | 9/2008 | Hayes et al. | |
| 2010/0292450 | A1 | 11/2010 | Shiga et al. | |
| 2010/0296150 | A1 | 11/2010 | Hayes et al. | |
| 2013/0188238 | A1 | 7/2013 | Shiga et al. | |
| 2013/0241815 | A1 | 9/2013 | Ishida et al. | |

FOREIGN PATENT DOCUMENTS

| EP | 0534587 A2 | 3/1993 |
|---|---|---|
| JP | 61-207467 | 9/1986 |
| JP | 02-175295 | 7/1990 |
| JP | 03-7388 | 1/1991 |
| JP | 2007-531917 | 11/2007 |

(Continued)

OTHER PUBLICATIONS

English translation of the Written Opinion of the International Search Authority mailed Oct. 15, 2013 for PCT/JP2013/070757; 5 pages.*

(Continued)

*Primary Examiner* — Helene Klemanski
(74) *Attorney, Agent, or Firm* — Oblon, McClelland, Maier & Neustadt, L.L.P.

(57) ABSTRACT

An azo compound excellent in solubility in solvent and having a high absorbance coefficient is disclosed, as well as an ink containing the azo compound. Such an ink contains a solvent having a relative permittivity at 22° C. and at a measurement frequency of 1 kHz of 3 or less and having a solubility in water at 25° C. of 20 mg/L or less, and an azo compound.

15 Claims, No Drawings

(56) References Cited

FOREIGN PATENT DOCUMENTS

| JP | 2009-138189 | 6/2009 |
|----|---|---|
| WO | 2009/063880 | 5/2009 |
| WO | 2011/111710 | 9/2011 |
| WO | WO 2012/019704 A1 | 2/2012 |
| WO | 2012/033177 | 3/2012 |
| WO | WO 2013/170935 A1 | 11/2013 |
| WO | 2014/021384 | 2/2014 |

OTHER PUBLICATIONS

English translation of JP 03/007388; Jan. 1991; 7 pages.*
International Search Report issued Oct. 15, 2013 in PCT/JP2013/070757 filed Jul. 31, 2013 with English Translation.
"Nature" (Britain), 2003, vol. 425, pp. 383-385.
Combined Chinese Office Action and Search Report issued Dec. 16, 2015 in Patent Application No. 201380040313.3 (with English language machine translation and English translation of categories of cited documents).
Japanese Office Action issued Sep. 20, 2016 in Patent Application No. 2014-528196 (with English Translation).

* cited by examiner

AZO COMPOUND, INK CONTAINING AZO COMPOUND, AND DISPLAY AND ELECTRONIC PAPER CONTAINING THE INK

CROSS-REFERENCE TO RELATED APPLICATIONS

This application is a Continuation of PCT/JP2013/070575 filed on Jul. 31, 2013. This application is based upon and claims the benefit of priority to Japanese Application No. 2012-171276 filed on Aug. 1, 2012, and to Japanese Application No. 2012-260018 filed on Nov. 28, 2012, the entire contents of both of which are incorporated herein by reference.

TECHNICAL FIELD

The present invention relates to an azo compound and to an ink containing the compound, and more precisely relates to an azo compound having a specific chemical structure and an ink containing the compound and useful for displays or for optical shutters.

BACKGROUND ART

An electrowetting display is an image display system where multiple pixels each filled with two phases of an aqueous medium and an oily color ink are arranged on a substrate, and the interface affinity of aqueous medium/oily color ink is controlled for each pixel by on-off voltage application to those pixels to thereby develop/aggregate the oily color ink on the substrate for image display (NPL 1). The colorant for use in electrowetting displays is required to have a high solubility in low-polar solvents and a high molar absorbance coefficient (PTL 1, PTL 2).

PTL 3 describes use of monoazo compounds similar to those of the present invention as dyes for polyester fibers.

CITATION LIST

Patent Literature

PTL 1: JP-T 2007-531917
PTL 2: WO2009/063880
PTL 3: JP-A 61-207467

Non-Patent Literature

NPL 1: "Nature" (Britain), 2003, Vol. 425, pp. 383-385

SUMMARY OF INVENTION

Technical Problem

However, PTL 3 neither describes nor suggests the solubility of the dyes in solvents, especially the solubility thereof in low-polar solvents.

Objectives of the present invention are to provide a compound having an excellent solubility in low-polar solvents and having a high absorbance coefficient and to provide an ink using the compound.

Solution to Problem

The present inventors have assiduously studied for the purpose of solving the above-mentioned problems and, as a result, have found that an azo compound having a certain chemical structure is excellent in solubility in solvents and has a high molar absorbance coefficient. The present invention has been achieved on the basis of these findings.

Specifically, the gist of the present invention includes the following [1] to [14].

[1] An ink comprising: a solvent having a relative permittivity at 22° C. and at a measurement frequency of 1 kHz of 3 or less and having a solubility in water at 25° C. of 20 mg/L or less; and an azo compound represented by the following general formula (1):

[Chem. 1]

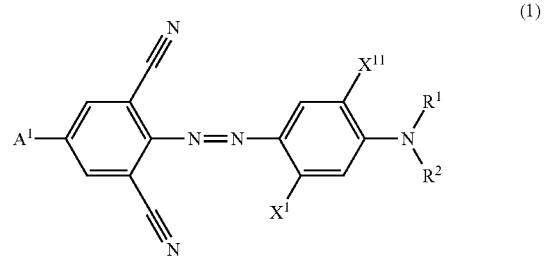

(1)

[In the general formula (1), $R^1$ and $R^2$ each independently represent a hydrocarbon group optionally having a substituent; $X^1$, $X^{11}$ and $A^1$ each independently represent a hydrogen atom or an arbitrary substituent.]

[2] The ink according to the [1] above, wherein the solvent contains at least one solvent selected from a group consisting of a hydrocarbon solvent, a silicone oil and a fluorocarbon solvent.

[3] The ink according to the [1] to [2] above, wherein a product $\epsilon C$ of a molar absorbance coefficient $\epsilon\Sigma(L \cdot mol^{-1} \cdot cm^{-1})$ at absorption maximum wavelength of an n-decane solution of the azo compound, and a saturation solubility C ($mol \cdot L^{-1}$) of the solution at 5° C., is 1000 cm' or more.

[4] The ink according to any one of the [1] to [3] above, further comprising at least one compound selected from a group consisting of a heterocyclic compound, a cyanovinyl compound and an anthraquinone compound.

[5] The ink according to the [4] above, wherein the heterocyclic compound is at least one compound selected from a group consisting of the following general formulae (2) to (5):

[Chem. 2]

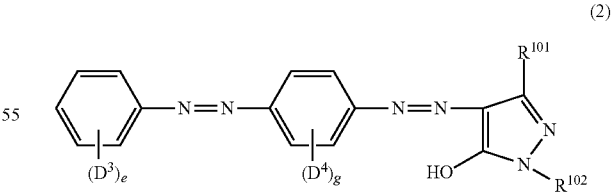

(2)

[In the general formula (2), $R^{101}$ and $R^{102}$ each independently represent a hydrogen atom or an arbitrary substituent; $D^3$ and $D^4$ each independently represent an arbitrary substituent, e indicates an integer of from 0 to 5, and when e is 2 or more, 2 or more $D^3$s existing in one molecule may be the same or different; g indicates an integer of from 0 to 4, and when g is 2 or more, 2 or more $D^4$s existing in one molecule may be the same or different.]

[Chem. 3]

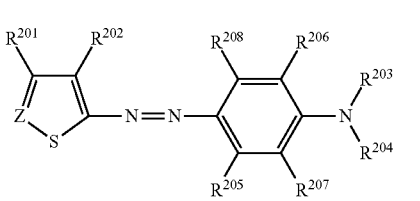

(3)

[In the general formula (3), $R^{201}$ to $R^{208}$ each independently represent a hydrogen atom or an arbitrary substituent; Z represents a nitrogen atom or a methine group optionally having a substituent.]

[Chem. 4]

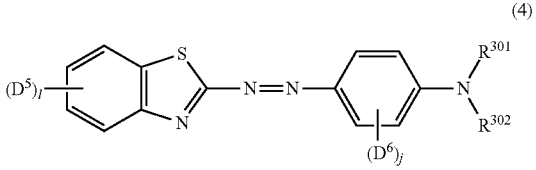

(4)

[In the general formula (4), $R^{301}$, $R^{302}$, $D^5$ and $D^6$ each independently represent an arbitrary substituent; l indicates an integer of from 0 to 4, and when l is 2 or more, 2 or more $D^5$s existing in one molecule may be the same or different; j indicates an integer of from 0 to 4, and when j is 2 or more, 2 or more $D^6$s existing in one molecule may be the same or different.]

[Chem. 5]

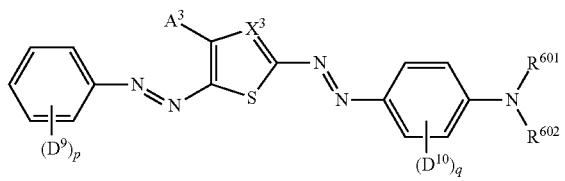

(5)

[In the general formula (5), $R^{601}$, $R^{602}$, $D^9$ and $D^{10}$ each independently represent an arbitrary substituent; $A^3$ represents a hydrogen atom or an arbitrary substituent; p indicates an integer of from 0 to 5, and when p is 2 or more, 2 or more $D^9$s existing in one molecule may be the same or different; q indicates an integer of from 0 to 4, and when q is 2 or more, 2 or more $D^{10}$s existing in one molecule may be the same or different; $X^3$ represents a nitrogen atom, or a methine group having a halogen atom, a cyano group or a group —COOR$^{605}$ as a substituent; $R^{605}$ represents a hydrogen atom, an alkyl group having a carbon number of from 1 to 20 and optionally having a substituent, an aryl group having a carbon number of from 6 to 20 and optionally having a substituent, or a heteroaryl group having a carbon number of from 2 to 20 and optionally having a substituent.]

[6] The ink according to the [4] or [5] above, wherein the anthraquinone compound is represented by the following general formula (7):

[Chem. 6]

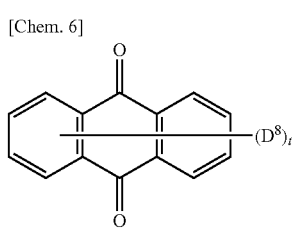

(7)

[In the general formula (7), $D^8$ represents an arbitrary substituent; t indicates an integer of from 0 to 8, and when t is 2 or more, 2 or more $D^8$s existing in one molecule may be the same or different.]

[7] An ink comprising: a solvent having a relative permittivity at 22° C. and at a measurement frequency of 1 kHz of 3 or less and having a solubility in water at 25° C. of 25 mg/L or less; and at least one of each of the following compounds (I) to compounds (IV):

(I) A compound of which an n-decane solution has an absorption maximum wavelength of from 400 nm to less than 500 nm, (II) A compound of which an n-decane solution has an absorption maximum wavelength of from 500 nm to less than 570 nm, (III) A compound of which an n-decane solution has an absorption maximum wavelength of from 570 nm to less than 630 nm, (IV) A compound of which an n-decane solution has an absorption maximum wavelength of from 640 nm to 700 nm.

[8] An ink according to any one of the [1] to [7] above, which is for displays or optical shutters.

[9] A display which has a display area containing the ink according to any one of the [1] to [7] above, and which displays an image by controlling a voltage application to the display area.

[10] The display according to the [9] above, wherein the display area contains at least either one of electrophoretic particles and an aqueous medium.

[11] The display according to the [9] or [10] above, which displays an image by changing the coloration state through control of voltage application.

[12] The display according to any one of the [9] to [11] above, which displays an image according to an electrowetting system or an electrophoretic system.

[13] An electronic paper having the display of any one of the [9] to [12] above.

[14] An azo compound represented by the following general formula (8):

[Chem. 7]

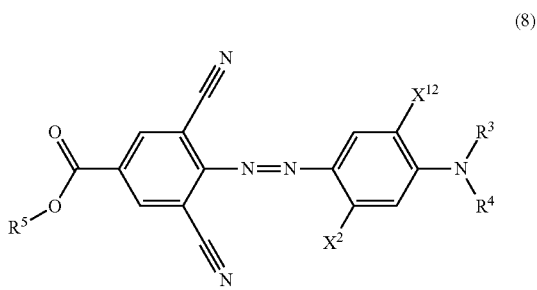

(8)

[In the general formula (8), $R^3$ and $R^4$ each independently represent an alkyl group having a carbon number of from 1 to 20 and optionally having a substituent; $R^5$ represents an alkyl group having a branched chain and having a carbon number of from 4 to 20 and optionally having a substituent; $X^2$ and $X^{12}$ each independently represent a hydrogen atom or an arbitrary substituent.]

Advantageous Effects of Invention

The ink containing the azo compound of the present invention has a high solubility especially in low-polar solvents and has a high molar absorbance coefficient, and is therefore useful especially for displays and optical shutters.

Further, as displays, the present invention is especially useful as a display which has a display area containing an ink and which displays an image by controlling the voltage application to the display area, a display which displays an image by changing the coloration state through voltage application, and an display which displays an image using at least either one of electrophoretic particles and an aqueous medium in the display area thereof.

Here, the electrophoretic particles are electrically-charged particles which may be colored, and the display area may contain different types of electrophoretic particles. The aqueous medium is a fluid that may be colored, and the display area may contain different types of aqueous media.

The azo compound and the ink of the present invention are especially useful as an ink for use for electrowetting-mode displays or for electrophoresis-mode displays.

Comprising an azo compound of the present invention as combined with any other compound, the ink of the present invention can provide different colors of inks including a good black ink having an excellent hue, and the ink is useful also as a member capable of functioning as an optical shutter.

The present invention is applicable to any type of display devices having an image display function, but is especially useful for electronic papers.

DESCRIPTION OF EMBODIMENTS

Typical embodiments for carrying out the present invention are described concretely hereinunder. Not overstepping the sum and substance thereof, the present invention is not limited to the following embodiments, and may be carried out as various modifications. Here, "% by weight" and "% by mass" are the same.

The ink of the present invention is an ink containing a solvent that has a relative permittivity at 22° C. and at a measurement frequency of 1 kHz of 3 or less and has a solubility in water at 25° C. of 20 mg/L or less, and an azo compound represented by the following general formula (1):

[Chem. 8]

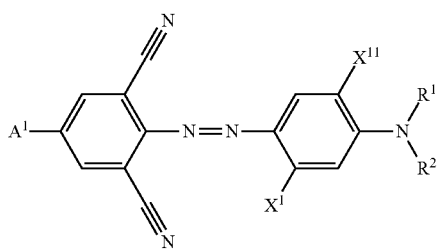

(1)

[In the general formula (1), $R^1$ and $R^2$ each independently represent a hydrocarbon group optionally having a substituent; $X^1$, $X^{11}$ and $A^1$ each independently represent a hydrogen atom or an arbitrary substituent.]

(Solvent)

The display and the optical shutter of the present invention use a low-polar solvent as the solvent for the ink therein. The ink of the present invention has a layer of, for example, an aqueous layer, an oily layer and the like, and can be used in display devices based on layer break up or layer moving aside. For making sharp images, it is necessary that the oily layer contained in the ink does not mix with the aqueous layer therein and can stably break up or move aside, and the solvent in the ink is required to be poorly miscible with water and has low polarity. In the present invention, the ink contains a specific solvent and a specific azo compound, in which the oily layer can stably break up or move aside.

In a display device based on electrophoresis in which electrically-charged particles (electrophoretic particles) move aside owing to the electric filed given thereto in a solvent, a large permittivity of the solution may interfere with device operation. Using the specific solvent and the specific azo compound in the present invention, the solution can be colored not interfering with the action of the particles to move aside.

The solvent for use in the present invention has a relative permittivity, as measured at a frequency of 1 kHz and at 22° C., of 3 or less. Preferably, the relative permittivity is 2.5 or less, more preferably 2.2 or less. The lower limit of the relative permittivity is not specifically defined, but is generally 1.5 or more, preferably 1.8 or more. The measurement method for the relative permittivity of solvent is shown in the section of Examples. In case where multiple solvents are mixed and used for ink, the above-mentioned relative permittivity indicates the relative permittivity of the mixed solvent.

When the relative permittivity of the layer containing the ink falls within a suitable range, the display device using the ink could be driven with no trouble. For example, in case where the other layer not containing the ink is an electro-conductive or polar liquid such as water, a salt solution or the like and when the relative permittivity of the solvent used in the ink-containing layer falls within a suitable range, then the layers could be prevented from mixing.

The solvent for use in the present invention has a solubility in water at 25° C. of 20 mg/L or less, preferably 10 mg/L or less, more preferably 5 mg/L or less. The method for measuring the solubility in water of the solvent is shown in the section of examples. In case where multiple solvents are mixed and used as the solvent for the ink, the solubility in water mentioned above indicates the solubility of the mixed solvent.

Having a low solubility in water, for example, the oily layer does not mix with the aqueous layer, and therefore the display device can be driven with no trouble.

Not specifically defined, the boiling point of the solvent in the present invention is preferably 120° C. or higher, more preferably 150° C. or higher, even more preferably 170° C. or higher. Also preferably, the boiling point is 300° C. or lower. The solvent does not have a too high boiling point, and therefore, the melting point and the viscosity of the solvent could not be too high, and the display device tends to be driven stably. The boiling point of the solvent is not too low, and therefore the solvent would hardly evaporate away and could therefore secure stability and safety.

Not specifically defined, the viscosity of the solvent for use in the present invention is preferably 0.1 mPa·s or more at 25° C. The viscosity is also preferably 10000 mPa·s or less, more preferably 1000 mPa·s or less, even more preferably 100 mPa·s or less. The viscosity of the solvent is not too large, and therefore compounds and others could readily dissolve therein and the display device tends to be stably driven.

The solvent may be used singly or as a mixture of multiple solvents. Specific examples of the solvent include hydrocarbon solvents, fluorocarbon solvents, silicone oils, etc.

The hydrocarbon solvents include linear or branched aliphatic hydrocarbons, alicyclic hydrocarbons, aromatic hydrocarbons, petroleum naphtha, etc.

The aliphatic hydrocarbon solvent and the alicyclic hydrocarbon solvent include, for example, aliphatic hydrocarbon solvents such as n-decane, isodecane, decalin, nonane, dodecane, isododecane, tetradecane, hexadecane, isoalkanes, etc. As commercial products of the solvents, there are mentioned Isopar E, Isopar G, Isopar H, Isopar L, Isopar M (registered trademarks, by Exxon Mobile), IP Solvent (registered trademark, by Idemitsu Petrochemical), Solutol (by Phillips Petroleum), etc.

The aromatic hydrocarbon solvent includes alkylnaphthalenes, tetralin, etc.

The petroleum naphtha solvent includes Shell S.B.R., Shellsol 70, Shellsol 71 (by Shell Petrochemical), Pegasol (by Exxon Mobile), Hisosol (by Nippon Oil), etc.

The fluorocarbon solvent is mainly a fluorine-substituted hydrocarbon and includes, for example, perfluoroalkanes represented by $C_nF_{2n+2}$, such as $C_7F_{16}$, $C_8F_{18}$, etc. Commercial products of the solvent include Florinate PF5080, Florinate PF5070 (by Sumitomo 3M), etc.

As fluorine-containing inert liquids, there are mentioned Florinate FC Series (by Sumitomo 3M), etc.; as fluorocarbons, there are mentioned Crytox GPL Series (registered trademark, by DuPont Japan Limited); as chlorofluorocarbons, there are mentioned HCFC-141b (by Daikin), as iodofluorocarbons such as $F(CF_2)_4CH_2CH_2I$, $F(CF_2)_6I$ and the like, there are mentioned I-1420, I-1600 (by Daikin Fine Chemical Laboratories), etc.

As silicone oil, for example, there are mentioned synthetic dimethylpolysiloxane having a low viscosity, and as commercial product, there are mentioned KF96L (by Shin-etsu Silicone), SH200 (by Toray Dow Corning Silicone), etc.

Preferably, the solvent contains at least one selected from a group consisting of hydrocarbon solvents, fluorocarbon solvents and silicone oils. The content of these solvents is generally 50% by mass or more of the solvent, preferably 70% by mass or more, more preferably 90% by mass or more.

In case where solvents are mixed and used here and in case where the interaction between the solvents is small as in the present invention, the relative permittivity of the mixed solvent can be approximated to the value to be calculated by multiplying the relative permittivity of each solvent constituting the mixed solvent by the volume fraction of each solvent followed by summing up the resultant values. Similarly, in case where the interaction between the solvents is small, the solubility in water of the mixed solvent can be approximated to the value to be calculated by multiplying the solubility in water of each solvent constituting the mixed solvent by the molar fraction of each solvent followed by summing up the resultant values.

The ink of the present invention contains a specific solvent and a specific azo compound, and can be prepared by dissolving the azo compound and any other optional compound or additive or the like, in a solvent.

Here, dissolution does not always mean that the azo compound is completely dissolved in a solvent, but may be such that the azo compound can pass through a filter having a pore size of 0.1 μm or so and the absorbance coefficient thereof can be measured, or that is, the state of dissolution here includes a case where fine particles of the compound are kept dispersed.

(Azo Compound)

The azo compound for use in the ink of the present invention has a chemical structure represented by the above-mentioned general formula (1).

Specific examples of $R^1$, $R^2$, $A^1$, $X^1$ and $X^{11}$ in the general formula (1) are described below.

$R^1$ and $R^2$ each independently represent a hydrocarbon group optionally having a substituent. The hydrocarbon group includes a saturated hydrocarbon group; and an unsaturated hydrocarbon group such as an acyclic unsaturated hydrocarbon group, an alicyclic hydrocarbon group, an aromatic hydrocarbon group, etc. These may be linear or branched.

The saturated hydrocarbon group includes an alkyl group, a cycloalkyl group, etc. The acyclic unsaturated hydrocarbon group includes an alkenyl group, an alkynyl group, etc.; the alicyclic hydrocarbon group includes a cycloalkenyl group, etc.; and the aromatic hydrocarbon group includes a phenyl group, etc.

Of those, preferred is the saturated hydrocarbon group from the viewpoint of the solubility thereof. Above all, preferred is an alkyl group. Of the alkyl group, especially preferred is an alkyl group having from 1 to 20 carbon atoms from the viewpoint of the solubility thereof.

Examples of the alkyl group having from 1 to 20 carbon atoms include alkyl groups optionally having a branched chain and a cyclic structure, such as a methyl group, an ethyl group, a propyl group, an isopropyl group, a cyclopropyl group, a butyl group, an isobutyl group, a sec-butyl group, a tert-butyl group, a pentyl group, a cyclopentyl group, a hexyl group, a cyclohexyl group, a heptyl group, an octyl group, a 2-ethylhexyl group, a decyl group, a dodecyl group, etc.

The alkyl group may have any arbitrary substituent. Examples of the substituent include a halogen atom such as a fluorine atom, a chlorine atom, a bromine atom, an iodine atom, etc.; an alkoxy group having from 1 to 20 carbon atoms and optionally having a branched chain and a cyclic structure, such as a methoxy group, an ethoxy group, a propoxy group, an isopropoxy group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc.; an alkoxycarbonyl group having from 2 to 21 carbon atoms and optionally having a branched chain and a cyclic structure, such as a methoxycarbonyl group, an ethoxycarbonyl group, a propoxycarbonyl group, an isopropoxycarbonyl group, a cyclopropoxycarbonyl group, a butoxycarbonyl group, an isobutoxycarbonyl group, a sec-butoxycarbonyl group, a tert-butoxycarbonyl group, a pentyloxycarbonyl group, a cyclopentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a decyloxycarbonyl group, a dodecyloxycarbonyl group, etc.; an acyloxy group having from 1 to 20 carbon atoms and optionally having a branched chain and a cyclic structure, such as a formyloxy group, an acetyloxy group, a propionyloxy group, a butyryloxy group, an isobutyryloxy group, a cyclopropylcarbonyloxy group, a valeryloxy group, an isovaleryloxy group, a pivaloyloxy group, a hexanoyloxy group, a cyclopentylcarbonyloxy group, a heptanoyloxy group, a cyclohexylcarbonyloxy group, an octanoyloxy group, a 2-ethylhexanoyloxy group, a decanoyloxy group, a dodecanoyloxy group, etc.; an aryl group such as a phenyl group, a naphthyl group, etc.; a cyano group, etc.

Of the alkyl group having from 1 to 20 carbon atoms and optionally having a substituent for $R^1$ and $R^2$, preferred is one having 2 or more carbon atoms, more preferred is one having 4 or more carbon atoms, and even more preferred is one having 6 or more carbon atoms. Also preferred is one having 20 or less carbon atoms, more preferred is one having 16 or less carbon atoms, and even more preferred is one having 12 or less carbon atoms. Having a carbon number that falls within the preferred range, the azo compound tends to have a high solubility in solvent and have a high gram absorbance coefficient.

As the alkyl group having from 1 to 20 carbon atoms and optionally having a substituent for $R^1$ and $R^2$, it is desirable that at least one is a branched alkyl group, and more preferably the two are branched alkyl groups. When $R^1$ and $R^2$ each are a branched alkyl group, the azo compound can attain a high solubility.

$A^1$ represents a hydrogen atom or an arbitrary substituent. Not specifically defined, the arbitrary substituent may be any known substituent usable in azo compounds.

The arbitrary substituent for $A^1$ is not specifically defined, but for high solubility in solvent and a high absorbance coefficient, the substituent concretely includes a halogen atom such as a fluorine atom, a chlorine atom, a bromine atom, an iodine atom, etc.; an alkyl group having from 1 to 20 carbon atoms and optionally having a branched chain and a cyclic structure such as a methyl group, an ethyl group, a propyl group, an isopropyl group, a cyclopropyl group, a butyl group, an isobutyl group, a sec-butyl group, a tert-butyl group, a pentyl group, a cyclopentyl group, a hexyl group, a cyclohexyl group, a heptyl group, an octyl group, a 2-ethylhexyl group, a decyl group, a dodecyl group, etc.; an alkoxy group having from 1 to 20 carbon atoms and optionally having a branched chain and a cyclic structure, such as a methoxy group, an ethoxy group, a propoxy group, an isopropoxy group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc.; an alkoxycarbonyl group having from 2 to 21 carbon atoms and optionally having a branched chain and a cyclic structure, such as a methoxycarbonyl group, an ethoxycarbonyl group, a propoxycarbonyl group, an isopropoxycarbonyl group, a cyclopropoxycarbonyl group, a butoxycarbonyl group, an isobutoxycarbonyl group, a sec-butoxycarbonyl group, a tert-butoxycarbonyl group, a pentyloxycarbonyl group, a cyclopentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a decyloxycarbonyl group, a dodecyloxycarbonyl group, etc.; an acyl group having from 1 to 20 carbon atoms and optionally having a branched chain and a cyclic structure, such as a formyl group, an acetyl group, a propionyl group, a butyryl group, an isobutyl group, a cyclopropylcarbonyl group, a valeryl group, an isovaleryl group, a pivaloyl group, a hexanoyl group, a cyclopentylcarbonyl group, a heptanoyl group, a cyclohexylcarbonyl group, an octanoyl group, a 2-ethylhexanoyl group, a decanoyl group, a dodecanoyl group, etc.; an aryl group such as a phenyl group, a 1-naphthyl group, a 2-naphthyl group, etc.; a nitro group; a cyano group, etc.

Of those, from the viewpoint of solubility and producibility, preferred is an alkyl group having from 1 to 20 carbon atoms or an alkoxycarbonyl group having from 2 to 21 carbon atoms.

Of the alkyl group having from 1 to 20 carbon atoms, preferred from the viewpoint of solubility is one having 10 or less carbon atoms, and more preferred is one having 8 or less carbon atoms.

Of the alkoxycarbonyl group having from 2 to 21 carbon atoms, preferred from the viewpoint of solubility is one having 3 or more carbon atoms, more preferred is one having 5 or more carbon atoms, and also preferred is one having 11 or less carbon atoms. Concretely, there is mentioned an alkoxycarbonyl group having a branched chain, such as an isobutoxycarbonyl group, a sec-butoxycarbonyl group, a tert-butoxycarbonyl group, a 2-ethylhexyloxycarbonyl group, etc.

In case where $A^1$ is an alkyl group having from 1 to 20 carbon atoms, an alkoxy group having from 1 to 20 carbon atoms, an alkoxycarbonyl group having from 2 to 21 carbon atoms, an acyl group having from 1 to 20 carbon atoms, or an aryl group, these groups may further have any arbitrary substituent.

Examples of the arbitrary substituent include a halogen atom such as a fluorine atom, a chlorine atom, a bromine atom, an iodine atom, etc.; an alkyl group having from 1 to 20 carbon atoms and optionally having a branched chain and a cyclic structure such as a methyl group, an ethyl group, a propyl group, an isopropyl group, a cyclopropyl group, a butyl group, an isobutyl group, a sec-butyl group, a tert-butyl group, a pentyl group, a cyclopentyl group, a hexyl group, a cyclohexyl group, a heptyl group, an octyl group, a 2-ethylhexyl group, a decyl group, a dodecyl group, etc.; an alkoxy group having from 1 to 20 carbon atoms and optionally having a branched chain and a cyclic structure, such as a methoxy group, an ethoxy group, a propoxy group, an isopropoxy group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc.; an alkoxycarbonyl group having from 2 to 21 carbon atoms and optionally having a branched chain and a cyclic structure, such as a methoxycarbonyl group, an ethoxycarbonyl group, a propoxycarbonyl group, an isopropoxycarbonyl group, a cyclopropoxycarbonyl group, a butoxycarbonyl group, an isobutoxycarbonyl group, a sec-butoxycarbonyl group, a tert-butoxycarbonyl group, a pentyloxycarbonyl group, a cyclopentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a decyloxycarbonyl group, a dodecyloxycarbonyl group, etc.; an acyloxy group having from 1 to 20 carbon atoms and optionally having a branched chain and a cyclic structure, such as a formyloxy group, an acetyloxy group, a propionyloxy group, a butyryloxy group, an isobutyloxy group, a cyclopropylcarbonyloxy group, a valeryloxy group, an isovaleryloxy group, a pivaloyloxy group, a hexanoyloxy group, a cyclopentylcarbonyloxy group, a heptanoyloxy group, a cyclohexylcarbonyloxy group, an octanoyloxy group, a 2-ethylhexanoyloxy group, a decanoyloxy group, a dodecanoyloxy group, etc.; an aryl group such as a phenyl group, a naphthyl group, etc.; a cyano group, etc.

Of the substituents which the alkyl group having from 1 to 20 carbon atoms, the alkoxy group having from 1 to 20 carbon atoms, the alkoxycarbonyl group having from 2 to 21 carbon atoms, the acyl group having from 1 to 20 carbon atoms or the aryl group for $A^1$ may have, preferred from the viewpoint of solubility are a halogen atom and an alkoxy group having from 1 to 20 carbon atoms and optionally having a branched chain and a cyclic structure. Of those, the halogen atom is especially preferably a fluorine atom, and the alkoxy group having from 1 to 20 carbon atoms and optionally having a branched chain and a cyclic structure is one having from 1 to 8 carbon atoms.

In case where $A^1$ is an alkyl group having from 1 to 20 carbon atoms, the substituent that the alkyl group having from 1 to 20 carbon atoms may have is preferably a halogen atom or an alkoxy group from the viewpoint of solubility and producibility, more preferably a halogen atom, even more preferably a fluorine atom. Of those, from the viewpoint of solubility, more especially preferred is a perfluoroalkyl group such as a nonafluorobutyl group, a pentafluoroethyl group, a trifluoromethyl group, etc.

In case where $A^1$ is an alkoxycarbonyl group having from 2 to 21 carbon atoms, the substituent that the alkoxycarbonyl group having from 2 to 21 carbon atoms may have is preferably a halogen atom or an alkoxy group from the viewpoint of solubility and producibility.

$X^1$ represents a hydrogen atom or an arbitrary substituent. Not specifically defined, the arbitrary substituent may be any known substituent usable in the coupler moiety in azo compounds. For securing high solubility in solvent and a high absorbance coefficient, the substituent concretely includes a halogen atom such as a fluorine atom, a chlorine atom, a bromine atom, an iodine atom, etc.; an alkyl group having from 1 to 20 carbon atoms and optionally having a branched chain and a cyclic structure such as a methyl group, an ethyl group, a propyl group, an isopropyl group, a cyclopropyl group, a butyl group, an isobutyl group, a sec-butyl group, a tert-butyl group, a pentyl group, a cyclopentyl group, a hexyl group, a cyclohexyl group, a heptyl group, an octyl group, a 2-ethylhexyl group, a decyl group, a dodecyl group, etc.; an alkoxy group having from 1 to 20 carbon atoms and optionally having a branched chain and a cyclic structure, such as a methoxy group, an ethoxy group, a propoxy group, an isopropoxyl group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc.; an acylamino group having from 1 to 20 carbon atoms and optionally having a branched chain and a cyclic structure, such as a formylamino group, an acetylamino group, a propionylamino group, a butyrylamino group, an isobutylamino group, a cyclopropylcarbonylamino group, a valerylamino group, an isovalerylamino group, a pivalyolamino group, a hexanoylamino group, a cyclopentylcarbonylamino group, a heptanoylamino group, a cyclohexylcarbonylamino group, an octanoylamino group, a 2-ethylhexnanoylamino group, a decanoylamino group, a dodecanoylamino group, etc.; an alkoxycarbonylamino group having from 2 to 21 carbon atoms and optionally having a branched chain and a cyclic structure, such as a methoxycarbonylamino group, an ethoxycarbonylamino group, a propoxycarbonylamino group, an isopropoxycarbonylamino group, a cyclopropoxycarbonylamino group, a butoxycarbonylamino group, an isobutoxycarbonylamino group, a sec-butoxycarbonylamino group, a tert-butoxycarbonylamino group, a pentyloxycarbonylamino group, a cyclopentyloxycarbonylamino group, a hexyloxycarbonylamino group, a cyclohexyloxycarbonylamino group, a heptyloxycarbonyl group, an octyloxycarbonylamino group, a 2-ethylhexyloxycarbonylamino group, a decyloxycarbonylamino group, a dodecyloxycarbonylamino group, etc.; an alkylsulfonylamino group having from 1 to 20 carbon atoms and optionally having a branched chain and a cyclic structure, such as a methylsulfonylamino group, an ethylsulfonylamino group, a propylsulfonylamino group, an isopropylsulfonylamino group, a cyclopropylsulfonylamino group, a butylsulfonylamino group, an isobutylsulfonylamino group, a sec-butylsulfonylamino group, a tert-butylsulfonylamino group, a pentylsulfonylamino group, a cyclopentylsulfonylamino group, a hexylsulfonylamino group, a cyclohexylsulfonylamino group, a heptylsulfonylamino group, an octylsulfonylamino group, a 2-ethylhexylsulfonylamino group, a decylsulfonylamino group, a dodecylsulfonylamino group, etc.

Of those from the viewpoint of solubility and producibility, further preferred are a hydrogen atom; an alkyl group having from 1 to 20 carbon atoms and optionally having a branched chain and a cyclic structure; an alkoxy group having from 1 to 20 carbon atoms and optionally having a branched chain and a cyclic structure; an acylamino group having from 1 to 20 carbon atoms and optionally having a branched chain and a cyclic structure; and an alkylsulfonylamino group having from 1 to 20 carbon atoms and optionally having a branched chain and a cyclic structure.

The alkyl group having from 1 to 20 carbon atoms and optionally having a branched chain and a cyclic structure is more preferably one having from 1 to 8 carbon atoms, even more preferably one having from 1 to 4 carbon atoms, from the viewpoint of solubility.

The alkoxy group having from 1 to 20 carbon atoms and optionally having a branched chain and a cyclic structure is more preferably one having from 1 to 8 carbon atoms, even more preferably one having from 1 to 4 carbon atoms, from the viewpoint of solubility.

The acylamino group having from 1 to 20 carbon atoms and optionally having a branched chain and a cyclic structure is more preferably one having from 1 to 8 carbon atoms, even more preferably one having from 2 to 5 carbon atoms, from the viewpoint of solubility.

The alkylsulfonylamino group having from 1 to 20 carbon atoms and optionally having a branched chain and a cyclic structure is more preferably one having from 1 to 8 carbon atoms, even more preferably one having from 1 to 4 carbon atoms, from the viewpoint of solubility.

In case where $X^1$ is an alkyl group having from 1 to 20 carbon atoms, an alkoxy group having from 1 to 20 carbon atoms, an acylamino group having from 1 to 20 carbon atoms, an alkoxycarbonylamino group having from 2 to 21 carbon atoms, or an alkylsulfonylamino group having from 1 to 20 carbon atoms, these groups may optionally have any arbitrary substituent.

Examples of the arbitrary substituent include a halogen atom such as a fluorine atom, a chlorine atom, a bromine atom, an iodine atom, etc.; and an alkoxy group having from 1 to 20 carbon atoms and optionally having a branched chain and a cyclic structure, such as a methoxy group, an ethoxy group, a propoxy group, an isopropoxy group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc. The alkoxy group having from 1 to 20 carbon atoms and optionally having a branched chain and a cyclic structure is especially preferably one having from 1 to 8 carbon atoms.

$X^{11}$ represents a hydrogen atom or an arbitrary substituent. Not specifically defined, the arbitrary substituent may be any known substituent usable in the coupler moiety in azo compounds. For securing high solubility in solvent and a high absorbance coefficient, the substituent concretely includes a halogen atom such as a fluorine atom, a chlorine atom, a bromine atom, an iodine atom, etc.; an alkyl group having from 1 to 20 carbon atoms and optionally having a branched chain and a cyclic structure such as a methyl group, an ethyl group, a propyl group, an isopropyl group, a cyclopropyl group, a butyl group, an isobutyl group, a sec-butyl group, a tert-butyl group, a pentyl group, a cyclopentyl group, a hexyl group, a cyclohexyl group, a heptyl group, an octyl group, a 2-ethylhexyl group, a decyl group, a dodecyl group, etc.; an alkoxy group having from 1 to 20 carbon atoms and optionally having a branched chain and a cyclic structure, such as a methoxy group, an ethoxy group, a propoxy group, an isopropoxy group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc.

Of those, further preferred are a hydrogen atom; an alkyl group having from 1 to 20 carbon atoms and optionally having a branched chain and a cyclic structure; and an alkoxy group having from 1 to 20 carbon atoms and optionally having a branched chain and a cyclic structure.

The alkyl group having from 1 to 20 carbon atoms and optionally having a branched chain and a cyclic structure is more preferably one having from 1 to 8 carbon atoms, even more preferably one having from 1 to 4 carbon atoms, still more preferably one having one carbon atom, from the viewpoint of solubility.

The alkoxy group having from 1 to 20 carbon atoms and optionally having a branched chain and a cyclic structure is more preferably one having from 1 to 8 carbon atoms, even more preferably one having from 1 to 4 carbon atoms, still more preferably one having one carbon atom, from the viewpoint of solubility.

In case where $X^{11}$ is an alkyl group having from 1 to 20 carbon atoms or an alkoxy group having from 1 to 20 carbon atoms, these groups may optionally have any arbitrary substituent. Examples of the arbitrary substituent include a halogen atom such as a fluorine atom, a chlorine atom, a bromine atom, an iodine atom, etc.; and an alkoxy group having from 1 to 20 carbon atoms and optionally having a branched chain and a cyclic structure, such as a methoxy group, an ethoxy group, a propoxy group, an isopropoxy group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc. The alkoxy group having from 1 to 20 carbon atoms and optionally having a branched chain and a cyclic structure is especially preferably one having from 1 to 8 carbon atoms.

The compound represented by the above-mentioned general formula (1) may have any other substituent than the substituents $A^1$, $X^1$, $X^{11}$, $R^1$ and $R^2$. Specific examples of the other substituent include a halogen atom such as a fluorine atom, a chlorine atom, a bromine atom, an iodine atom, etc.; an alkyl group having from 1 to 20 carbon atoms and optionally having a branched chain and a cyclic structure such as a methyl group, an ethyl group, a propyl group, an isopropyl group, a cyclopropyl group, a butyl group, an isobutyl group, a sec-butyl group, a tert-butyl group, a pentyl group, a cyclopentyl group, a hexyl group, a cyclohexyl group, a heptyl group, an octyl group, a 2-ethylhexyl group, a decyl group, a dodecyl group, etc.; and an alkoxy group having from 1 to 20 carbon atoms and optionally having a branched chain and a cyclic structure, such as a methoxy group, an ethoxy group, a propoxy group, an isopropoxy group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc.

Of the compounds represented by the general formula (1), preferred are azo compounds represented by the following structural formula (8) as having a high solubility in solvent and having a high molar absorbance coefficient.

[Chem. 9]

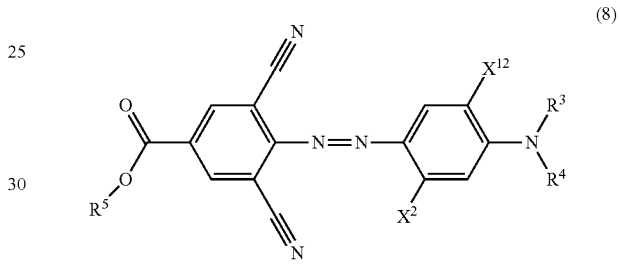

(8)

[In the general formula (8), $R^3$ and $R^4$ each independently represent an alkyl group having from 1 to 20 carbon atoms and optionally having a substituent; $R^5$ represents an alkyl group having from 4 to 20 carbon atoms and having a branched chain and optionally having a substituent; $X^2$ and $X^{12}$ each independently represent a hydrogen atom or an arbitrary substituent.]

The alkyl group for $R^3$ and $R^4$ has the same meaning as the alkyl group for $R^1$ and $R^2$ in the general formula (1), and the substituent that the group may have is also the same. Of those, preferred is one having 2 or more carbon atoms, more preferred is one having 4 or more carbon atoms, and even more preferred is one having 6 or more carbon atoms. Also preferred is one having 16 or less carbon atoms, and more preferred is one having 12 or less carbon atoms. When the carbon number of the group falls within a suitable range, then the compound may have a high solubility in solvent and a high gram absorbance coefficient.

Also preferably at least one of $R^3$ and $R^4$ is a branched alkyl group. More preferably, both $R^3$ and $R^4$ are branched alkyl groups from the viewpoint of solubility.

$X^2$ represents a hydrogen atom or an arbitrary substituent. Not specifically defined, the arbitrary substituent may be any known substituent usable in the coupler moiety in azo compounds. For securing high solubility in solvent and a high absorbance coefficient, concretely, preferred is use of the substituent group of $X^1$ in the general formula (1) and the substituent that the group may have. Of those, from the viewpoint of solubility and producibility, more preferred are a hydrogen atom; an alkyl group having from 1 to 20 carbon atoms and optionally having a branched chain and a cyclic structure; an alkoxy group having from 1 to 20 carbon atoms and optionally having a branched chain and a cyclic structure; an acylamino group having from 1 to 20 carbon atoms and optionally having a branched chain and a cyclic structure; and an alkylsulfonylamino group having from 1 to 20 carbon atoms and optionally having a branched chain and a cyclic structure.

The alkyl group having from 1 to 20 carbon atoms and optionally having a branched chain and a cyclic structure for $X^2$ is more preferably one having from 1 to 8 carbon atoms, even more preferably one having from 1 to 4 carbon atoms, from the viewpoint of solubility.

The alkoxy group having from 1 to 20 carbon atoms and optionally having a branched chain and a cyclic structure for $X^2$ is more preferably one having from 1 to 8 carbon atoms, even more preferably one having from 1 to 4 carbon atoms, from the viewpoint of solubility.

The acylamino group having from 1 to 20 carbon atoms and optionally having a branched chain and a cyclic structure for $X^2$ is more preferably one having from 1 to 8 carbon atoms, even more preferably one having from 2 to 5 carbon atoms, from the viewpoint of solubility.

The alkylsulfonylamino group having from 1 to 20 carbon atoms and optionally having a branched chain and a cyclic structure for $X^2$ is more preferably one having from 1 to 8 carbon atoms, even more preferably one having from 1 to 4 carbon atoms, from the viewpoint of solubility.

$X^{12}$ represents a hydrogen atom or an arbitrary substituent. Not specifically defined, the arbitrary substituent may be any known substituent usable in the coupler moiety in azo compounds. For securing high solubility in solvent and a high absorbance coefficient, concretely, preferred is use of the substituent group of $X^{11}$ in the general formula (1) and the substituent that the group may have. Of those, from the viewpoint of solubility and producibility, more preferred are a hydrogen atom; an alkyl group having from 1 to 20 carbon atoms and optionally having a branched chain and a cyclic structure; and an alkoxy group having from 1 to 20 carbon atoms and optionally having a branched chain and a cyclic structure.

The alkyl group having from 1 to 20 carbon atoms and optionally having a branched chain and a cyclic structure for $X^{12}$ is more preferably one having from 1 to 8 carbon atoms, even more preferably one having from 1 to 4 carbon atoms, still more preferred is one having one carbon atom, from the viewpoint of solubility.

The alkoxy group having from 1 to 20 carbon atoms and optionally having a branched chain and a cyclic structure for $X^{12}$ is more preferably one having from 1 to 8 carbon atoms, even more preferably one having from 1 to 4 carbon atoms, still more preferred is one having one carbon atom, from the viewpoint of solubility.

$R^5$ represents an alkyl group having from 4 to 20 carbon atoms and having a branched chain and optionally having a substituent. Of the group, preferred is one having from 4 to 10 carbon atoms for securing a high solubility in solvent and a high gram absorbance coefficient.

The substituent that $R^5$ may have is not specifically defined. Specific examples of the substituent include a halogen atom such as a fluorine atom, a chlorine atom, a bromine atom, an iodine atom, etc.; an alkoxy group having from 1 to 20 carbon atoms and optionally having a branched chain and a cyclic structure, such as a methoxy group, an ethoxy group, a propoxy group, an isopropoxy group, a cyclopropoxy group, a butoxy group, an isobutoxy group, a sec-butoxy group, a tert-butoxy group, a pentyloxy group, a cyclopentyloxy group, a hexyloxy group, a cyclohexyloxy group, a heptyloxy group, an octyloxy group, a 2-ethylhexyloxy group, a decyloxy group, a dodecyloxy group, etc.; an alkoxycarbonyl group having from 2 to 21 carbon atoms and optionally having a branched chain and a cyclic structure, such as a methoxycarbonyl group, an ethoxycarbonyl group, a propoxycarbonyl group, an isopropoxycarbonyl group, a cyclopropoxycarbonyl group, a butoxycarbonyl group, an isobutoxycarbonyl group, a sec-butoxycarbonyl group, a tert-butoxycarbonyl group, a pentyloxycarbonyl group, a cyclopentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a decyloxycarbonyl group, a dodecyloxycarbonyl group, etc.; an acyloxy group having from 1 to 20 carbon atoms and optionally having a branched chain and a cyclic structure, such as a formyloxy group, an acetyloxy group, a propionyloxy group, a butyryloxy group, an isobutyloxy group, a cyclopropylcarbonyloxy group, a valeryloxy group, an isovaleryloxy group, a pivaloyloxy group, a hexanoyloxy group, a cyclopentylcarbonyloxy group, a heptanoyloxy group, a cyclohexylcarbonyloxy group, an octanoyloxy group, a 2-ethylhexanoyloxy group, a decanoyloxy group, a dodecanoyloxy group, etc.; an aryl group such as a phenyl group, a naphthyl group, etc.; a cyano group, etc.

Specific examples of the azo compound represented by the general formula (1) are shown below. Not overstepping the spirit and the scope thereof, the present invention is not limited to these.

[Chem. 10]

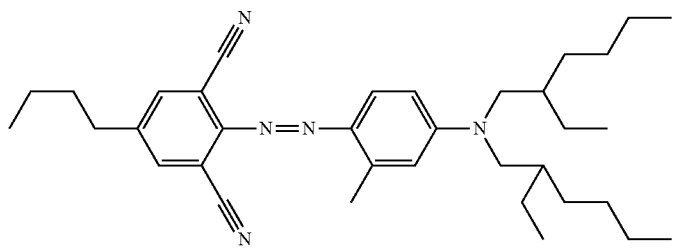

-continued
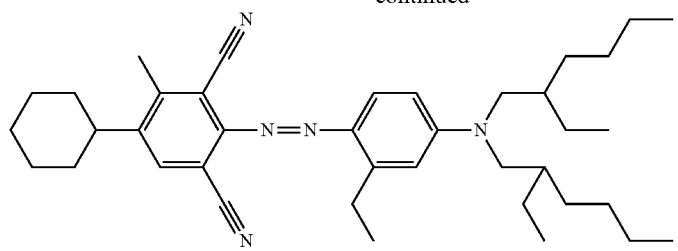
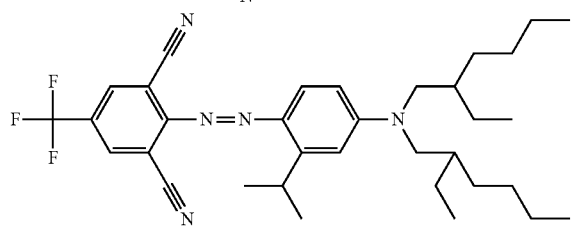
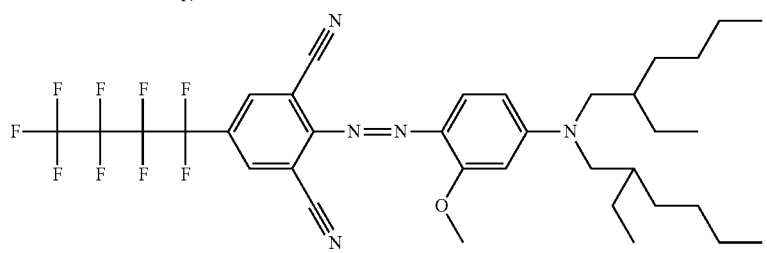
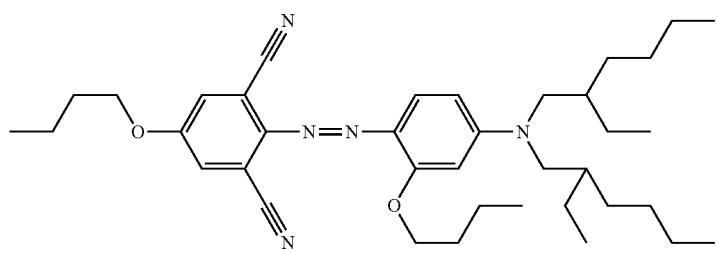
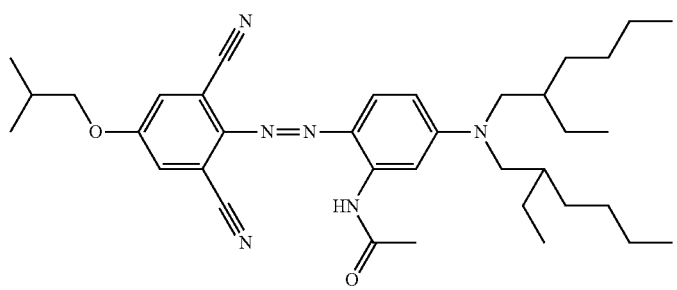
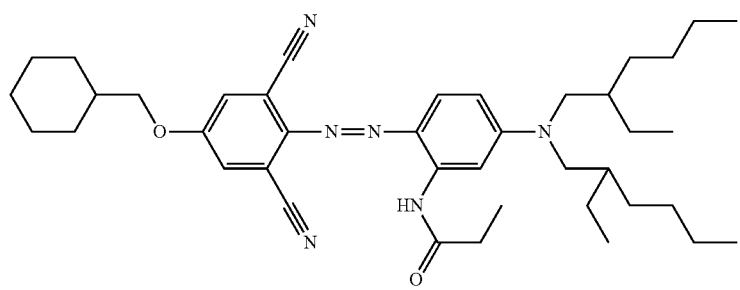

-continued
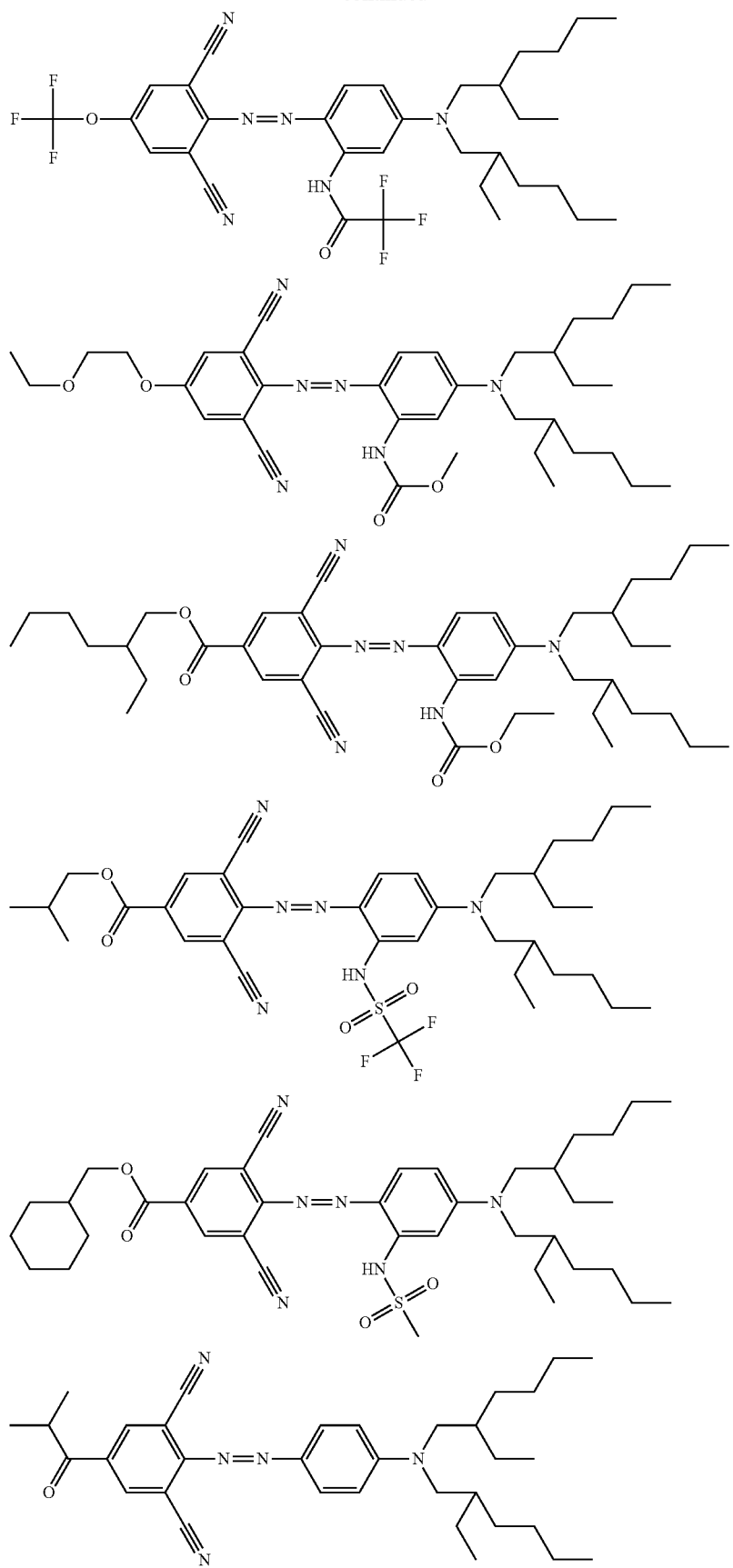

-continued
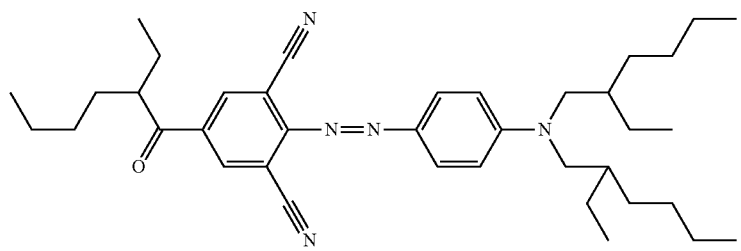
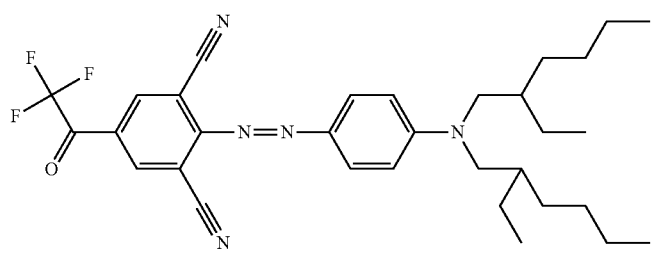
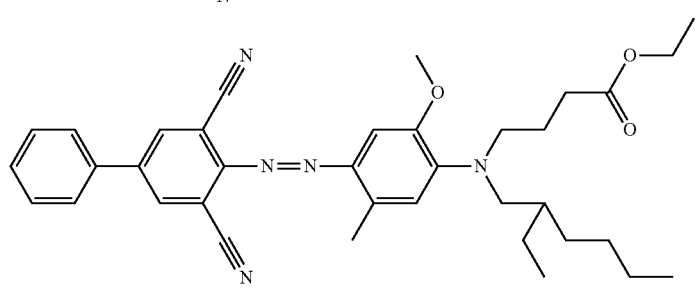
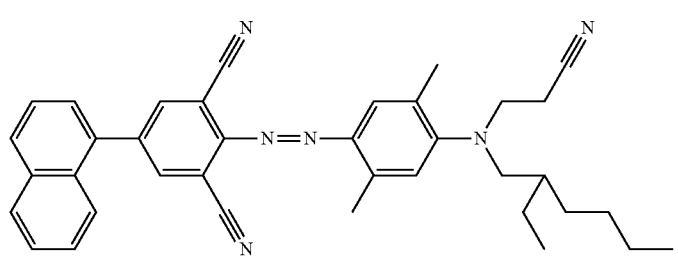
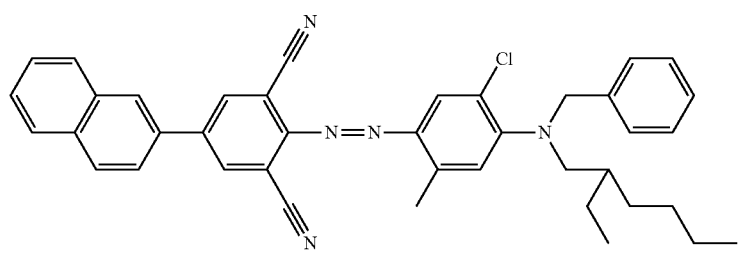
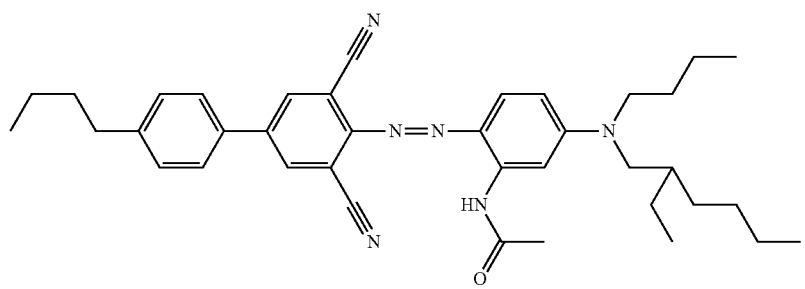

-continued
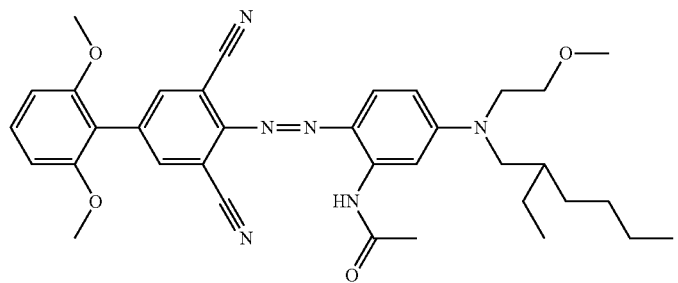
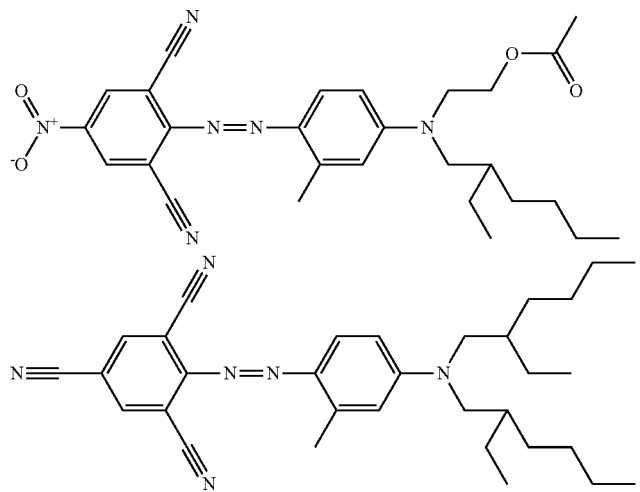
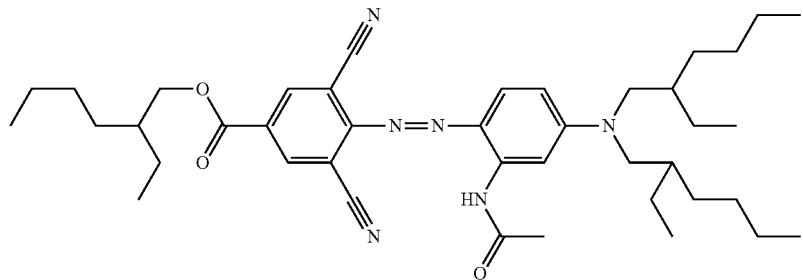
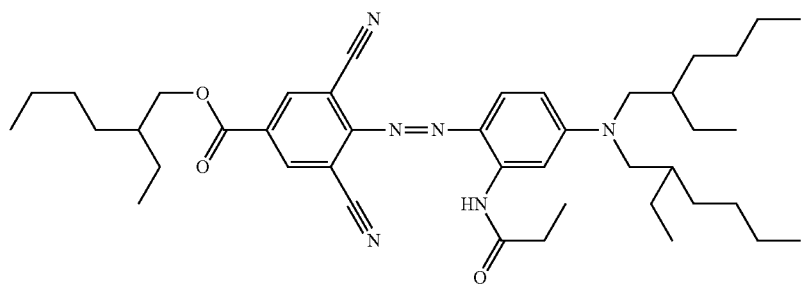
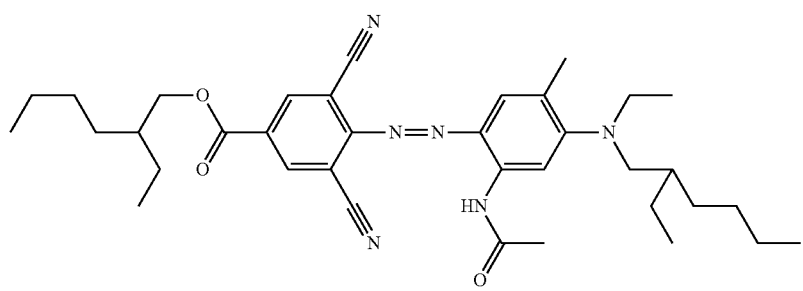

-continued
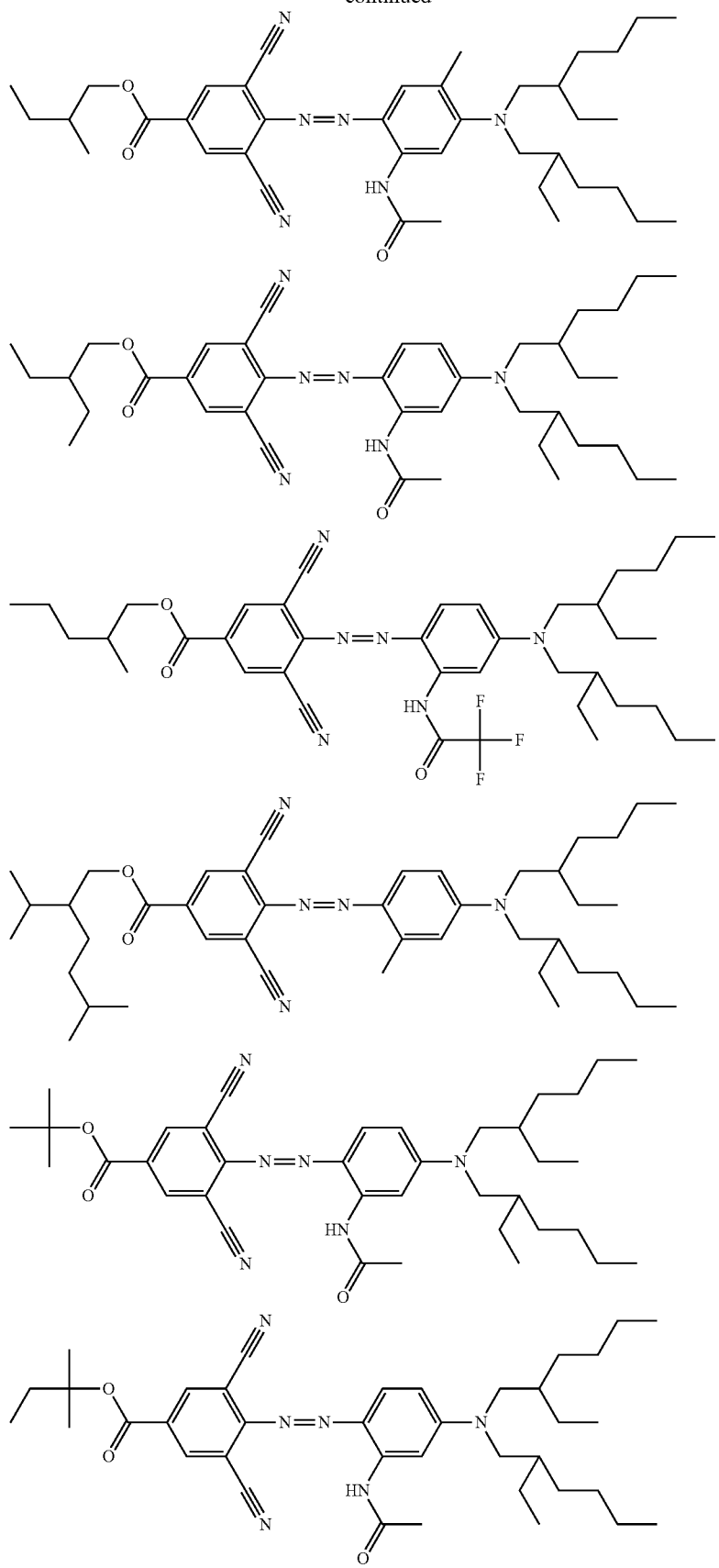

-continued

[Chem. 11]

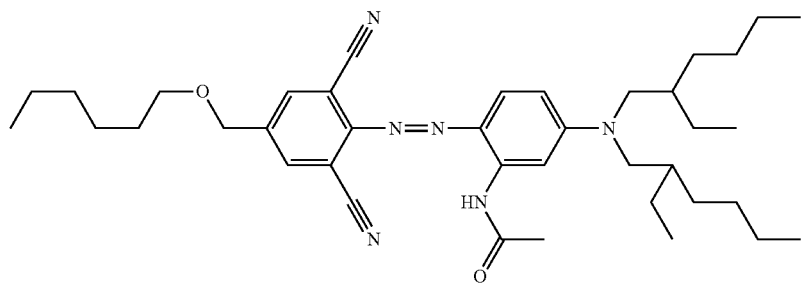

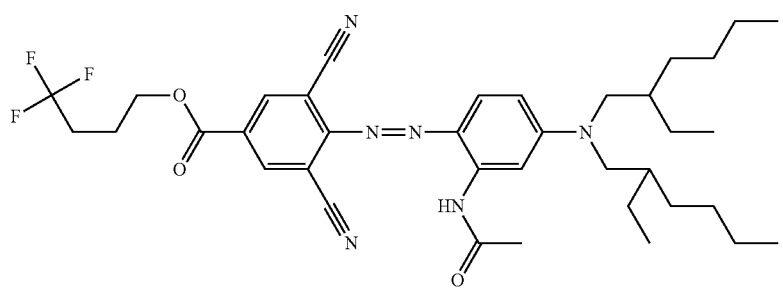

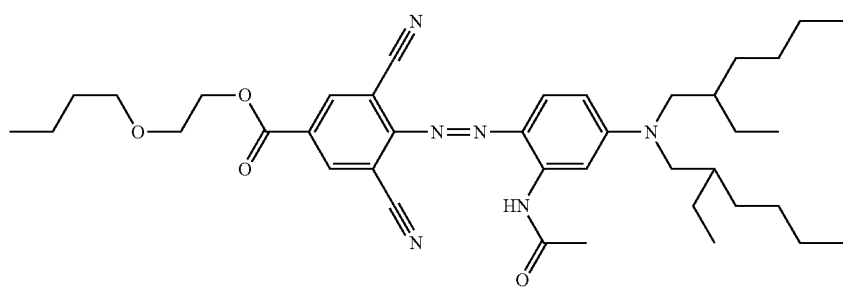

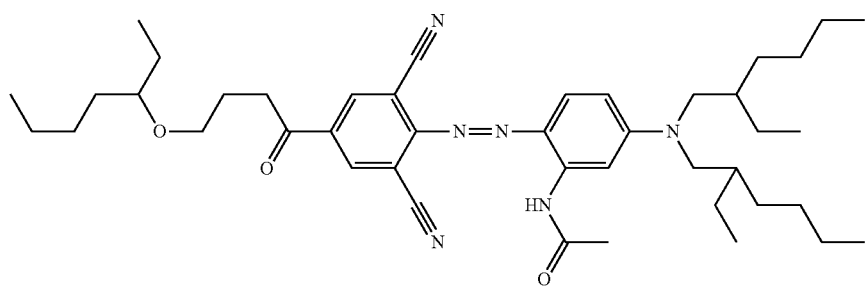

Including the substituents, in any therein, the azo compound of the present invention preferably has a molecular weight of 3000 or less, more preferably 1500 or less. Also preferably, the molecular weight is 350 or more. Having a molecular weight falling within a suitable range, the compound can have a good gram absorbance coefficient.

The compound represented by the general formula (1) can be synthesized, for example, by diazotizing a compound represented by a general formula (9), then coupling reaction it with a compound represented by a general formula (10) to give a compound represented by a general formula (11) and thereafter cyanizing the compound with a reactant, copper(I) cyanide.

[Chem. 12]

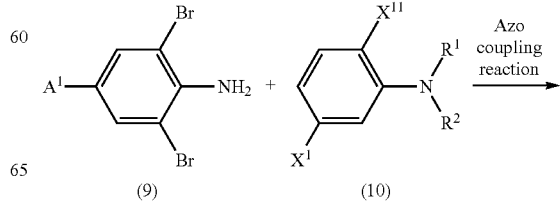

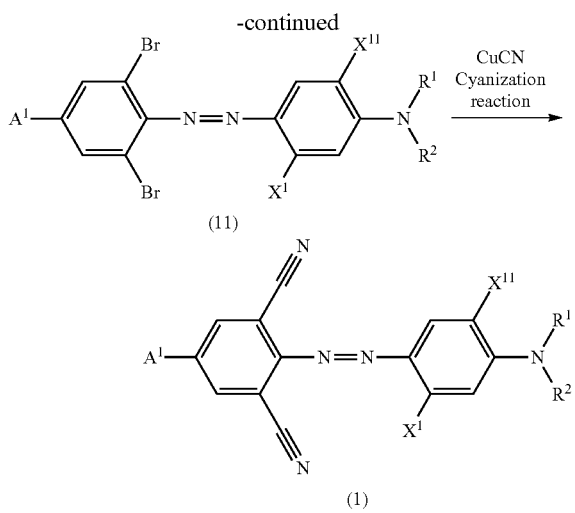

[In the general formulae (9), (10) and (11), $A^1$, $X^1$, $X^{11}$, $R^1$ and $R^2$ have the same meanings as those in the general formula (1).]

The azo compound of the present invention is characterized in that its solubility in solvent, especially its solubility in a solvent having a relative permittivity at 22° C. of 3 or less and having a solubility in water at 25° C. of 20 mg/L or less is excellent. The azo compound of the present invention has a solubility in an n-decane solution at 5° C. of generally 1% by mass or more, preferably 3% by mass or more, more preferably 5% by mass or more. The solubility of the compound is preferably higher, but is generally 80% by mass or less. Since the solubility of the compound is on a specific level or higher, the compound could make it possible to secure good image display on display devices.

In case where the azo compound of the present invention is used in electrowetting displays, the compound is preferably insoluble in water in view of the principles of the displays. Here, "insolubility in water" means that the solubility of the compound in water at 25° C. and under one atmospheric pressure is 0.1% by mass or less, preferably 0.01% by mass or less.

Preferably, the molar absorbance coefficient of the azo compound of the present invention is 40000 (L·mol$^{-1}$·cm$^{-1}$) or more, more preferably 50000 (L·mol$^{-1}$·cm$^{-1}$) or more for satisfying the performance of display devices.

A value of the product, $\epsilon C$, of the molar absorbance coefficient at the absorption maximum wavelength of an n-decane solution of the azo compound, $\epsilon$(L·mol$^{-1}$·cm$^{-1}$), and the saturation solubility of the solution at 5° C., C (mol·L$^{-1}$), is generally 500 cm$^{-1}$ or more, preferably 1000 cm$^{-1}$ or more. Not specifically defined, the upper limit is generally 60000 cm$^{-1}$ or less.

The concentration of the azo compound in the ink of the present invention may be controlled at any desired value in accordance with the intended purpose thereof. For example, in case where the compound is used as a dye for electrowetting displays, the concentration thereof is generally 1% by mass or more, or that is, the compound may be diluted in a nonpolar solvent in accordance with the desired concentration thereof. Preferably, the concentration is 3% by mass or more, more preferably 5% by mass or more. Also preferably, the concentration is generally about 80% by mass or less.

The absorption maximum wavelength in a wavelength range of from 350 to 750 nm of the azo compound of the present invention, when dissolved in an n-decane solution, is not specifically defined, but is preferably within a range of 570 nm or more and less than 630 nm from the viewpoint that OD (optical density) of the ink can be increased.

Here, OD of ink means that, when the ink has passed through an object, how the light intensity would be attenuated, and a higher value of OD indicates that the light intensity greatly reduces.

The ink of the present invention may contain one type of the above-mentioned azo compound alone, but may contain two or more types of the compounds in any desired combination and in any desired ratio.

The azo compound of the present invention is excellent in solubility in solvent and has a high absorbance coefficient, and is therefore useful as a material for optical shutters and a material for displays, especially a material for electrowetting displays and a material for electrophoretic displays.

The lower limit of the ink viscosity of the ink of the present invention at a temperature of 25° C. is not specifically defined, but is, in general, preferably 0.1 mPa·s or more. The upper limit is preferably 10000 mPa·s or less, more preferably 1000 mPa·s or less, even more preferably 100 mPa·s or less. When the viscosity thereof is too large, then the ink would interfere with operation of display devices.

Regarding the relative permittivity and the viscosity of the solvent in the present invention as well as those of the ink containing the solvent and a dye and the like, the difference between the values of the solvent and those of the ink is preferably smaller as capable of reducing the influence thereof on the driving characteristics in use in display devices, etc.

Accordingly, within a range not detracting from the advantageous effects of the present invention and if desired, the ink of the present invention may contain any desired additive suitable to the intended purposes; however, it is desirable that the additive, if any, would not change the characteristics of the solvent used in the ink.

(Other Compounds)

The ink of the present invention may contain the above-mentioned azo compound alone, or may contain any other compound to attain a desired color tone. For example, compounds of different colors of yellow, red, blue, violet, orange and the like may be mixed with the azo compound of the present invention to provide other colors such as black, etc.

For example, the azo compound of the present invention has a maximum absorption wavelength in a high-visibility range, and therefore a combination of the azo compound of the present invention and an orange or the like compound may provide a black ink. On the other hand, when a red, blue, yellow or the like compound is combined with the azo compound of the present invention, then a black ink could be provided. In that manner, various compounds may be combined suitable in accordance with the intended purposes, etc.

The other compound which the ink of the present invention may contain may be suitably selected from compounds that are soluble or dispersible in the medium to be used, within a range not detracting from the advantageous effects of the present invention and in any desired manner.

In case where the ink of the present invention is used in electrowetting displays, any arbitrary compound may be selected and used as the other compound to be combined therewith. For example, usable here are nitroso compounds, nitro compounds, monoazo compounds, disazo compounds, triazo compounds, polyazo compounds, stilbene compounds, carotenoid compounds, di arylmethane compounds, triarylmethane compounds, xanthene compounds, acridine compounds, quinoline compounds, methine compounds, thiazole compounds, isothiazole compounds, indamine compounds, indophenol compounds, azine compounds, oxazine compounds, thiazine compounds, heterocyclic compounds, sulfide dyes, lactone compounds, hydroxyketone compounds, aminoketone compounds, anthraquinone compounds, indigo compounds, phthalocyanine compounds, pyrazole compounds, cyanovinyl compounds, natural dyes, oxidation dyes, inorganic pigments, metal complexes, carbon black, etc.

Concretely, for example, there are mentioned Oil Blue N (alkylamine-substituted anthraquinone), Solvent Green, Solvent Blue, Sudan Blue, Sudan Red, Sudan Yellow, Sudan Black, Disperse Violet, Disperse Red, Disperse Blue, Disperse Yellow, compounds described in WO2009/063880, compounds described in WO2010/031860, compounds described in WO2012/033177, compounds described in JP-A 57-125263, etc.

Of those, the ink of the present invention preferably contains, though not specifically defined, at least one selected from a group consisting of heterocyclic compounds, cyanovinyl compounds and anthraquinone compounds, and combining any of those compounds in any desired manner realizes inks of different colors such as black, etc.

Examples of the heterocyclic compounds are not specifically defined. Preferred is at least one compound selected from a group consisting of general formulae (2) to (5) mentioned below.

As the heterocyclic compounds, there are mentioned compounds represented by the following general formula (2).

[Chem. 13]

(2)

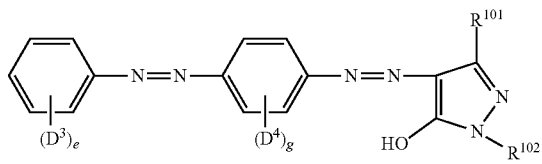

[In the general formula (2), $R^{101}$ and $R^{102}$ each independently represent a hydrogen atom or an arbitrary substituent; $D^3$ and $D^4$ each independently represent an arbitrary substituent; e indicates an integer of from 0 to 5, and when e is 2 or more, two or more $D^3$s existing in one molecule may be the same or different; g indicates an integer of from 0 to 4, and when g is 2 or more, two or more $D^4$s existing in one molecule may be the same or different.]

In the general formula (2), $R^{101}$ and $R^{102}$ each independently represent a hydrogen atom or an arbitrary substituent.

Not detracting from the advantageous effects of the present invention, $R^{101}$ is not specifically defined, but is preferably a hydrogen atom, an alkyl group having from 1 to 20 carbon atoms and optionally having a substituent, an alkoxy group having from 1 to 20 carbon atoms and optionally having a substituent, an aryl group having from 6 to 20 carbon atoms and optionally having a substituent, a heteroaryl group having from 2 to 20 carbon atoms and optionally having a substituent, a group —COOR$^{103}$, a group —NR$^{107}$R$^{108}$ or a group —COR$^{112}$, for securing high solubility in solvent and a high absorbance coefficient.

$R^{103}$, $R^{107}$, $R^{108}$ and $R^{112}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

Not detracting from the advantageous effects of the present invention, $R^{102}$ is not specifically defined, but is preferably a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent, for securing high solubility in solvent and a high absorbance coefficient.

The alkyl group for $R^{101}$, $R^{102}$, $R^{103}$, $R^{107}$, $R^{108}$ and $R^{112}$ has, concretely, the same meaning as the alkyl group exemplified for $R^1$ in the above-mentioned general formula (1), and the substituent that the group may have is also the same. The alkyl group for $R^{101}$, $R^{102}$, $R^{103}$, $R^{107}$, $R^{108}$ and $R^{112}$ is preferably one having 16 or less carbon atoms, more preferably one having 10 or less carbon atoms, even more preferably one having 6 or less carbon atoms. Having a carbon number that falls within the suitable range, the compound could have excellent solubility in solvent and could have a high gram absorbance coefficient.

The aryl group for $R^{101}$, $R^{102}$, $R^{103}$, $R^{107}$, $R^{108}$ and $R^{112}$ is a residue to be derived from a single ring or from a condensed ring composed of from 2 to 4 single rings, by removing one hydrogen atom therefrom, and specific examples thereof include residues of a benzene ring, a naphthalene ring, an anthracene ring, a phenanthrene ring, a perylene ring, a tetracene ring, a pyrene ring, a benzopyrene ring, a chrysene ring, a triphenylene ring, an acenaphthene ring, a fluoranthene ring, a fluorene ring, etc.

The heteroaryl group for $R^{101}$, $R^{102}$, $R^{103}$, $R^{107}$, $R^{108}$ and $R^{112}$ is a residue to be derived from a single ring or from a condensed ring composed of from 2 to 4 single rings, by removing one hydrogen atom therefrom, and specific examples thereof include residues of a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, a benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a phenanthridine ring, a benzimidazole ring, a perimidine ring, a quinazoline ring, a quinazolinone ring, an azurene ring, etc.

The substituent that the aryl group and the heteroaryl group for $R^{101}$, $R^{102}$, $R^{103}$, $R^{107}$, $R^{108}$ and $R^{112}$ may have is not specifically defined. Specific examples of the substituent include a halogen atom, an alkyl group having from 1 to 20 carbon atoms, an alkoxy group having from 1 to 20 carbon atoms, an alkoxycarbonyl group having from 1 to 20 carbon atoms, etc.

$D^3$ represents an arbitrary substituent. Not detracting from the advantageous effects of the present invention, $D^3$ is not specifically defined, but is preferably a halogen atom, an alkyl group having from 1 to 20 carbon atoms and optionally having a substituent, an alkoxy group having from 1 to 20 carbon atoms and optionally having a substituent, a cyano group, a hydroxy group, a group —COOR$^{104}$, a group —NHCOR$^{109}$, a group —NHSO$_2$R$^{110}$, a group —COR$^{113}$ or a group —OCOR$^{115}$, for securing high solubility in solvent and a high absorbance coefficient.

e indicates an integer of from 0 to 5, and when e is 2 or more, two or more D$^3$s existing in one molecule may be the same or different.

R$^{104}$, R$^{109}$, R$^{110}$, R$^{113}$ and R$^{115}$ each independently represent an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for D$^3$, R$^{104}$, R$^{109}$, R$^{110}$, R$^{113}$ and R$^{115}$ has, concretely, the same meaning as that of the alkyl group exemplified for R$^1$ in the above-mentioned general formula (1), and the substituent that the group may have is also the same. The alkyl group for D$^3$, R$^{104}$, R$^{109}$, R$^{110}$, R$^{113}$ and R$^{115}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The alkoxy group for D$^3$ has the same meaning as that of the alkoxy group exemplified for R$^1$ in the above-mentioned general formula (1), and the substituent that the group may have is also the same. The alkoxy group for D$^3$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for R$^{104}$, R$^{109}$, R$^{110}$, R$^{113}$ and R$^{115}$ has, concretely, the same meaning as that of the aryl group exemplified for R$^{101}$, and the substituent that the group may have is also the same as that the aryl group exemplified for R$^{101}$ may have.

The heteroaryl group for R$^{104}$, R$^{109}$, R$^{110}$, R$^{113}$ and R$^{115}$ has, concretely, the same meaning as that of the heteroaryl group exemplified for R$^{101}$, and the substituent that the group may have is also the same as that the heteroaryl group exemplified for R$^{101}$ may have.

D$^4$ represents an arbitrary substituent. Not detracting from the advantageous effects of the present invention, D$^4$ is not specifically defined, but is preferably a halogen atom, an alkyl group having from 1 to 20 carbon atoms and optionally having a substituent, an alkoxy group having from 1 to 20 carbon atoms and optionally having a substituent, a cyano group, a group —COOR$^{105}$, a group —NHCOR$^{106}$, a group —NHSO$_2$R$^{111}$ or a group —COR$^{114}$, for securing high solubility in solvent and a high absorbance coefficient.

g indicates an integer of from 0 to 4, and when g is 2 or more, two or more D$^4$s existing in one molecule may be the same or different.

R$^{105}$, R$^{106}$, R$^{111}$ and R$^{114}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for D$^4$, R$^{105}$, R$^{106}$, R$^{111}$ and R$^{114}$ has, concretely, the same meaning as that of the alkyl group exemplified for R$^1$ in the above-mentioned general formula (1), and the substituent that the group may have is also the same. The alkyl group for D$^4$, R$^{105}$, R$^{106}$, R$^{111}$ and R$^{114}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The alkoxy group for D$^4$ has the same meaning as that of the alkoxy group exemplified for R$^1$ in the above-mentioned general formula (1), and the substituent that the group may have is also the same. The alkoxy group for D$^4$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for R$^{105}$, R$^{106}$, R$^{111}$ and R$^{114}$, has, concretely, the same meaning as that of the aryl group exemplified for R$^{101}$, and the substituent that the group may have is also the same as that the aryl group exemplified for R$^{101}$ may have.

The heteroaryl group for R$^{105}$, R$^{106}$, R$^{111}$ and R$^{114}$ has, concretely, the same meaning as that of the heteroaryl group exemplified for R$^{101}$, and the substituent that the group may have is also the same as that the heteroaryl group exemplified for R$^{101}$ may have.

Specific examples of the compound represented by the above-mentioned general formula (2) are shown below; however, not overstepping the scope and the spirit thereof, the present invention is not limited to these. In this description, Ac means an acetyl group, Me means a methyl group, Bu means a butyl group, and Ph means a phenyl group.

[Chem. 14]

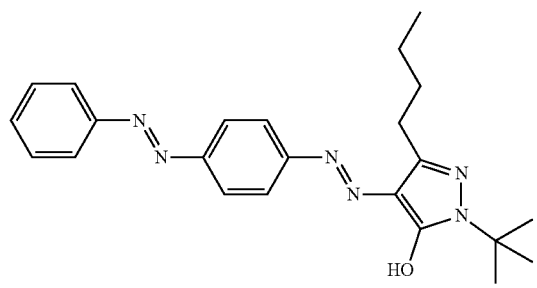

-continued
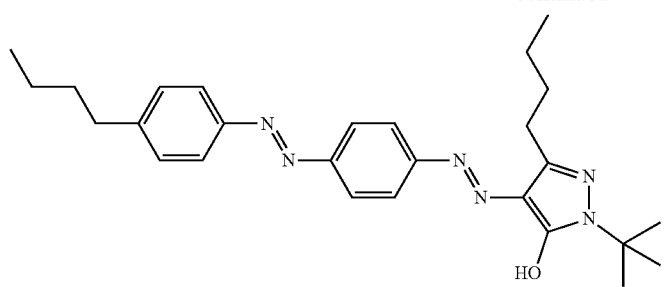
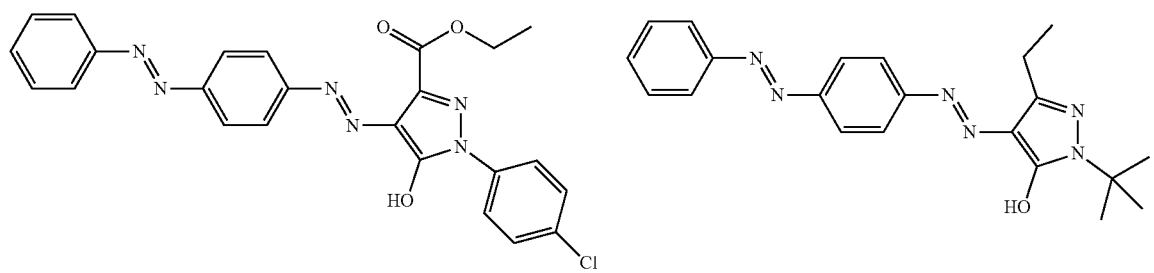
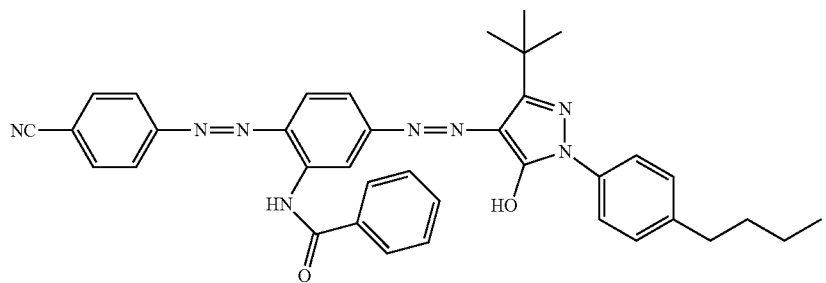
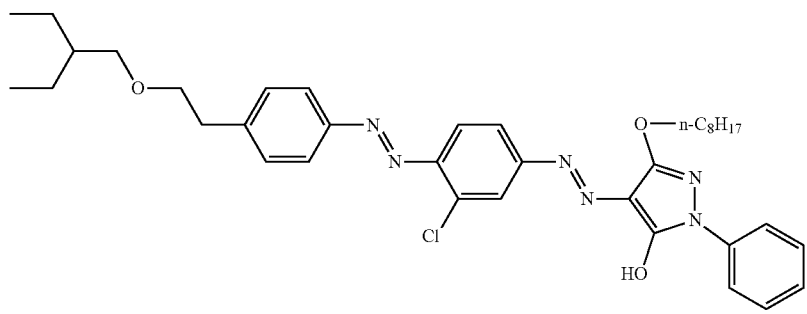
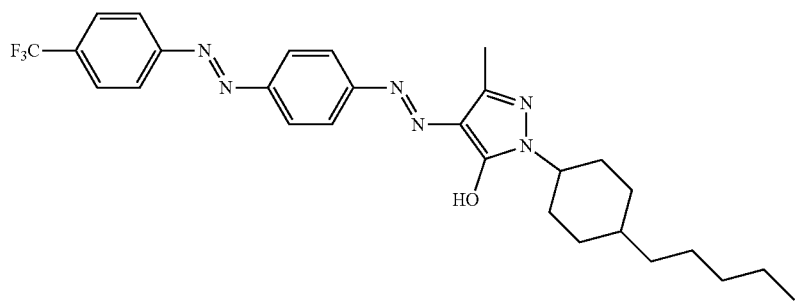

-continued
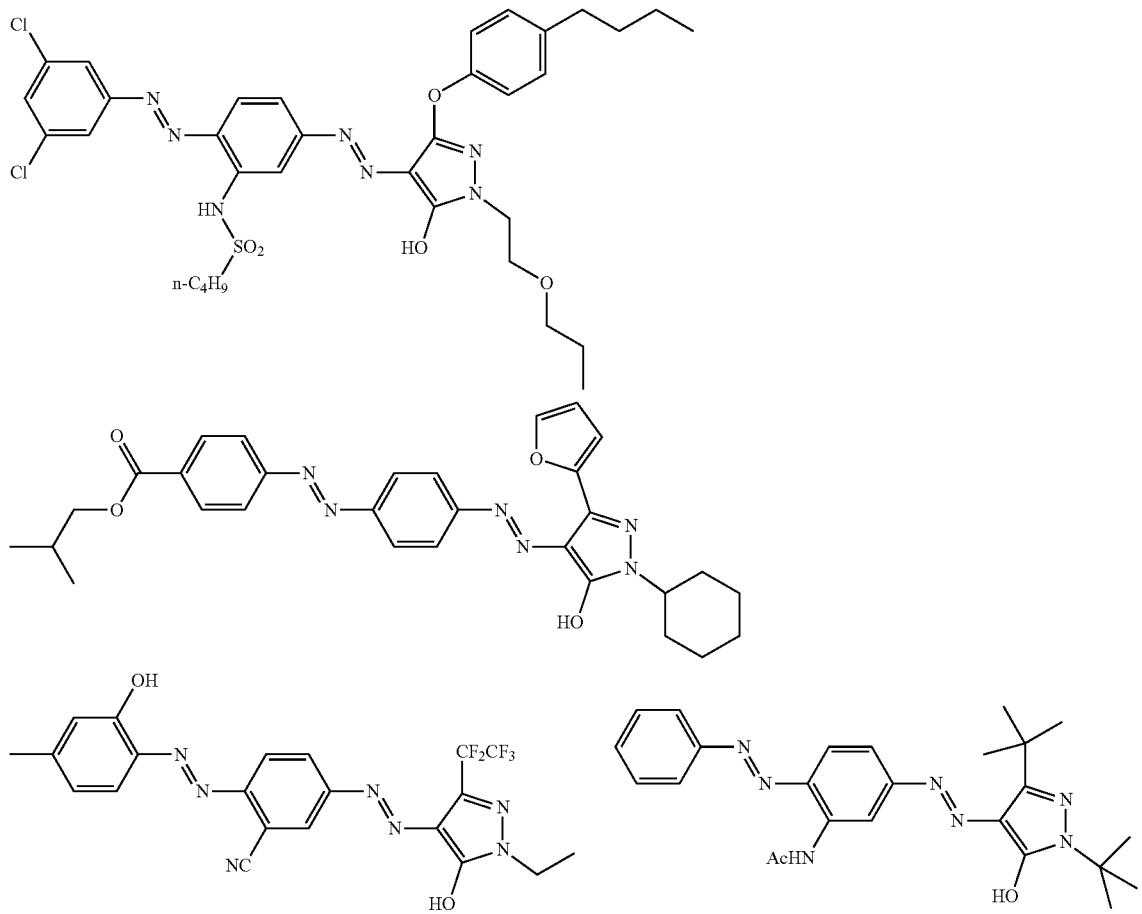
[Chem. 15]
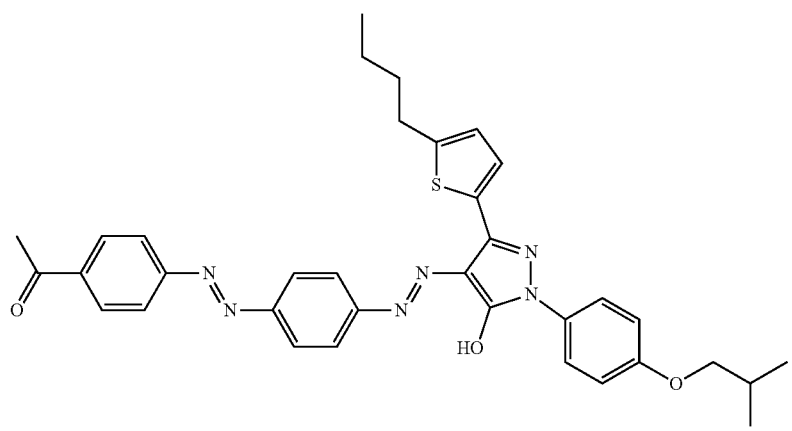
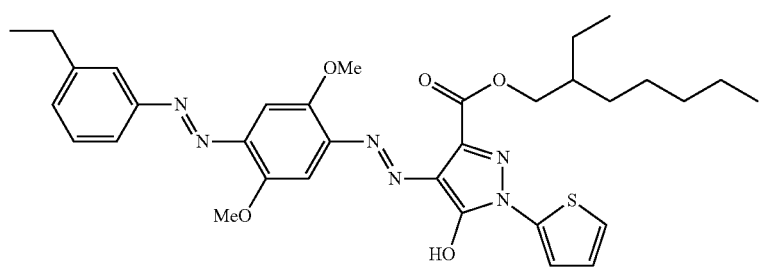

-continued
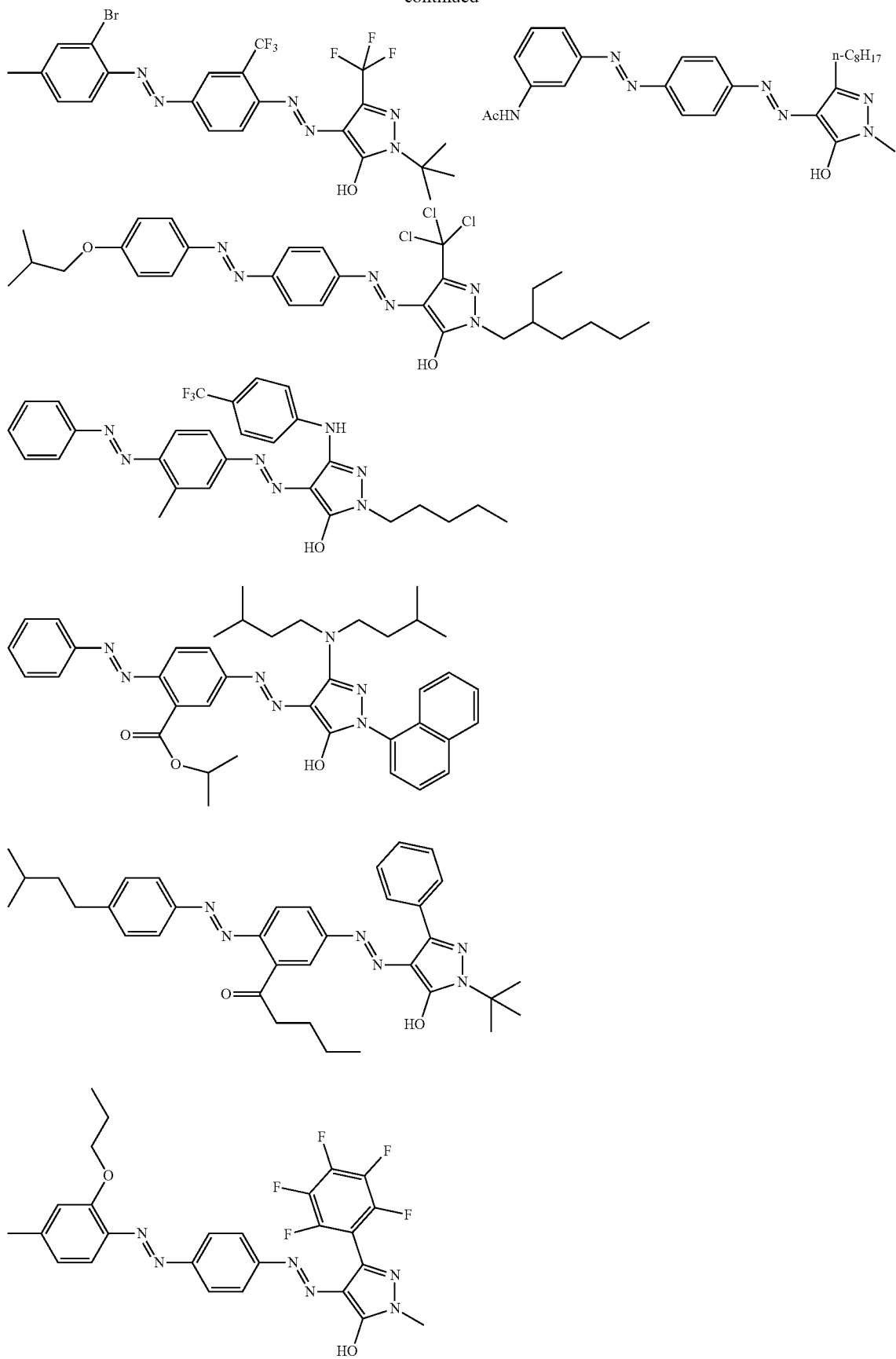

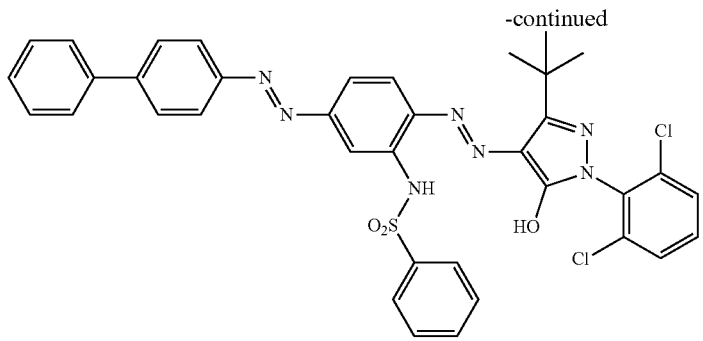

The compounds represented by the general formula (2) can be synthesized, for example, according to the method described in WO2009/063880.

As the heterocyclic compound, there are mentioned compounds represented by the following general formula (3).

[Chem. 16]

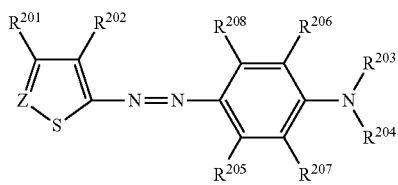

(3)

[In the general formula (3), $R^{201}$ to $R^{208}$ each independently represent a hydrogen atom or an arbitrary substituent; and Z represents a nitrogen atom, or a methine group optionally having a substituent.]

$R^{201}$ represents a hydrogen atom or an arbitrary substituent. Not detracting from the advantageous effects of the present invention, $R^{201}$ is not specifically defined, but is preferably a hydrogen atom, or an alkyl group having from 1 to 20 carbon atoms and optionally having a substituent, for securing high absorbance coefficient.

The alkyl group having from 1 to 20 carbon atoms and optionally having a substituent for $R^{201}$ has the same meaning as the alkyl group exemplified for $R^1$ in the above-mentioned general formula (1), and the substituent that the group may have is also the same. Bonding to Z, $R^{201}$ may form a cyclic structure.

Preferably, $R^{201}$ is a substituent having a small molecular weight from the viewpoint of gram absorbance coefficient. Concretely, preferred is a substituent having 16 or less carbon atoms, more preferred is one having 10 or less carbon atoms, and even more preferred is one having 6 or less carbon atoms. Having a carbon number that falls within the suitable range, the compound could have excellent solubility in solvent and could have a high gram absorbance coefficient.

$R^{201}$ is preferably an unsubstituted alkyl group from the viewpoint of producibility. More preferred is an unsubstituted alkyl group having from 1 to 4 carbon atoms, such as a methyl group, an ethyl group, a propyl group, an isopropyl group, a butyl group, etc.

$R^{202}$ represents a hydrogen atom or an arbitrary substituent. Not detracting from the advantageous effects of the present invention, $R^{202}$ is not specifically defined, but is preferably a cyano group or a group $COOR^{209}$, for securing high solubility in solvent and a high absorbance coefficient.

$R^{209}$ represents an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $R^{209}$ has, concretely, the same meaning as that of the alkyl group exemplified for $R^1$ in the above-mentioned general formula (1), and the substituent that the group may have is also the same. The alkyl group for $R^{209}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $R^{209}$ has, concretely, the same meaning as that of the aryl group exemplified for $R^{101}$ in the above-mentioned general formula (2), and the substituent that the group may have has also the same meaning as that of the aryl group exemplified for $R^{101}$ in the general formula (2).

The heteroaryl group for $R^{209}$ has, concretely, the same meaning as that of the heteroaryl group exemplified for $R^{101}$ in the above-mentioned general formula (2), and the substituent that the group may have has also the same meaning as that of the heteroaryl group exemplified for $R^{101}$ in the general formula (2).

$R^{203}$ and $R^{204}$ each independently represent a hydrogen atom or an arbitrary substituent. Not detracting from the advantageous effects of the present invention, $R^{203}$ and $R^{204}$ are not specifically defined, but preferably, each independently represents an alkyl group having from 1 to 20 carbon atoms and optionally having a substituent, for securing high solubility in solvent and a high absorbance coefficient.

Bonding to each other, $R^{203}$ and $R^{204}$ may form a cyclic structure. Also bonding to $R^{206}$ or $R^{207}$, respectively, $R^{203}$ and $R^{204}$ may form a cyclic structure.

The alkyl group for $R^{203}$ and $R^{204}$ has, concretely, the same meaning as that of the alkyl group exemplified for $R^1$ in the above-mentioned general formula (1), and the substituent that the group may have is also the same. The alkyl group for $R^{203}$ and $R^{204}$ preferably has 2 or more carbon atoms, more preferably 4 or more carbon atoms. Also preferably, the alkyl group has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

$R^{205}$ to $R^{208}$ each independently represent a hydrogen atom or an arbitrary substituent. Not detracting from the advantageous effects of the present invention, $R^{205}$ to $R^{208}$ are not specifically defined, but preferably each is a hydrogen atom, a halogen atom, an alkyl group having from 1 to 20 carbon atoms and optionally having a substituent, an alkoxy group having from 1 to 20 carbon atoms and optionally having a substituent, a group —NHCOR$^{210}$ or a group —NHSO$_2$R$^{212}$, for securing high solubility in solvent and a high absorbance coefficient.

$R^{210}$ and $R^{212}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $R^{205}$ to $R^{208}$, $R^{210}$ and $R^{212}$ has, concretely, the same meaning as that of the alkyl group exemplified for $R^1$ in the above-mentioned general formula (1), and the substituent that the group may have is also the same. The alkyl group for $R^{205}$ to $R^{208}$, $R^{210}$ and $R^{212}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The alkoxy group for $R^{205}$ to $R^{208}$ has the same meaning as that of the alkoxy group exemplified for $R^1$ in the above-mentioned general formula (1), and the substituent that the group may have is also the same. The alkoxy group for $R^{205}$ to $R^{208}$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

Further preferably, $R^{205}$ to $R^{208}$ each are independently an alkyl group having from 1 to 4 carbon atoms such as a methyl group, an ethyl group, a propyl group, an isopropyl group, a cyclopropyl group, a butyl group, an isobutyl group, a sec-butyl group, a tert-butyl group, etc., or a group —NHCOR$^{210}$ or a group —NHSO$_2$R$^{212}$, more preferably a methyl group, a group —NHCOR$^{210}$ or a group —NHSO$_2$R$^{212}$, from the viewpoint of high solubility in solvent and gram absorbance coefficient.

The aryl group for $R^{210}$ and $R^{212}$ has, concretely, the same meaning as that of the aryl group exemplified for $R^{101}$ in the above-mentioned general formula (2), and the substituent that the group may have is also the same as that the aryl group exemplified for $R^{101}$ in the general formula (2) may have.

The heteroaryl group for $R^{210}$ and $R^{212}$ has, concretely, the same meaning as that of the heteroaryl group exemplified for $R^{101}$ in the general formula (2), and the substituent that the group may have is also the same as that the heteroaryl group exemplified for $R^{101}$ in the general formula (2) may have.

Z represents a nitrogen atom or a methine group optionally having a substituent. In case where Z is a methine group, Z may be unsubstituted or may have a substituent. The substituent that Z may have includes an alkyl group having from 1 to 10 carbon atoms and optionally having a substituent, a group —COOR$^{211}$, etc.

$R^{211}$ represents an alkyl group having from 1 to 20 carbon atoms and optionally having a substituent. The alkyl group for $R^{211}$ has, concretely, the same meaning as that of the alkyl group exemplified for $R^1$ in the general formula (1), and the substituent that the group may have is also the same. The alkyl group for $R^{211}$ preferably has 16 or less carbon atoms, more preferably 10 or less carbon atoms, even more preferably 6 or less carbon atoms.

Having a carbon number that falls within the suitable range, the compound could have excellent solubility in solvent and could have a high gram absorbance coefficient.

Z is preferably a nitrogen atom, a methine group, a methine group substituted with an alkyl group having from 1 to 4 carbon atoms, or a methine group substituted with an alkoxycarbonyl group having from 2 to 5 carbon atoms.

Of the compounds represented by the above-mentioned general formula (3), especially preferred are compounds shown in the following Tables 1 to 3.

TABLE 1

| No. | Z | $R^{201}$ | $R^{202}$ | $R^{203}$ |
|---|---|---|---|---|
| 1 | N | CH$_2$CH$_3$ | CN | i-C$_4$H$_9$ |
| 2 | N | CH$_3$ | CN | CH$_2$CH(CH$_2$CH$_3$)CH$_2$CH$_2$CH$_2$CH$_3$ |
| 3 | C—CO$_2$CH$_2$CH$_3$ | CH$_3$ | CO$_2$CH$_2$CH$_3$ | CH$_2$CH(CH$_2$CH$_3$)CH$_2$CH$_2$CH$_2$CH$_3$ |
| 4 | N | CH$_2$CH$_3$ | CN | CH$_2$CH(CH$_2$CH$_3$)CH$_2$CH$_2$CH$_2$CH$_3$ |
| 5 | N | CH$_3$ | CN | CH$_2$CH(CH$_2$CH$_3$)CH$_2$CH$_2$CH$_2$CH$_3$ |
| 6 | C—CO$_2$CH$_2$CH$_3$ | CH$_3$ | CO$_2$CH$_2$CH$_3$ | CH$_2$CH(CH$_2$CH$_3$)CH$_2$CH$_2$CH$_2$CH$_3$ |
| 7 | C—CO$_2$CH$_2$CH$_3$ | CH$_3$ | CO$_2$CH$_2$CH$_3$ | CH$_2$CH(CH$_2$CH$_3$)CH$_2$CH$_2$CH$_2$CH$_3$ |
| 8 | N | CH$_3$ | CN | CH$_2$CH(CH$_2$CH$_3$)CH$_2$CH$_2$CH$_2$CH$_3$ |
| 9 | N | CH$_3$ | CN | CH$_2$CH(CH$_2$CH$_3$)CH$_2$CH$_2$CH$_2$CH$_3$ |
| 10 | N | CH$_2$CH$_3$ | CN | CH$_2$CH(CH$_2$CH$_3$)CH$_2$CH$_2$CH$_2$CH$_3$ |
| 11 | N | CH$_2$CH$_3$ | CN | CH$_2$CH(CH$_2$CH$_3$)CH$_2$CH$_2$CH$_2$CH$_3$ |
| 12 | N | n-C$_4$H$_9$ | CN | i-C$_4$H$_9$ |
| 13 | N | n-C$_4$H$_9$ | CN | CH$_2$CH(CH$_2$CH$_3$)CH$_2$CH$_2$CH$_2$CH$_3$ |
| 14 | N | i-C$_3$H$_7$ | CN | CH$_2$CH(CH$_2$CH$_3$)CH$_2$CH$_2$CH$_2$CH$_3$ |
| 15 | N | CH$_3$ | CN | CH$_2$CH(CH$_2$CH$_3$)CH$_2$CH$_2$CH$_2$CH$_3$ |
| 16 | N | CH$_3$ | CN | CH$_2$CH(CH$_2$CH$_3$)CH$_2$CH$_2$CH$_2$CH$_3$ |
| 17 | N | CH$_3$ | CN | CH$_2$CH(CH$_2$CH$_3$)CH$_2$CH$_2$CH$_2$CH$_3$ |
| 18 | C—CO$_2$CH$_2$CH$_3$ | CH$_3$ | CO$_2$CH$_2$CH$_3$ | i-C$_4$H$_9$ |
| 19 | C—CO$_2$CH$_2$CH$_3$ | CH$_3$ | CN | CH$_2$CH(CH$_2$CH$_3$)CH$_2$CH$_2$CH$_2$CH$_3$ |
| 20 | C—CO$_2$CH$_2$CH$_3$ | CH$_3$ | CN | CH$_2$CH(CH$_2$CH$_3$)CH$_2$CH$_2$CH$_2$CH$_3$ |

| No. | $R^{204}$ | $R^{205}$ | $R^{206}$ | $R^{207}$ | $R^{208}$ |
|---|---|---|---|---|---|
| 1 | i-C$_4$H$_9$ | NHCOCH$_3$ | H | H | H |
| 2 | CH$_2$CH(CH$_2$CH$_3$)CH$_2$CH$_2$CH$_2$CH$_3$ | NHCOCH$_3$ | H | H | H |
| 3 | CH$_2$CH(CH$_2$CH$_3$)CH$_2$CH$_2$CH$_2$CH$_3$ | NHCOCH$_3$ | H | H | H |

TABLE 1-continued

| | | | | | |
|---|---|---|---|---|---|
| 4 | $CH_2CH(CH_2CH_3)CH_2CH_2CH_2CH_3$ | $CH_3$ | H | H | H |
| 5 | $n\text{-}C_8H_{17}$ | $CH_3$ | H | H | H |
| 6 | $CH_2CH(CH_2CH_3)CH_2CH_2CH_2CH_3$ | $CH_3$ | H | H | H |
| 7 | $CH_2CH(CH_2CH_3)CH_2CH_2CH_2CH_3$ | $NHCOCH_2CH_3$ | H | H | H |
| 8 | $CH_2CH(CH_2CH_3)CH_2CH_2CH_2CH_3$ | $CH_2CH_3$ | H | H | H |
| 9 | $CH_2CH(CH_2CH_3)CH_2CH_2CH_2CH_3$ | $NHCOCH_2CH_3$ | H | H | H |
| 10 | $CH_2CH(CH_2CH_3)CH_2CH_2CH_2CH_3$ | $NHCOCH_3$ | H | H | H |
| 11 | $CH_2CH_3$ | $NHCOCH_3$ | H | H | H |
| 12 | $i\text{-}C_4H_9$ | $NHCOCH_3$ | H | H | H |
| 13 | $CH_2CH(CH_2CH_3)CH_2CH_2CH_2CH_3$ | $CH_3$ | H | H | H |
| 14 | $CH_2CH(CH_2CH_3)CH_2CH_2CH_2CH_3$ | $CH_3$ | H | H | H |
| 15 | $CH_2CH(CH_2CH_3)CH_2CH_2CH_2CH_3$ | $i\text{-}C_3H_7$ | H | H | H |
| 16 | $CH_2CH(CH_2CH_3)CH_2CH_2CH_2CH_3$ | $CH_3$ | $OCH_3$ | H | H |
| 17 | $CH_2CH(CH_2CH_3)CH_2CH_2CH_2CH_3$ | H | H | H | H |
| 18 | $i\text{-}C_4H_9$ | $CH_3$ | H | H | H |
| 19 | $CH_2CH(CH_2CH_3)CH_2CH_2CH_2CH_3$ | $CH_3$ | $OCH_3$ | H | H |
| 20 | $CH_2CH(CH_2CH_3)CH_2CH_2CH_2CH_3$ | $CH_2CH_3$ | H | H | H |

TABLE 2

| No. | Z | $R^{201}$ | $R^{202}$ | $R^{203}$ |
|---|---|---|---|---|
| 21 | N | $i\text{-}C_3H_7$ | CN | $i\text{-}C_4H_9$ |
| 22 | N | $CH_3$ | $CO_2CH_3$ | $CH_2CH(CH_2CH_3)CH_2CH_2CH_2CH_3$ |
| 23 | N | $CH_3$ | $CO_2\text{—}n\text{-}C_3H_7$ | $i\text{-}C_4H_9$ |
| 24 | N | $CH_3$ | CN | $(CF_2)_5CF_3$ |
| 25 | N | $CH_3$ | CN | $CH_2CH(CH_2CH_3)CH_2CH_2CH_2CH_3$ |
| 26 | N | $CH_3$ | CN | $i\text{-}C_4H_9$ |
| 27 | N | $CH_3$ | CN | $CH_2CH(CH_2CH_3)CH_2CH_2CH_2CH_3$ |
| 28 | $C\text{—}CO_2CH_3$ | $CH_3$ | $CO_2CH_3$ | $CH_2CH(CH_2CH_3)CH_2CH_2CH_2CH_3$ |
| 29 | $C\text{—}CO_2\text{—}n\text{-}C_4H_9$ | $CH_3$ | $CO_2\text{—}n\text{-}C_4H_9$ | $i\text{-}C_4H_9$ |
| 30 | $C\text{—}CH_3$ | $CH_3$ | $CO_2CH_3$ | $CH_2CH(CH_2CH_3)CH_2CH_2CH_2CH_3$ |
| 31 | $C\text{—}n\text{-}C_4H_9$ | $CH_3$ | $CO_2CH_3$ | $i\text{-}C_4H_9$ |
| 32 | $C\text{—}CO_2\text{—}CH_2CH_3$ | $CH_3$ | CN | $CH_2CH(CH_2CH_3)CH_2CH_2CH_2CH_3$ |
| 33 | $C\text{—}CO_2\text{—}CH_2CH_3$ | $CH_3$ | $CO_2\text{—}CH_2CH_3$ | $CH_2CH(CH_2CH_3)CH_2CH_2CH_2CH_3$ |
| 34 | $C\text{—}CO_2\text{—}CH_2CH_3$ | $CH_3$ | $CO_2\text{—}CH_2CH_3$ | $CH_2CH(CH_2CH_3)CH_2CH_2CH_2CH_3$ |
| 35 | $C\text{—}CO_2\text{—}CH_2CH_3$ | $CH_3$ | CN | $CH_2CH(CH_2CH_3)CH_2CH_2CH_2CH_3$ |
| 36 | $C\text{—}CN$ | $CH_3$ | CN | $CH_2CH(CH_2CH_3)CH_2CH_2CH_2CH_3$ |
| 37 | $C\text{—}CN$ | $CH_3$ | CN | $CH_2CH(CH_2CH_3)CH_2CH_2CH_2CH_3$ |
| 38 | N | $CH_3$ | CN | $CH_2CH(CH_2CH_3)CH_2CH_2CH_2CH_3$ |
| 39 | N | $CH_3$ | CN | $CH_2CH(CH_2CH_3)CH_2CH_2CH_2CH_3$ |
| 40 | $C\text{—}CO_2CH_3$ | $CH_3$ | $CO_2CH_3$ | $CH_2CH(CH_2CH_3)CH_2CH_2CH_2CH_3$ |

| No. | $R^{204}$ | $R^{205}$ | $R^{206}$ | $R^{207}$ | $R^{208}$ |
|---|---|---|---|---|---|
| 21 | $i\text{-}C_4H_9$ | H | $NHCOCH_3$ | H | H |
| 22 | $CH_2CH(CH_2CH_3)CH_2CH_2CH_2CH_3$ | $NHCOCH_3$ | H | H | H |
| 23 | $i\text{-}C_4H_9$ | $NHCOCH_3$ | H | H | H |
| 24 | $(CF_2)_5CF_3$ | $NHCOCH_3$ | H | H | H |
| 25 | $CH_2CH(CH_2CH_3)CH_2CH_2CH_2CH_3$ | $NHCOPh$ | H | H | H |
| 26 | $i\text{-}C_4H_9$ | $NHCO\text{-}i\text{-}C_4H_9$ | H | H | H |
| 27 | $CH_2CH(CH_2CH_3)CH_2CH_2CH_2CH_3$ | $NHCOCH_3$ | $OCH_3$ | H | H |
| 28 | $CH_2CH(CH_2CH_3)CH_2CH_2CH_2CH_3$ | Cl | H | $CH_3$ | H |
| 29 | $i\text{-}C_4H_9$ | $NHCOCH_3$ | $CH_3$ | H | H |
| 30 | $CH_2CH(CH_2CH_3)CH_2CH_2CH_2CH_3$ | $CH_3$ | H | $OCH_3$ | H |
| 31 | $i\text{-}C_4H_9$ | $NHCO\text{-}i\text{-}C_4H_9$ | H | H | H |
| 32 | $CH_2CH(CH_2CH_3)CH_2CH_2CH_2CH_3$ | $NHCOCH_3$ | H | H | H |
| 33 | $CH_2CH(CH_2CH_3)CH_2CH_2CH_2CH_3$ | $NHCOCH_3$ | $OCH_3$ | H | H |
| 34 | $CH_2CH(CH_2CH_3)CH_2CH_2CH_2CH_3$ | $CH_3$ | $OCH_3$ | H | H |
| 35 | $CH_2CH(CH_2CH_3)CH_2CH_2CH_2CH_3$ | $CH_3$ | H | H | H |
| 36 | $CH_2CH(CH_2CH_3)CH_2CH_2CH_2CH_3$ | $NHCOCH_3$ | H | H | H |
| 37 | $CH_2CH(CH_2CH_3)CH_2CH_2CH_2CH_3$ | $CH_3$ | H | H | H |
| 38 | $CH_2CH(CH_2CH_3)CH_2CH_2CH_2CH_3$ | $NHCOCH_3$ | Cl | H | H |
| 39 | $CH_2CH(CH_2CH_3)CH_2CH_2CH_2CH_3$ | F | H | H | H |
| 40 | $CH_2CH(CH_2CH_3)CH_2CH_2CH_2CH_3$ | Cl | $CH_3$ | H | H |

TABLE 3

| No. | Z | $R^{201}$ | $R^{202}$ | $R^{203}$ |
|---|---|---|---|---|
| 41 | N | $n\text{-}C_6H_{13}$ | $CO_2\text{—}n\text{-}C_4H_9$ | $n\text{-}C_6H_{13}$ |
| 42 | N | $CH_2OCH_2CH_3$ | $CO_2CF_3$ | $CH_2OCH_2CH_3$ |
| 43 | N | $CF_3$ | $CO_2\text{—}Ph$ | $CF_3$ |
| 44 | N | $CF_2CF_3$ | $CO_2CH_2\text{—}Ph$ | $CF_2CF_3$ |
| 45 | N | Ph | $CO_2CH_2\text{-cyclohexane}$ | Ph |

TABLE 3-continued

| | No. | | | | |
|---|---|---|---|---|---|
| 46 | N | CH$_2$—Ph | CO$_2$CH$_2$CH$_2$OCH$_3$ | CH$_2$—Ph | |
| 47 | N | CH$_2$CH$_2$O—Ph | CO$_2$—n-C$_8$H$_{17}$ | CH$_2$CH$_2$O—Ph | |
| 48 | N | CH$_2$-cyclohexane | CO$_2$CH$_2$CH$_2$CH$_2$CF$_3$ | CH$_2$-cyclohexane | |
| 49 | N | n-C$_8$H$_{17}$ | CO$_2$CH$_2$CH$_2$CH$_2$CN | n-C$_8$H$_{17}$ | |
| 50 | N | CH$_3$ | CN | CH$_2$CH(CH$_2$CH$_3$)CH$_2$CH$_2$CH$_2$CH$_3$ | |
| 51 | C—CO$_2$Ph | n-C$_6$H$_{13}$ | CO$_2$—n-C$_4$H$_9$ | n-C$_6$H$_{13}$ | |
| 52 | C—CO$_2$CH$_2$Ph | CH$_2$OCH$_2$CH$_3$ | CO$_2$CF$_3$ | CH$_2$OCH$_2$CH$_3$ | |
| 53 | C—CO$_2$—n-C$_8$H$_{17}$ | CF$_3$ | CO$_2$—Ph | CF$_3$ | |
| 54 | C—CO$_2$—n-C$_6$H$_{13}$ | CF$_2$CF$_3$ | CO$_2$CH$_2$—Ph | CF$_2$CF$_3$ | |
| 55 | C—CO$_2$-cyclohexyl | Ph | CO$_2$CH$_2$-cyclohexanel | Ph | |
| 56 | C—CN | CH$_2$—Ph | CO$_2$CH$_2$CH$_2$OCH$_3$ | CH$_2$—Ph | |
| 57 | C—CN | CH$_2$CH$_2$O—Ph | CO$_2$—n-C$_8$H$_{17}$ | CH$_2$CH$_2$O—Ph | |
| 58 | C—CN | CH$_2$-cyclohexane | CO$_2$CH$_2$CH$_2$CH$_2$CF$_3$ | CH$_2$-cyclohexane | |
| 59 | C—CN | n-C$_8$H$_{17}$ | CO$_2$CH$_2$CH$_2$CH$_2$CN | n-C$_8$H$_{17}$ | |
| 60 | C—CN | CH$_2$CH$_2$CH$_2$CF$_3$ | CO$_2$CH$_2$(CH$_3$)CH$_2$CH$_3$ | CH$_2$CH$_2$CH$_2$CF$_3$ | |

| No. | $R^{204}$ | $R^{205}$ | $R^{206}$ | $R^{207}$ | $R^{208}$ |
|---|---|---|---|---|---|
| 41 | n-C$_6$H$_{13}$ | O—n-Bu | H | H | H |
| 42 | CH$_2$OCH$_2$CH$_3$ | CF$_3$ | H | H | H |
| 43 | CF$_3$ | NHSO$_2$CF$_3$ | H | H | H |
| 44 | CF$_2$CF$_3$ | NHSO$_2$—n-Bu | H | H | H |
| 45 | Ph | Br | H | H | H |
| 46 | CH$_2$—Ph | H | O—n-C$_6$H$_{13}$ | H | H |
| 47 | CH$_2$CH$_2$O—Ph | H | CF$_2$CF$_2$CF$_2$CF$_3$ | H | H |
| 48 | CH$_2$-cyclohexane | H | NHSO$_2$CH$_2$—Ph | H | H |
| 49 | n-C$_8$H$_{17}$ | H | NHSO$_2$—Ph | H | H |
| 50 | CH$_2$CH(CH$_2$CH$_3$)CH$_2$CH$_2$CH$_2$CH$_3$ | NHSO$_2$—n-Bu | H | H | H |
| 51 | n-C$_6$H$_{13}$ | O—n-Bu | H | H | H |
| 52 | CH$_2$OCH$_2$CH$_3$ | CF$_3$ | H | H | H |
| 53 | CF$_3$ | NHSO$_2$CF$_3$ | H | H | H |
| 54 | CF$_2$CF$_3$ | NHSO$_2$—n-Bu | H | H | H |
| 55 | Ph | Br | H | H | H |
| 56 | CH$_2$—Ph | H | O—n-C$_6$H$_{13}$ | H | H |
| 57 | CH$_2$CH$_2$O—Ph | H | CF$_2$CF$_2$CF$_2$CF$_3$ | H | H |
| 58 | CH$_2$-cyclohexane | H | NHSO$_2$CH$_2$—Ph | H | H |
| 59 | n-C$_8$H$_{17}$ | H | NHSO$_2$—Ph | H | H |
| 60 | CH$_2$CH$_2$CH$_2$CF$_3$ | Me | H | Me | H |

The compounds represented by the above-mentioned general formula (3) can be synthesized, for example, according to the method described in JP-T 8-505820.

As the heterocyclic compound, there are mentioned compounds represented by the following general formula (4).

[Chem. 17]

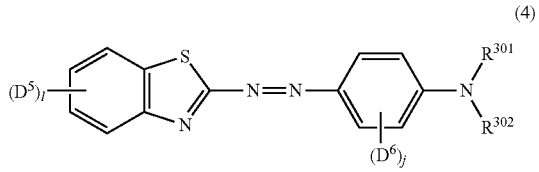

(4)

[In the general formula (4), $R^{301}$, $R^{302}$, $D^5$ and $D^6$ each independently represent an arbitrary substituent; l indicates an integer of from 0 to 4, and when l is 2 or more, two or more $D^5$s in one molecule may be the same or different; j indicates an integer of from 0 to 4, and when j is 2 or more, two or more $D^6$s in one molecule may be the same or different.]

$R^{301}$ and $R^{302}$ each independently represent an arbitrary substituent. Not detracting from the advantageous effects of the present invention, $R^{301}$ and $R^{302}$ are not specifically defined, but preferably, each is independently an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent, for securing a high absorbance coefficient and high solubility in solvent.

Concretely, the alkyl group for $R^{301}$ and $R^{302}$ has the same meaning as that of the alkyl group exemplified for $R^1$ in the above-mentioned general formula (1), and the substituent that the group may have is also the same. The alkyl group for $R^{301}$ and $R^{302}$ preferably has 2 or more carbon atoms, more preferably 4 or more carbon atoms. Also preferably, the group has 16 or less carbon atoms, more preferably 12 or less carbon atoms. Having a carbon number that falls within the suitable range, the compound could have excellent solubility in solvent and could have a high gram absorbance coefficient.

The aryl group for $R^{301}$ and $R^{302}$ has, concretely, the same meaning as that of the aryl group exemplified for $R^{101}$ in the above-mentioned general formula (2), and the substituent that the group may have is also the same as that of the aryl group exemplified for $R^{101}$ in the general formula (2).

The heteroaryl group for $R^{301}$ and $R^{302}$ has, concretely, the same meaning as that of the heteroaryl group exemplified for $R^{101}$ in the above-mentioned general formula (2), and the substituent that the group may have is also the same as that of the heteroaryl group exemplified for $R^{101}$ in the general formula (2).

$D^5$ represents an arbitrary substituent. Not detracting from the advantageous effects of the present invention, $D^5$ is not specifically defined, but is preferably a halogen atom, a cyano group, an alkyl group having from 1 to 20 carbon atoms and optionally having a substituent, an alkoxy group having from 1 to 20 carbon atoms and optionally having a substituent, a group —SCN, a group —COOR$^{303}$, a group —COR$^{306}$ or a group —OCOR$^{307}$, for securing a high absorbance coefficient and high solubility in solvent 1 indicates an integer of from 0 to 4, and when l is 2 or more, two or more $D^5$s existing in one molecule may be the same or different.

$R^{303}$, $R^{306}$ and $R^{307}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $D^5$, $R^{303}$, $R^{306}$ and $R^{307}$ has, concretely, the same meaning as that of the alkyl group exemplified for $R^1$ in the above-mentioned general formula (1), and the substituent that the group may have is also the same. The alkyl group for $D^5$, $R^{303}$, $R^{306}$ and $R^{307}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The alkoxy group for $D^5$ has the same meaning as that of the alkoxy group exemplified for $R^1$ in the above-mentioned general formula (1), and the substituent that the group may have is also the same. The alkoxy group for $D^5$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $R^{303}$, $R^{306}$ and $R^{307}$ has, concretely, the same meaning as that of the aryl group exemplified for $R^{101}$ in the above-mentioned general formula (2), and the substituent that the group may have is also the same as that the aryl group exemplified for $R^{101}$ in the general formula (2) may have.

The heteroaryl group for $R^{303}$, $R^{306}$ and $R^{307}$ has, concretely, the same meaning as that of the heteroaryl group exemplified for $R^{101}$ in the above-mentioned formula (2), and the substituent that the group may have is also the same as that the heteroaryl group exemplified for $R^{101}$ in the general formula (2) may have.

$D^6$ represents an arbitrary substituent. Not detracting from the advantageous effects of the present invention, $D^6$ is not specifically defined, but is preferably an alkyl group having from 1 to 20 carbon atoms and optionally having a substituent, an alkoxy group having from 1 to 20 carbon atoms and optionally having a substituent, a group —NHCOR$^{304}$ or a group —NHSO$_2$R$^{305}$, for securing a high absorbance coefficient and high solubility in solvent j indicates an integer of from 0 to 4, and when j is 2 or more, two or more $D^6$s existing in one molecule may be the same or different.

$R^{304}$ and $R^{305}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $D^6$, $R^{304}$ and $R^{305}$ has, concretely, the same meaning as that of the alkyl group exemplified for $R^1$ in the above-mentioned general formula (1), and the substituent that the group may have is also the same. The alkyl group for $D^6$, $R^{304}$ and $R^{305}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The alkoxy group for $D^6$ has the same meaning as that of the alkoxy group exemplified for $R^1$ in the above-mentioned general formula (1), and the substituent that the group may have is also the same. The alkoxy group for $D^6$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $R^{304}$ and $R^{305}$ has, concretely, the same meaning as that of the aryl group exemplified for $R^{101}$ in the above-mentioned general formula (2), and the substituent that the group may have is also the same as that the aryl group exemplified for $R^{101}$ in the general formula (2) may have.

The heteroaryl group for $R^{304}$ and $R^{305}$ has, concretely, the same meaning as that of the heteroaryl group exemplified for $R^{101}$ in the above-mentioned general formula (2), and the substituent that the group may have is also the same as that the heteroaryl group exemplified for $R^{101}$ in the general formula (2) may have.

Specific examples of the compounds represented by the above-mentioned general formula (4) are shown below; however, not overstepping the scope and the spirit thereof, the present invention is not limited to these.

[Chem. 18]

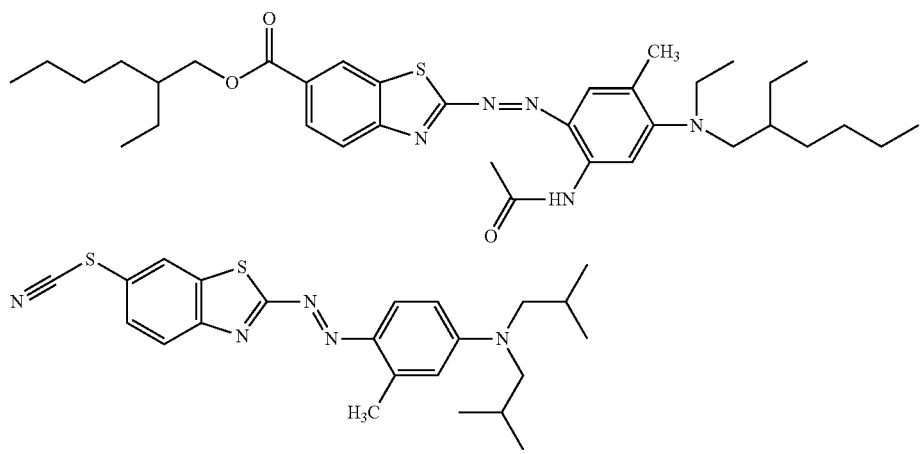

-continued
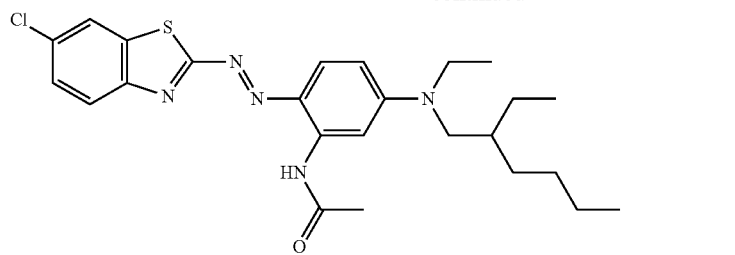
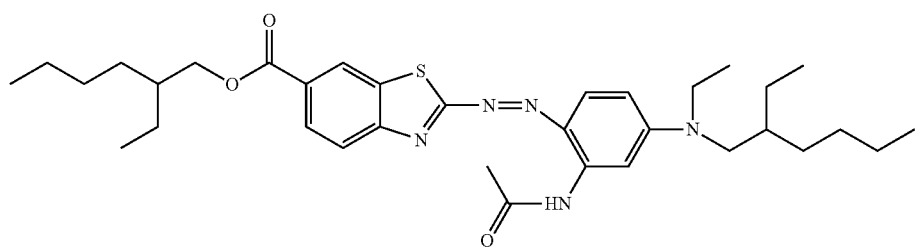
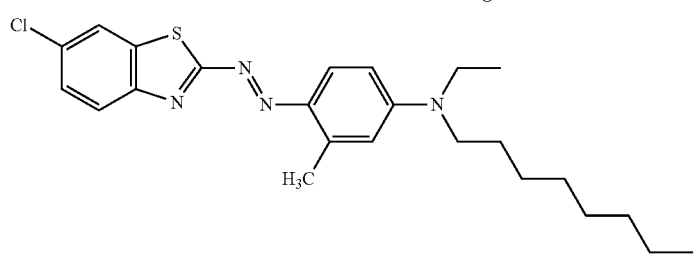
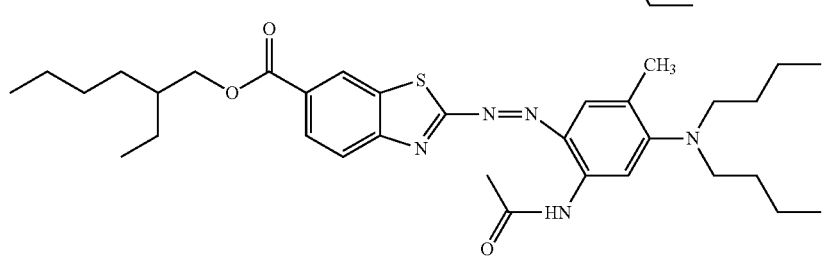
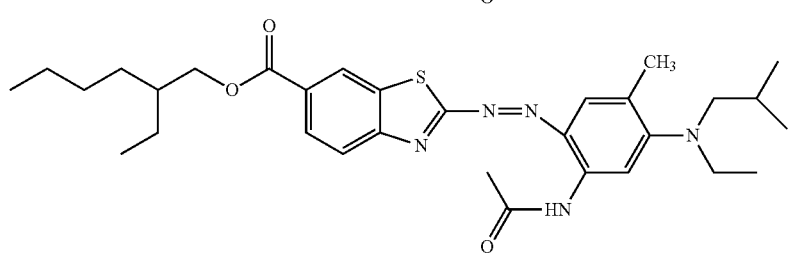
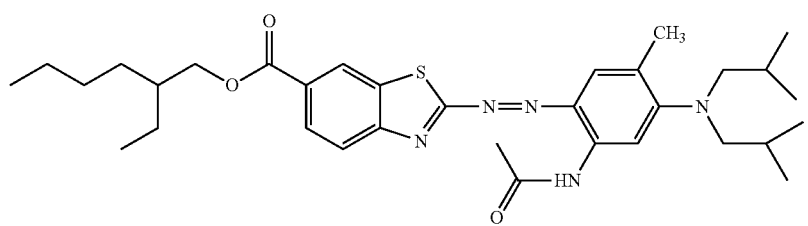
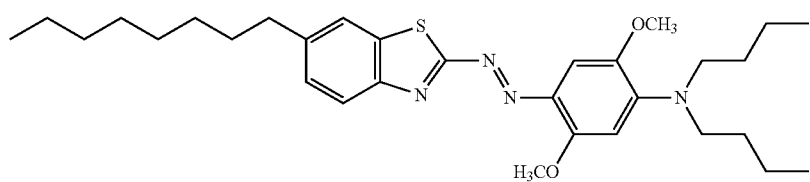

-continued
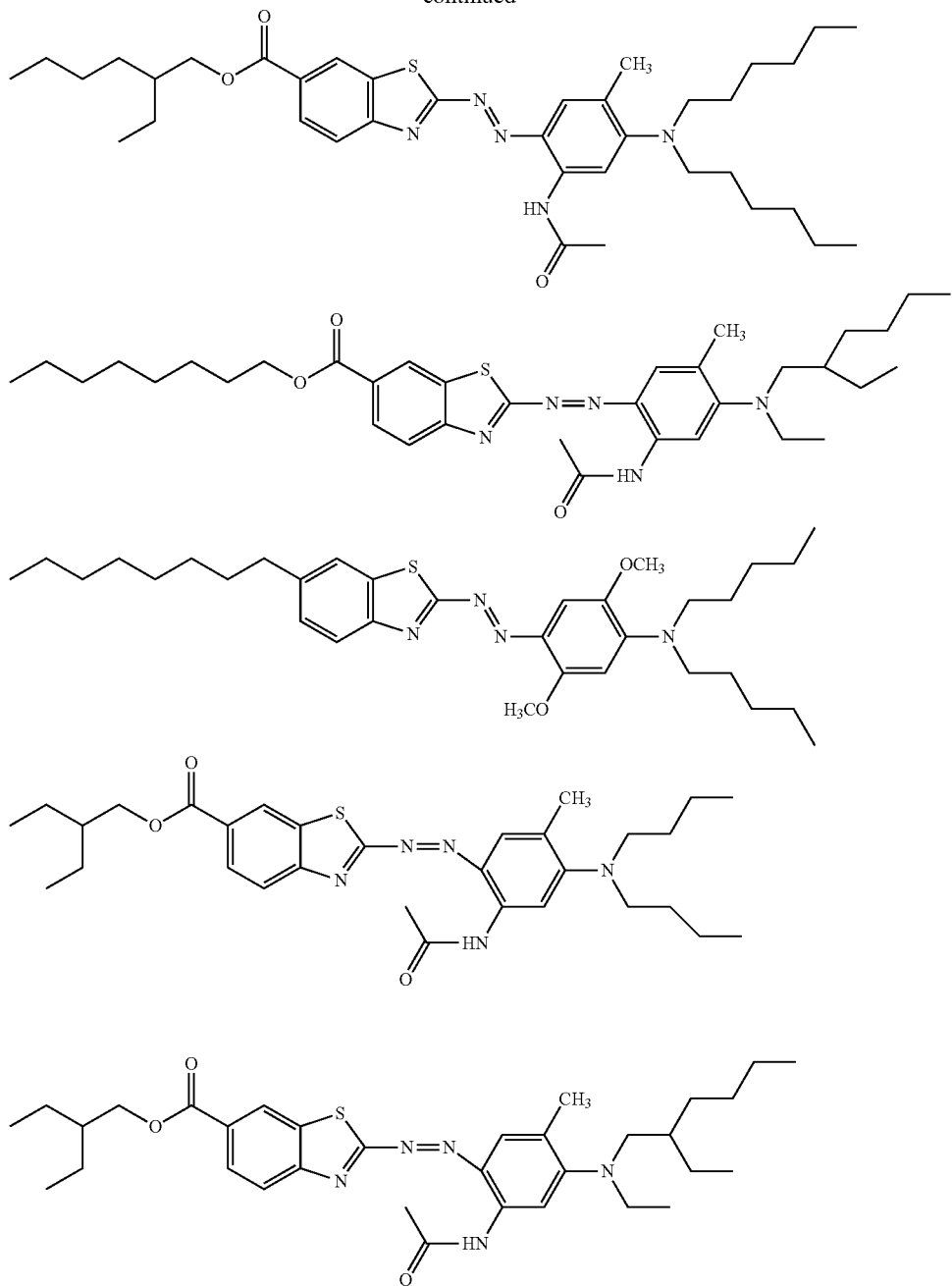
[Chem 19]
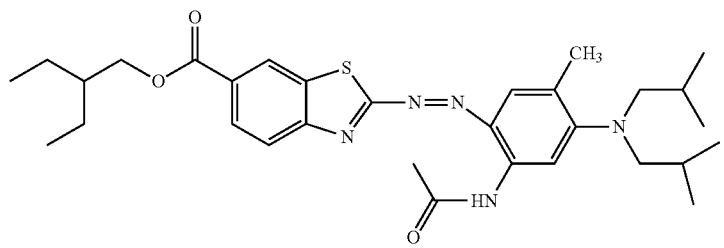

-continued
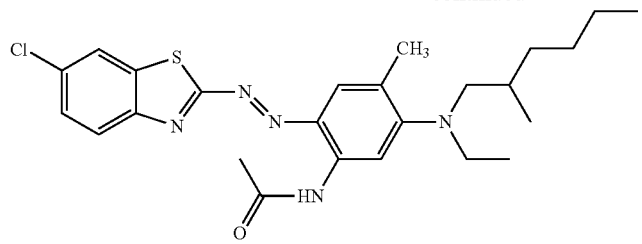
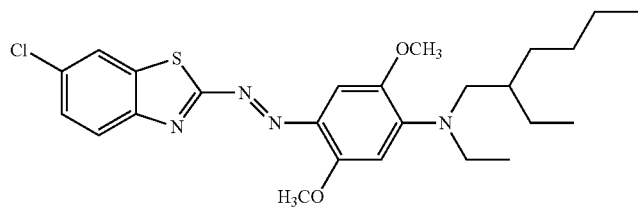
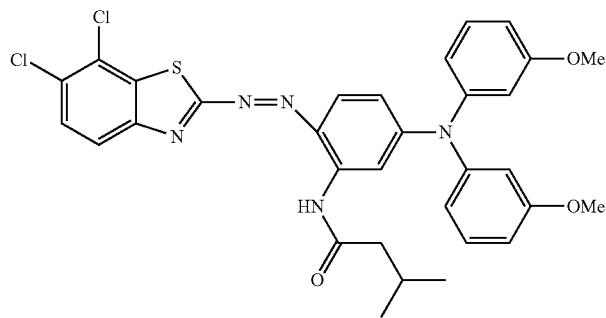
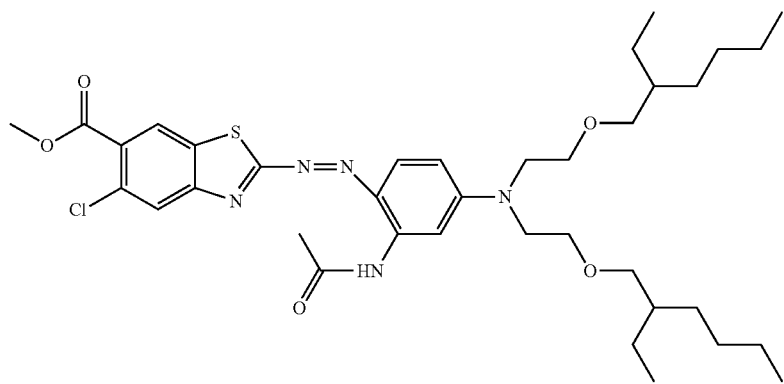
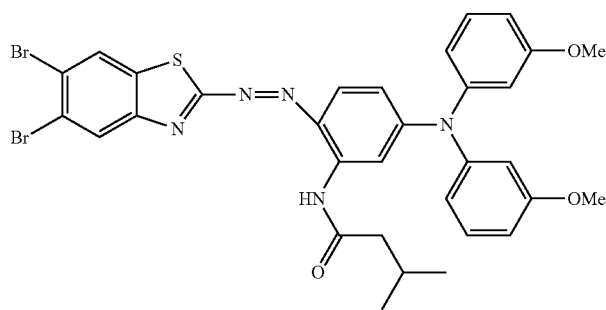

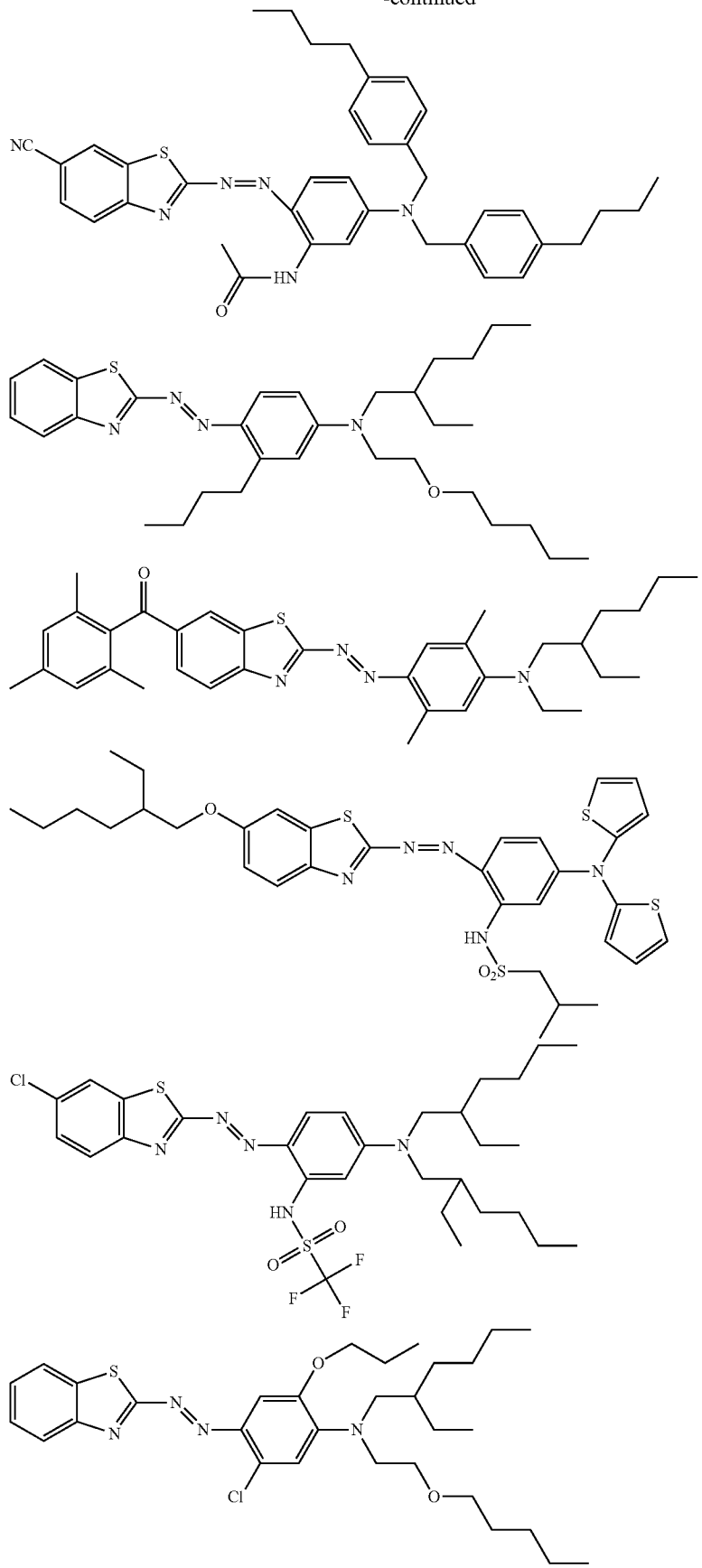

-continued

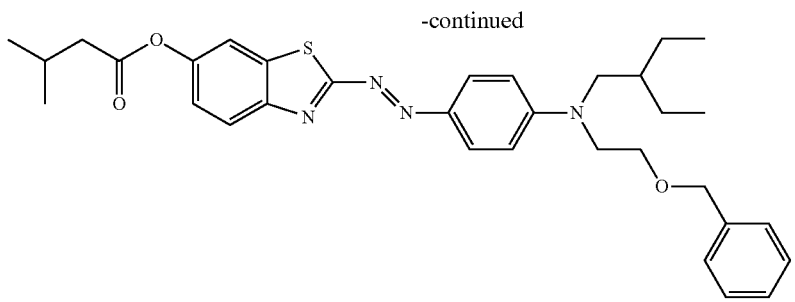

The heterocyclic compounds represented by the above-mentioned general formula (4) can be synthesized, for example, according to the method described in JP-A 10-204307 and 2000-280635.

As the other heterocyclic compounds, there are mentioned compounds represented by the following general formula (5).

[Chem. 20]

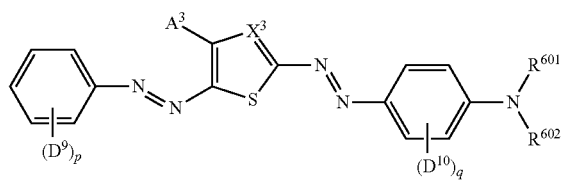

(5)

[In the general formula (5), $R^{601}$, $R^{602}$, $D^9$ and $D^{10}$ each independently represent an arbitrary substituent; $A^3$ represents a hydrogen atom or an arbitrary substituent; p indicates an integer of from 0 to 5, and when p is 2 or more, two or more $D^9$s in one molecule may be the same or different; q indicates an integer of from 0 to 4, and when q is 2 or more, two or more $D^{10}$s in one molecule may be the same or different; $X^3$ represents a nitrogen atom, or a methine group optionally having a halogen atom, a cyano group or a group —COOR$^{605}$ as a substituent; $R^{605}$ represents a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.]

$R^{600}$ and $R^{602}$ each independently represent an arbitrary substituent. Not detracting from the advantageous effects of the present invention, $R^{601}$ and $R^{602}$ are not specifically defined, but preferably, each is independently an alkyl group having from 1 to 20 carbon atoms and optionally having a substituent. Concretely, the alkyl group has the same meaning as that of the alkyl group exemplified for $R^1$ in the general formula (1), and the substituent that the group may have is also the same.

The alkyl group for $R^{601}$ and $R^{602}$ preferably has 4 or more carbon atoms, more preferably 5 or more carbon atoms. Also preferably, the group has 16 or less carbon atoms, more preferably 12 or less carbon atoms. Having a carbon number that falls within the suitable range, the compound could have excellent solubility in solvent and could have a high gram absorbance coefficient.

Preferably, at least one of $R^{601}$ and $R^{602}$ is a branched alkyl group, and more preferably at least one of these is a branched alkyl group having from 5 to 20 carbon atoms. Even more preferably, both of $R^{601}$ and $R^{602}$ are branched alkyl groups.

$D^9$ represents an arbitrary substituent. Not detracting from the advantageous effects of the present invention, $D^9$ is not specifically defined, but is preferably a halogen atom, a cyano group, an alkyl group having from 1 to 20 carbon atoms and optionally having a substituent, an alkoxy group having from 1 to 20 carbon atoms and optionally having a substituent, a group —COOR$^6$, a group —COR$^{609}$, a group —OCOR$^{610}$ or the like since the compound could have excellent solubility in solvent and could have a high gram absorbance coefficient.

p indicates an integer of from 0 to 5, and when p is 2 or more, two or more $D^9$s existing in one molecule may be the same or different.

$R^{604}$, $R^{609}$ and $R^{610}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

$D^{10}$ represents an arbitrary substituent. Not detracting from the advantageous effects of the present invention, $D^{10}$ is not specifically defined, but is preferably a halogen atom, an alkyl group having from 1 to 20 carbon atoms and optionally having a substituent, an alkoxy group having from 1 to 20 carbon atoms and optionally having a substituent, a group —NHCOR$^{603}$, a group —NHSO$_2$R$^{608}$ or the like since the compound could have excellent solubility in solvent and could have a high gram absorbance coefficient.

q indicates an integer of from 0 to 5, and when q is 2 or more, two or more $D^{10}$s existing in one molecule may be the same or different.

$R^{603}$ and $R^{608}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $D^9$, $R^{604}$, $R^{609}$, $R^{610}$, $D^{10}$, $R^{603}$ and $R^{608}$ has, concretely, the same meaning as that of the alkyl group exemplified for $R^1$ in the above-mentioned general formula (1), and the substituent that the group may have is also the same.

The alkyl group for $D^9$, $R^{604}$, $R^{609}$, $R^{610}$, $D^{10}$, $R^{603}$ and $R^{608}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The alkoxy group for $D^9$ and $D^{10}$ has the same meaning as that of the alkoxy group exemplified for $R^1$ in the above-mentioned general formula (1), and the substituent that the group may have is also the same. The alkoxy group for $D^9$ and $D^{10}$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $R^{604}$, $R^{609}$, $R^{610}$, $R^{603}$ and $R^{608}$ has, concretely, the same meaning as that of the aryl group exemplified for $R^{101}$ in the above-mentioned general formula (2), and the substituent that the group may have is also the same.

The heteroaryl group for $R^{604}$, $R^{609}$, $R^{610}$, $R^{603}$ and $R^{608}$ has, concretely, the same meaning as that of the heteroaryl group exemplified for $R^{101}$ in the above-mentioned general formula (2), and the substituent that the group may have is also the same.

$A^3$ represents a hydrogen atom or an arbitrary substituent. Not detracting from the advantageous effects of the present invention, $A^3$ is not specifically defined, but represents a hydrogen atom, an alkoxy group optionally having a substituent, a halogen atom, a cyano group, an aryl group having from 6 to 20 carbon atoms and optionally having a substituent, a heteroaryl group having from 2 to 20 carbon atoms and optionally having a substituent, an alkoxy group having from 1 to 20 carbon atoms and optionally having a substituent, or a group —$COOR^{606}$; $R^{606}$ represents a hydrogen atom, an alkyl group having from 1 to 20 carbon atoms and optionally having a substituent, an aryl group having from 6 to 20 carbon atoms and optionally having a substituent, and a heteroaryl group having from 2 to 20 carbon atoms and optionally having a substituent.

The alkoxy group for $A^3$ has the same meaning as that of the alkoxy group exemplified for $R^1$ in the above-mentioned general formula (1), and the substituent that the group may have is also the same. The alkoxy group for $A^1$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $A^3$ and $R^{606}$ has, concretely, the same meaning as that of the aryl group exemplified for $R^{101}$ in the above-mentioned general formula (2), and the substituent that the group may have is also the same.

The aryl group for $A^3$ is preferably a phenyl group or a naphthyl group optionally having a substituent, from the viewpoint of high solubility of the compound in solvent. The substituent that the phenyl group or the naphthyl group may have is preferably a halogen atom, an alkyl group having from 1 to 10 carbon atoms or an alkoxy group having from 1 to 10 carbon atoms, from the viewpoint of high solubility of the compound in solvent.

The heteroaryl group for $A^3$ and $R^{606}$ has, concretely, the same meaning as that of the heteroaryl group exemplified for $R^{101}$ in the above-mentioned general formula (2), and the substituent that the group may have is also the same.

The heteroaryl group for $A^3$ is preferably a thienyl group optionally having a substituent from the viewpoint of high solubility of the compound in solvent. The substituent that the thienyl group may have is preferably a halogen atom, an alkyl group having from 1 to 10 carbon atoms or an alkoxy group having from 1 to 10 carbon atoms, from the viewpoint of high solubility of the compound in solvent.

The alkyl group for $A^3$ and $R^{606}$ has, concretely, the same meaning as that of the alkyl group exemplified for $R^1$ in the above-mentioned general formula (1), and the substituent that the group may have is also the same. The alkyl group for $A^3$ and $R^{606}$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

$X^3$ represents a nitrogen atom, or a methine group optionally having a halogen atom, a cyano group or a group —$COOR^{605}$ as a substituent; $R^{605}$ represents a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $R^{605}$ has, concretely the same meaning as that of the alkyl group exemplified for $R^1$ in the above-mentioned general formula (1), and the substituent that the group may have is also the same. The alkyl group for $R^{605}$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $R^{605}$ has, concretely the same meaning as that of the aryl group exemplified for $R^{101}$ in the above-mentioned general formula (2), and the substituent that the group may have is also the same.

The heteroaryl group for $R^{605}$ has, concretely, the same meaning as that of the heteroaryl group exemplified for $R^{101}$ in the above-mentioned general formula (2), and the substituent that the group may have is also the same.

Specific examples of the compounds represented by the above-mentioned general formula (5) are shown below; however, not overstepping the scope and the spirit thereof, the present invention is not limited to these.

[Chem. 21]

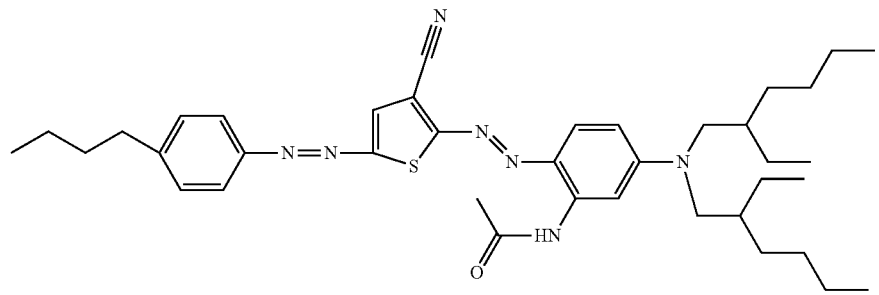

-continued
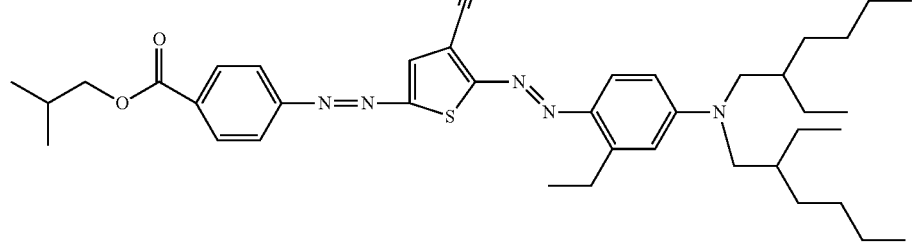
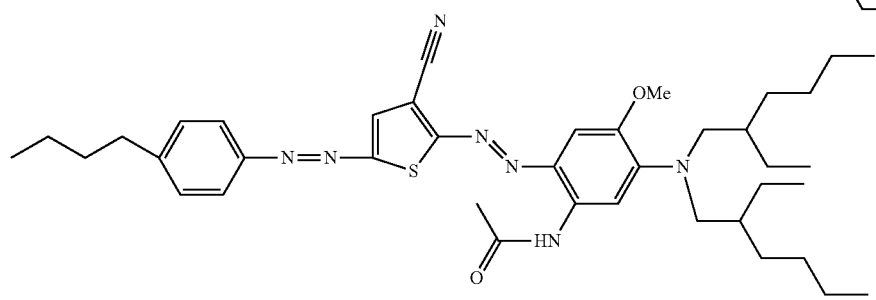
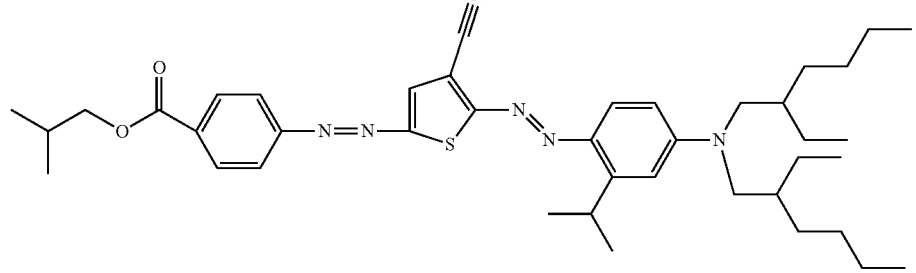
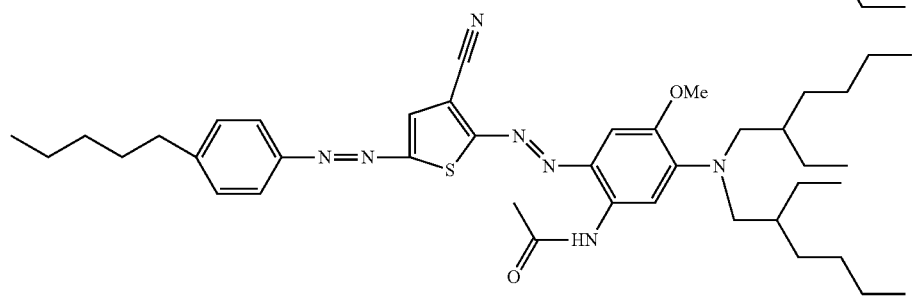
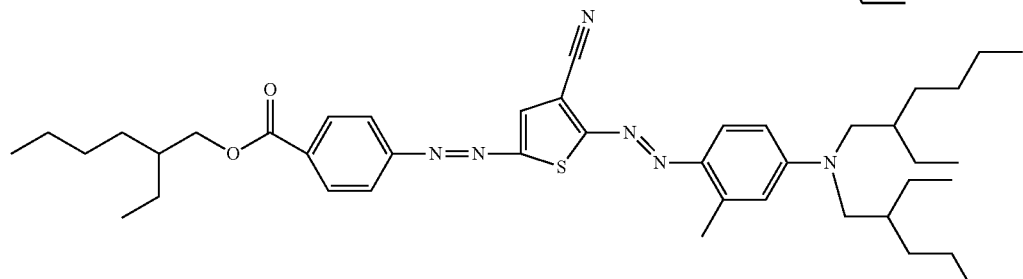
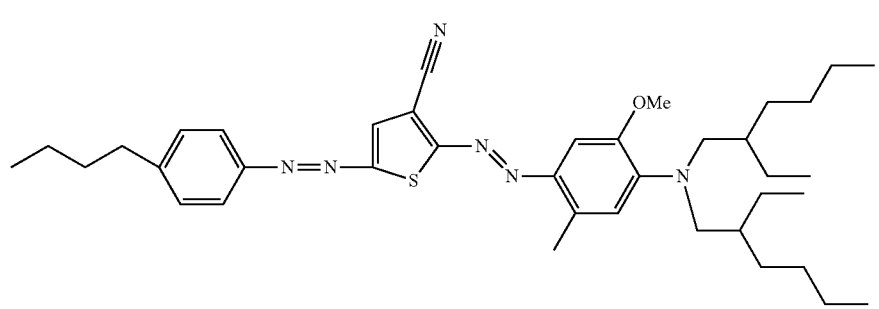

-continued
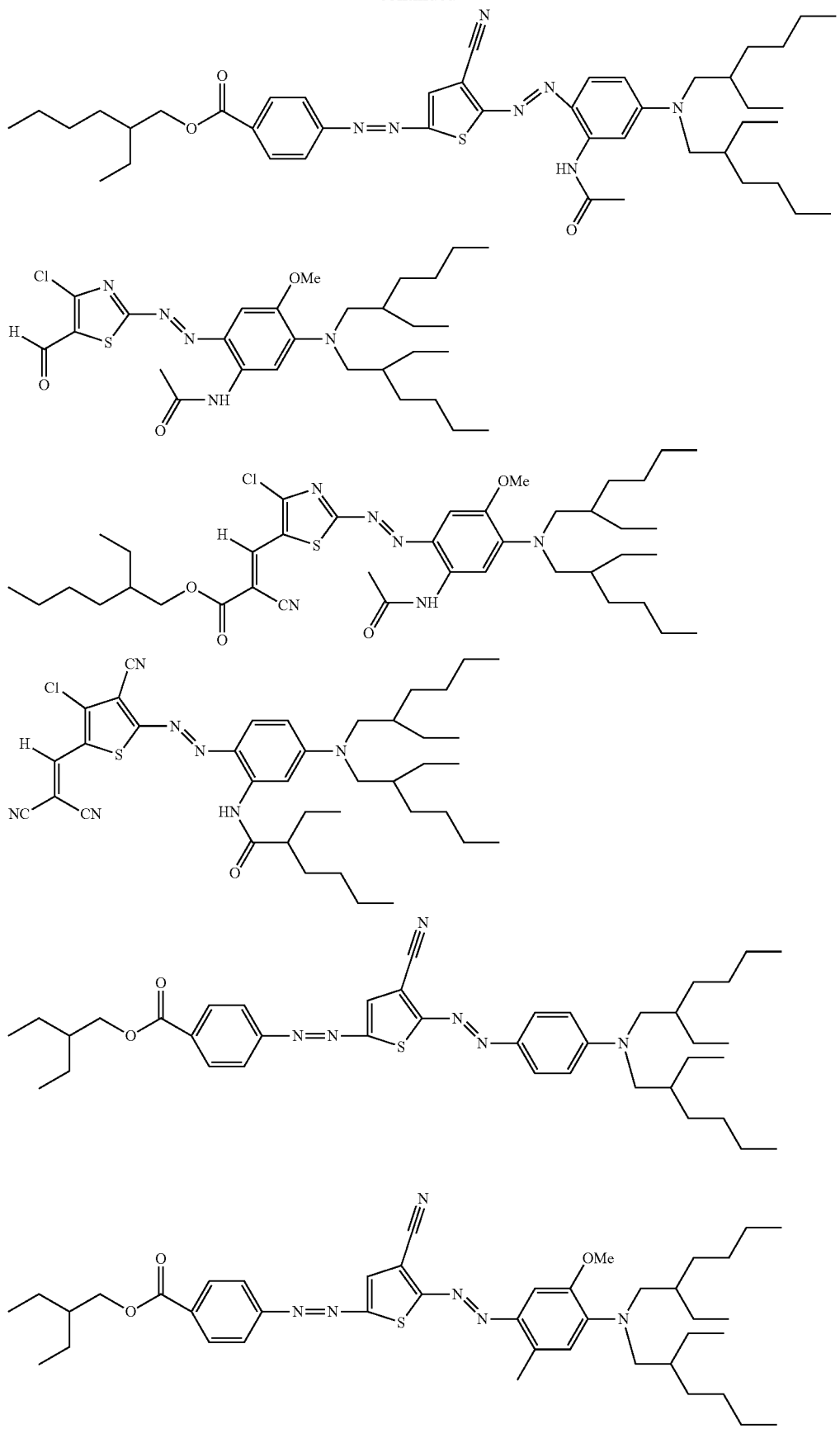

-continued
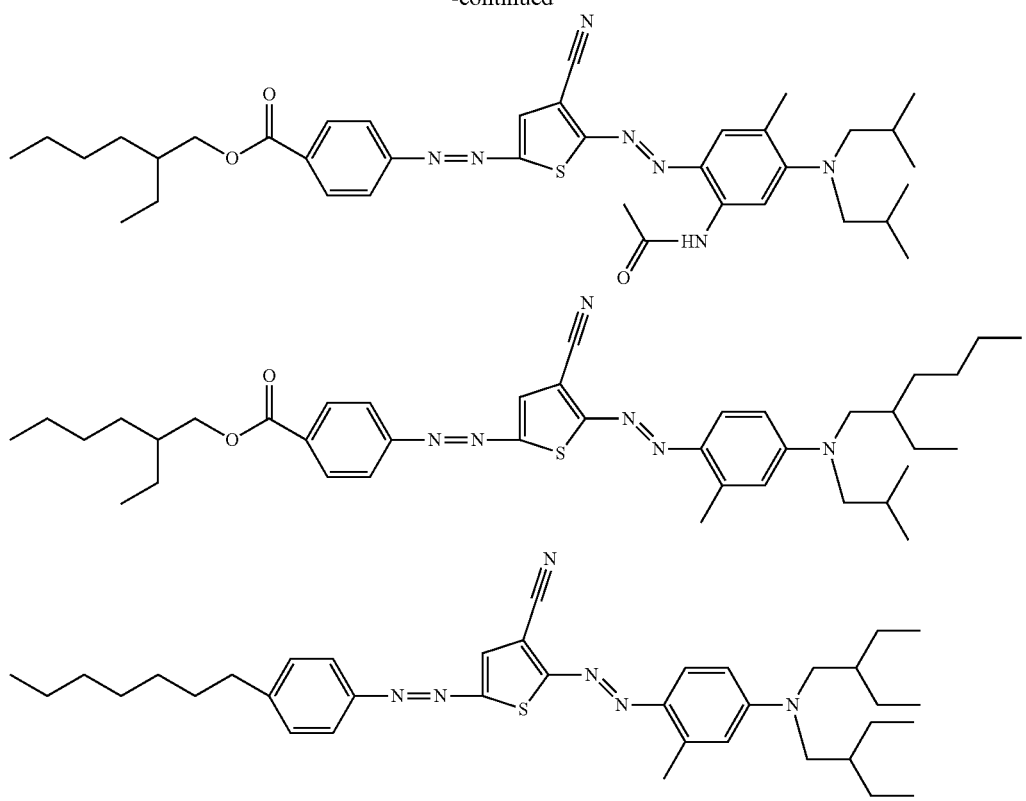
[Chem. 22]
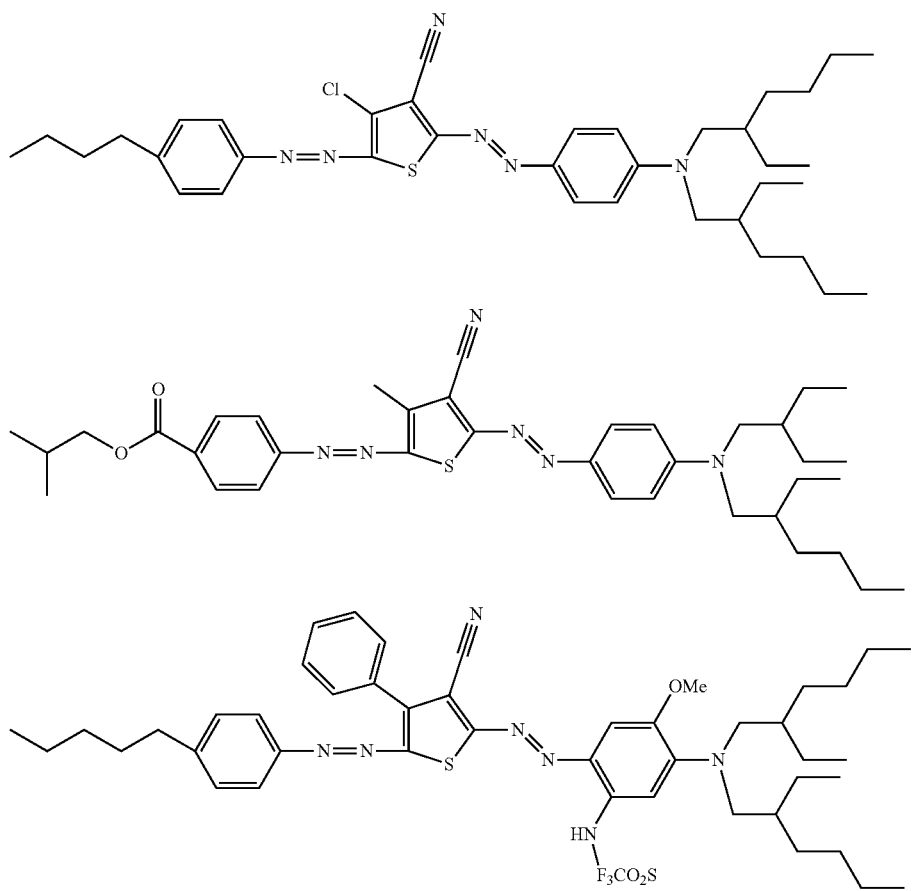

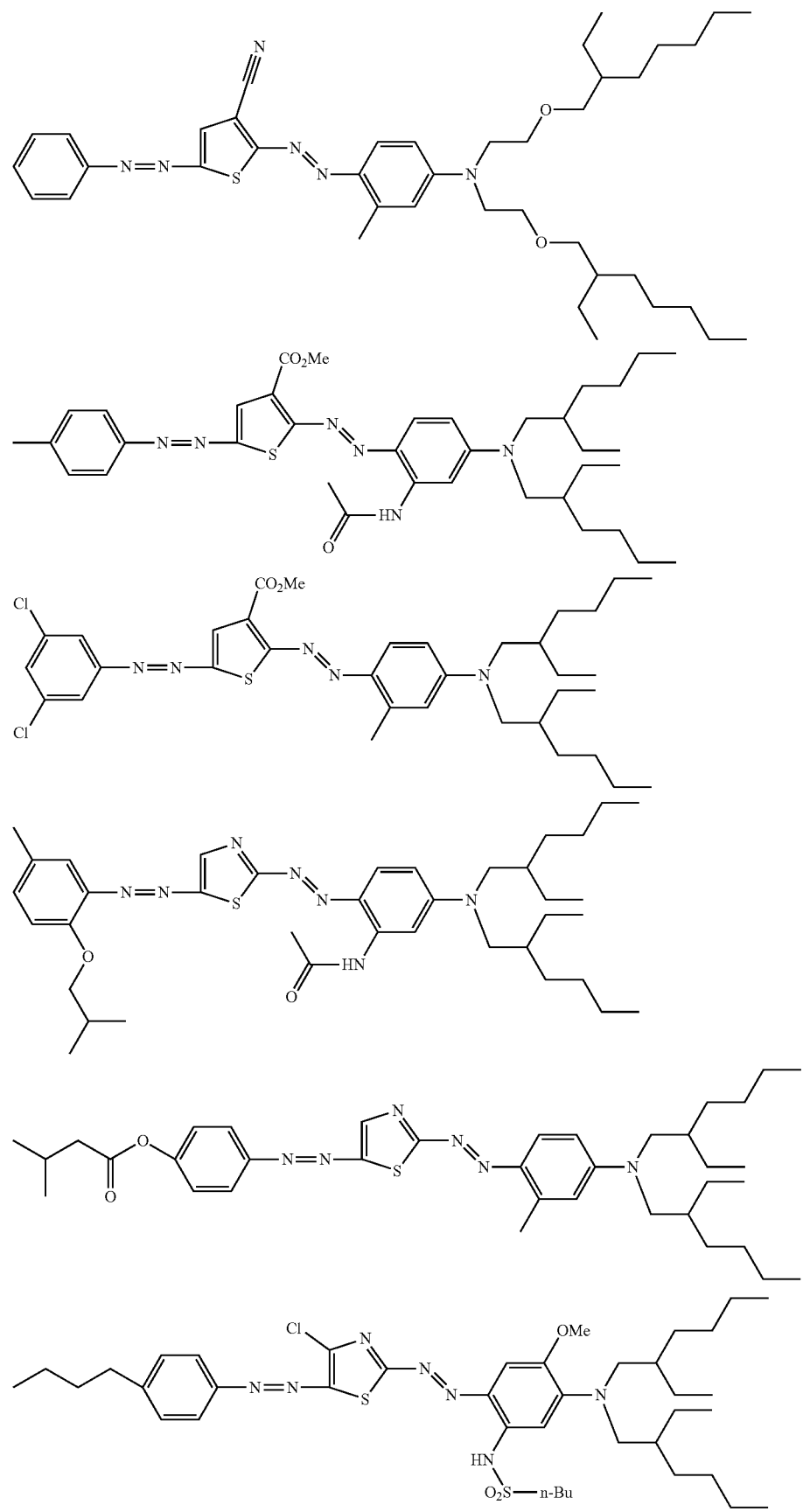

-continued
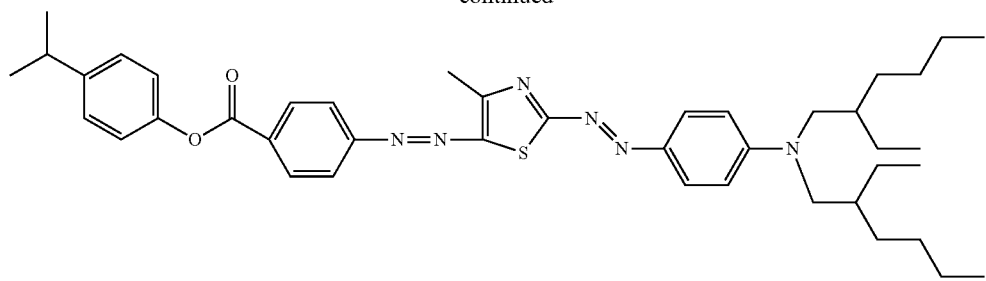
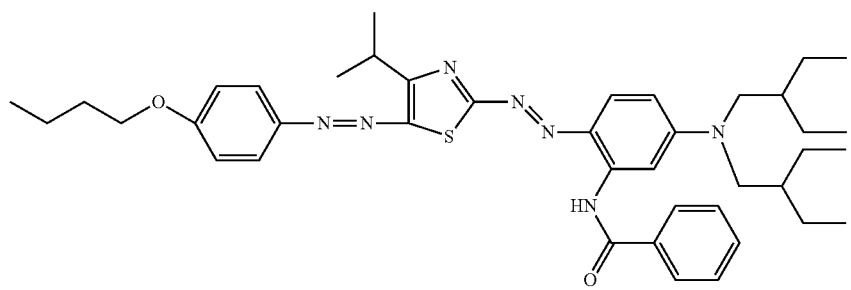
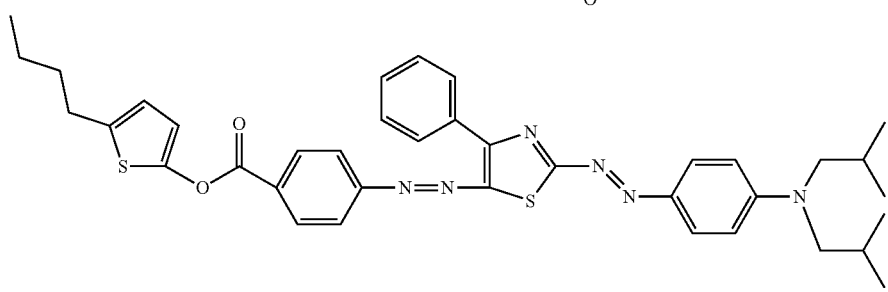
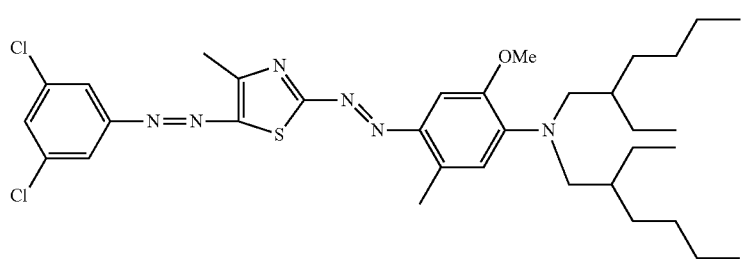
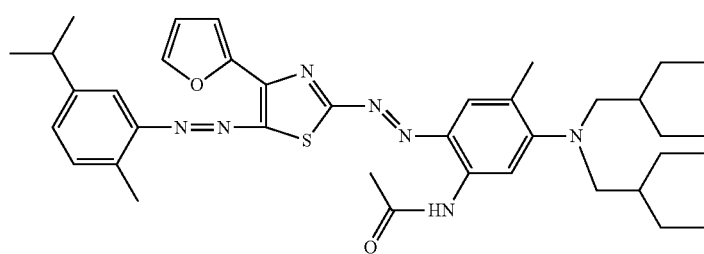
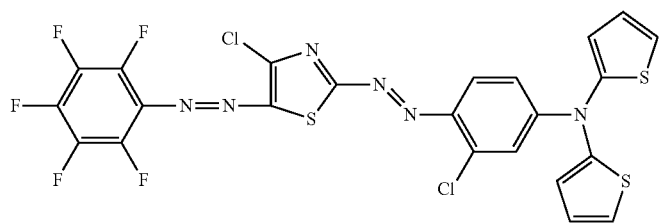

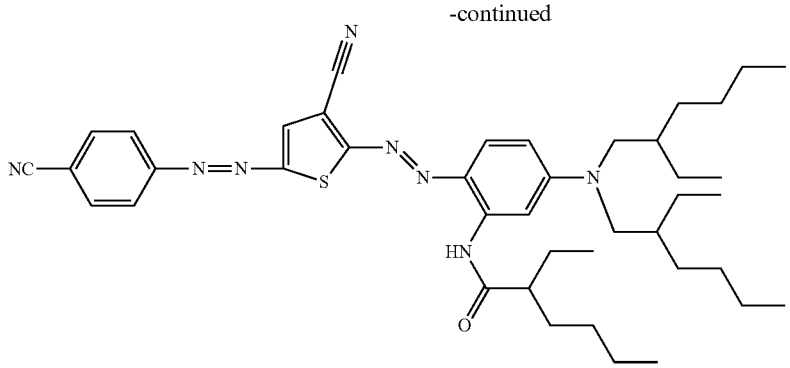

The heterocyclic compounds represented by the above-mentioned general formula (5) can be synthesized, for example, according to the method described in JP-A 3-256793.

In general, the molecular weight of the heterocyclic compounds represented by the above-mentioned general formulae (2) to (5) is 2000 or less, including the substituents, if any, therein, and preferably 1000 or less, and is generally 300 or more and preferably 400 or more from the viewpoint of the gram absorbance coefficient thereof.

Not specifically defined, preferred examples of the above-mentioned cyanovinyl compounds are compounds represented by the following general formula (6).

[Chem. 23]

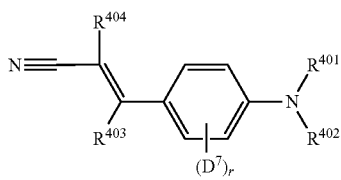

(6)

[In the general formula (6), $R^{401}$, $R^{402}$ and $D^7$ each independently represent an arbitrary substituent; $R^{403}$ and $R^{404}$ each independently represent a hydrogen atom, or an arbitrary substituent; r indicates an integer of from 0 to 4, and when r is 2 or more, two or more $D^7$s existing in one molecule may be the same or different.]

$R^{401}$ and $R^{402}$ each independently represent an arbitrary substituent. Not detracting from the advantageous effects of the present invention, $R^{401}$ and $R^{402}$ are not specifically defined, but preferably, these are independently an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent, for securing a high absorbance coefficient and high solubility in solvent.

The alkyl group for $R^{401}$ and $R^{402}$ has, concretely, the same meaning as that of the alkyl group exemplified for $R^1$ in the above-mentioned general formula (1), and the substituent that the group may have is also the same. The alkyl group for $R^{401}$ and $R^{402}$ preferably has 2 or more carbon atoms, more preferably 4 or more carbon atoms. Also preferably, the group has 16 or less carbon atoms, more preferably 12 or less carbon atoms. Having a carbon number that falls within the suitable range, the compound could have excellent solubility in solvent and could have a high gram absorbance coefficient.

The aryl group for $R^{401}$ and $R^{402}$ has, concretely, the same meaning as that of the aryl group exemplified for $R^{101}$ in the above-mentioned general formula (2), and the substituent that the group may have is also the same as that of the aryl group exemplified for $R^{101}$ in the general formula (2).

The heteroaryl group for $R^{401}$ and $R^{402}$, has, concretely, the same meaning as that of the heteroaryl group exemplified for $R^{101}$ in the above-mentioned general formula (2), and the substituent that the group may have is also the same as that of the heteroaryl group exemplified for $R^{101}$ in the general formula (2).

$R^{403}$ and $R^{404}$ each independently represent a hydrogen atom, or an arbitrary substituent. Not detracting from the advantageous effects of the present invention, $R^{403}$ and $R^{404}$ are not specifically defined, but preferably, $R^{403}$ is a hydrogen atom or a cyano group and $R^{404}$ is a cyano group or a group —$COR^{405}$, for securing a high absorbance coefficient and high solubility.

$R^{405}$ represents a hydrogen atom, an alkyl group having from 1 to 20 carbon atoms and optionally having a substituent, an alkoxy group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $R^{405}$ has, concretely, the same meaning as that of the alkyl group exemplified for $R^1$ in the above-mentioned general formula (1), and the substituent that the group may have is also the same. The alkyl group for $R^{401}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The alkoxy group for $R^{405}$ has, concretely, the same meaning as that of the alkoxy group exemplified for $R^1$ in the above-mentioned general formula (1), and the substituent that the group may have is also the same. The alkoxy group for $R^{405}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $R^{405}$ has, concretely, the same meaning as that of the aryl group exemplified for $R^{101}$ in the above-mentioned general formula (2), and the substituent that the group may have is also the same as that of the aryl group exemplified for $R^{101}$ in the general formula (2).

The heteroaryl group for $R^{405}$ has, concretely, the same meaning as that of the heteroaryl group exemplified for $R^{101}$ in the above-mentioned general formula (2), and the substituent that the group may have is also the same as that of the heteroaryl group exemplified for $R^{101}$ in the general formula (2).

$D^7$ represents an arbitrary substituent. Not detracting from the advantageous effects of the present invention, $D^7$ is not specifically defined, but is preferably a hydrogen atom, a halogen atom, an alkyl group having from 1 to 20 carbon atoms and optionally having a substituent, an alkoxy group having from 1 to 20 carbon atoms and optionally having a substituent, a group —NHCOR$^{406}$ or a group —NHSO$_2$R$^{407}$, for securing a high absorbance coefficient and high solubility in solvent r indicates an integer of from 0 to 4, and when r is 2 or more, two or more $D^7$s existing in one molecule may be the same or different.

$R^{406}$ and $R^{407}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $D^7$, $R^{406}$ has, concretely, the same meaning as that of the alkyl group exemplified for $R^1$ in the above-mentioned general formula (1), and the substituent that the group may have is also the same. The alkyl group for $D^7$, $R^{406}$ and $R^{407}$ preferably has 2 or more carbon atoms, more preferably 4 or more carbon atoms. Also preferably, the group has 16 or less carbon atoms, more preferably 12 or less carbon atoms. Having a carbon number that falls within the suitable range, the compound could have excellent solubility in solvent and could have a high gram absorbance coefficient.

The alkoxy group for $D^7$ has the same meaning as that of the alkoxy group exemplified for $R^1$ in the above-mentioned general formula (1), and the substituent that the group may have is also the same. The alkoxy group for $D^7$ is preferably one having 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $R^{406}$ and $R^{407}$ has, concretely, the same meaning as that of the aryl group exemplified for $R^{101}$ in the above-mentioned general formula (2), and the substituent that the group may have is also the same as that the aryl group exemplified for $R^{101}$ in the general formula (2) may have.

The heteroaryl group for $R^{406}$ and $R^{407}$ has, concretely, the same meaning as that of the heteroaryl group exemplified for $R^{101}$ in the above-mentioned general formula (2), and the substituent that the group may have is also the same as that the heteroaryl group exemplified for $R^{101}$ in the general formula (2) may have.

Specific examples of the cyanovinyl compounds represented by the above-mentioned general formula (6) are shown below; however, not overstepping the scope and the spirit thereof, the present invention is not limited to these.

[Chem. 24]

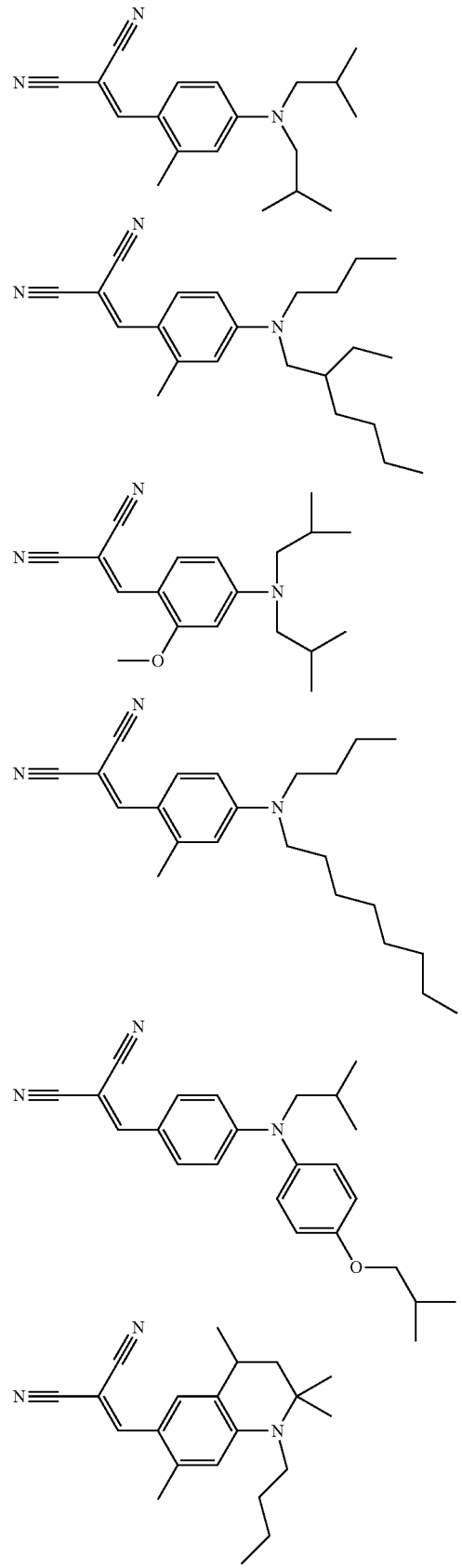

77
-continued
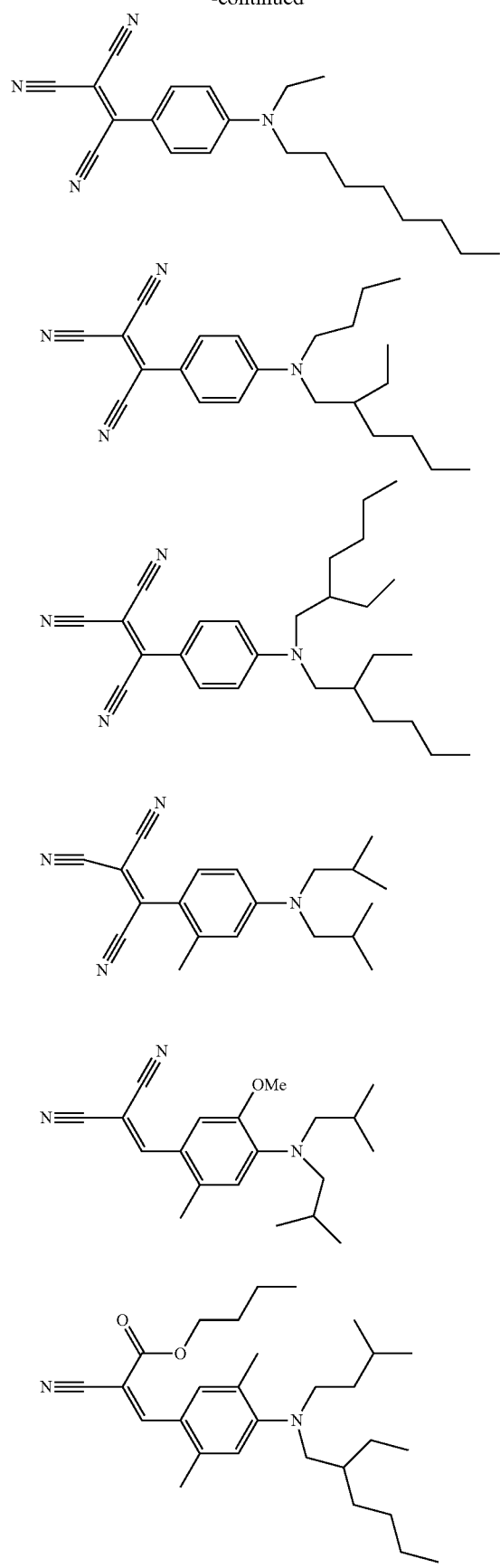
78
-continued
[Chem. 25]

79
-continued
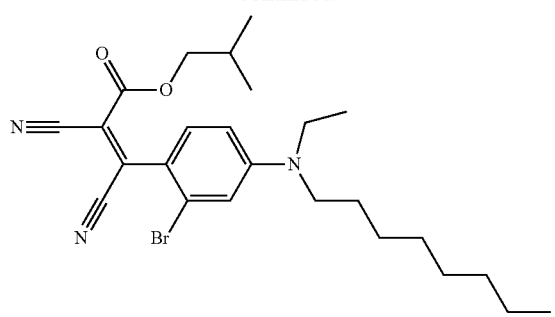
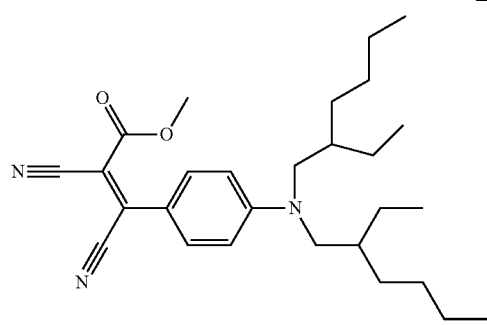
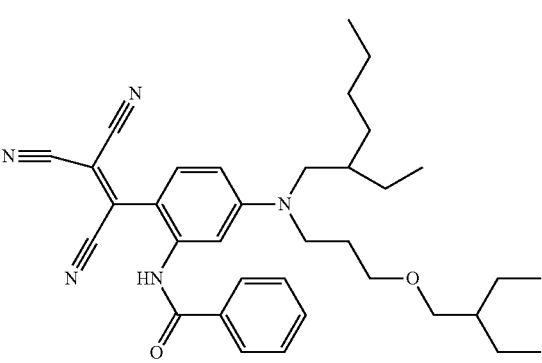
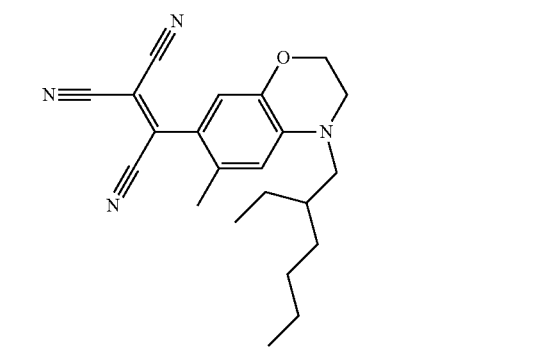
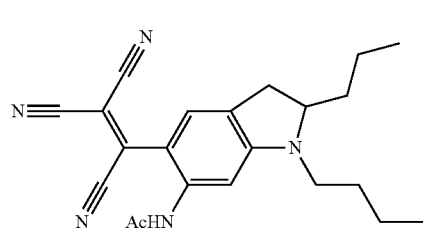
80
-continued
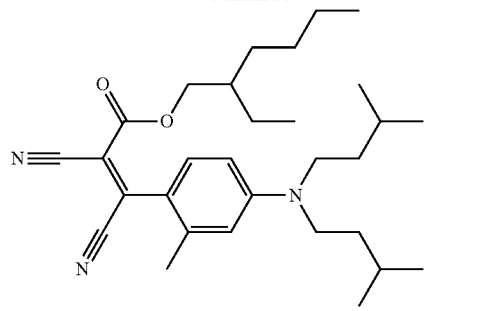
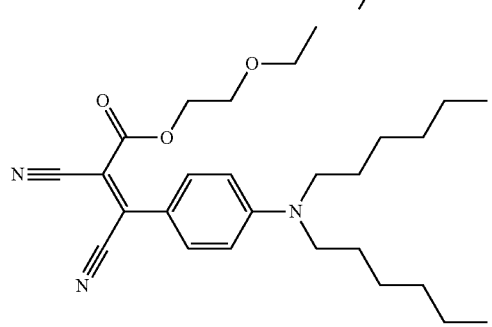
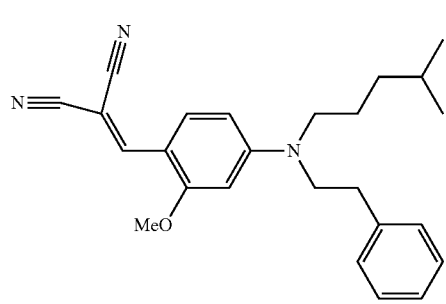
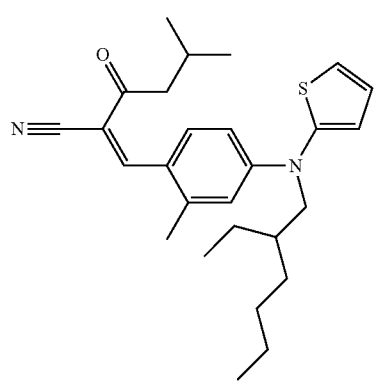
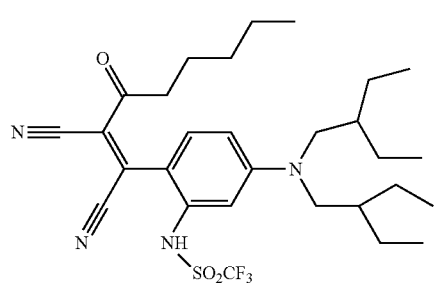

-continued

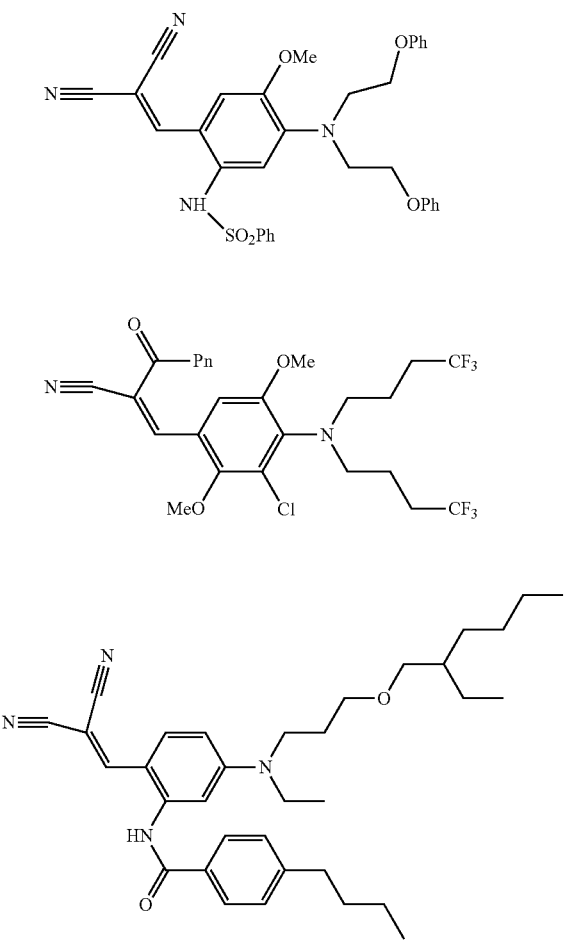

The compounds represented by the above-mentioned general formula (6) can be synthesized, for example, according to the method described in JP-A 11-100523 or 2000-247942.

Not specifically defined, preferred examples of the anthraquinone compounds are compounds represented by the following general formula (7).

[Chem. 26]

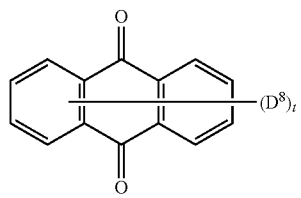

(7)

[In the general formula (7), $D^8$ represents an arbitrary substituent; t indicates an integer of from 0 to 8, and when t is 2 or more, two or more $D^8$s existing in one molecule may be the same or different.]

The formula (7) where t is from 1 to 8 means that at least one hydrogen atom at the 1- to 8-positions of anthraquinone is substituted with the substituent represented by $D^8$.

$D^8$ represents an arbitrary substituent. Not detracting from the advantageous effects of the present invention, $D^8$ is not specifically defined, but is preferably a halogen atom, an alkyl group having from 1 to 20 carbon atoms and optionally having a substituent, an alkoxy group having from 1 to 20 carbon atoms and optionally having a substituent, a cyano group, a hydroxy group, an amino group, a nitro group, a group —COOR$^{501}$, a group —NHR$^{502}$, a group —NH-COR$^{503}$ or a group —SR$^{504}$, for securing a high absorbance coefficient and high solubility in solvent t indicates an integer of from 0 to 8, and when t is 2 or more, two or more $D^8$s existing in one molecule may be the same or different.

$R^{501}$ to $R^{504}$ each independently represent a hydrogen atom, an alkyl group having from 1 to 20 carbon atoms and optionally having a substituent, an aryl group having from 6 to 20 carbon atoms and optionally having a substituent, or a heteroaryl group having from 2 to 20 carbon atoms and optionally having a substituent.

The alkyl group for $D^8$ and $R^{501}$ to $R^{504}$ has, concretely, the same meaning as that of the alkyl group exemplified for $R^1$ in the above-mentioned general formula (1), and the substituent that the group may have is also the same. The alkyl group for $D^8$ and $R^{501}$ to $R^{504}$ preferably has 16 or less carbon atoms, more preferably 10 or less carbon atoms, even more preferably 6 or less carbon atoms. Having a carbon number that falls within the suitable range, the compound could have excellent solubility in solvent and could have a high gram absorbance coefficient.

The aryl group for $R^{501}$ to $R^{504}$ has, concretely, the same meaning as that of the aryl group exemplified for $R^{101}$ in the above-mentioned general formula (2), and the substituent that the group may have is also the same as that the aryl group exemplified for $R^{101}$ in the general formula (2) may have. The aryl group for $R^{502}$ to $R^{504}$ is preferably a phenyl group or a naphthyl group optionally having a substituent, for the reason of high solubility in solvent.

The substituent that the phenyl group or the naphthyl group may have is preferably a halogen atom, an alkyl group having from 1 to 10 carbon atoms, or an alkoxy group having from 1 to 10 carbon atoms, for the reason of high solubility in solvent.

The heteroaryl group for $R^{501}$ to $R^{504}$ has, concretely, the same meaning as that of the heteroaryl group exemplified for $R^{101}$ in the above-mentioned general formula (2), and the substituent that the group may have is also the same as that the heteroaryl group exemplified for $R^{101}$ in the general formula (2) may have.

Specific examples of the anthraquinone compounds represented by the above-mentioned general formula (7) are shown below; however, not overstepping the scope and the spirit thereof, the present invention is not limited to these.

[Chem. 27]
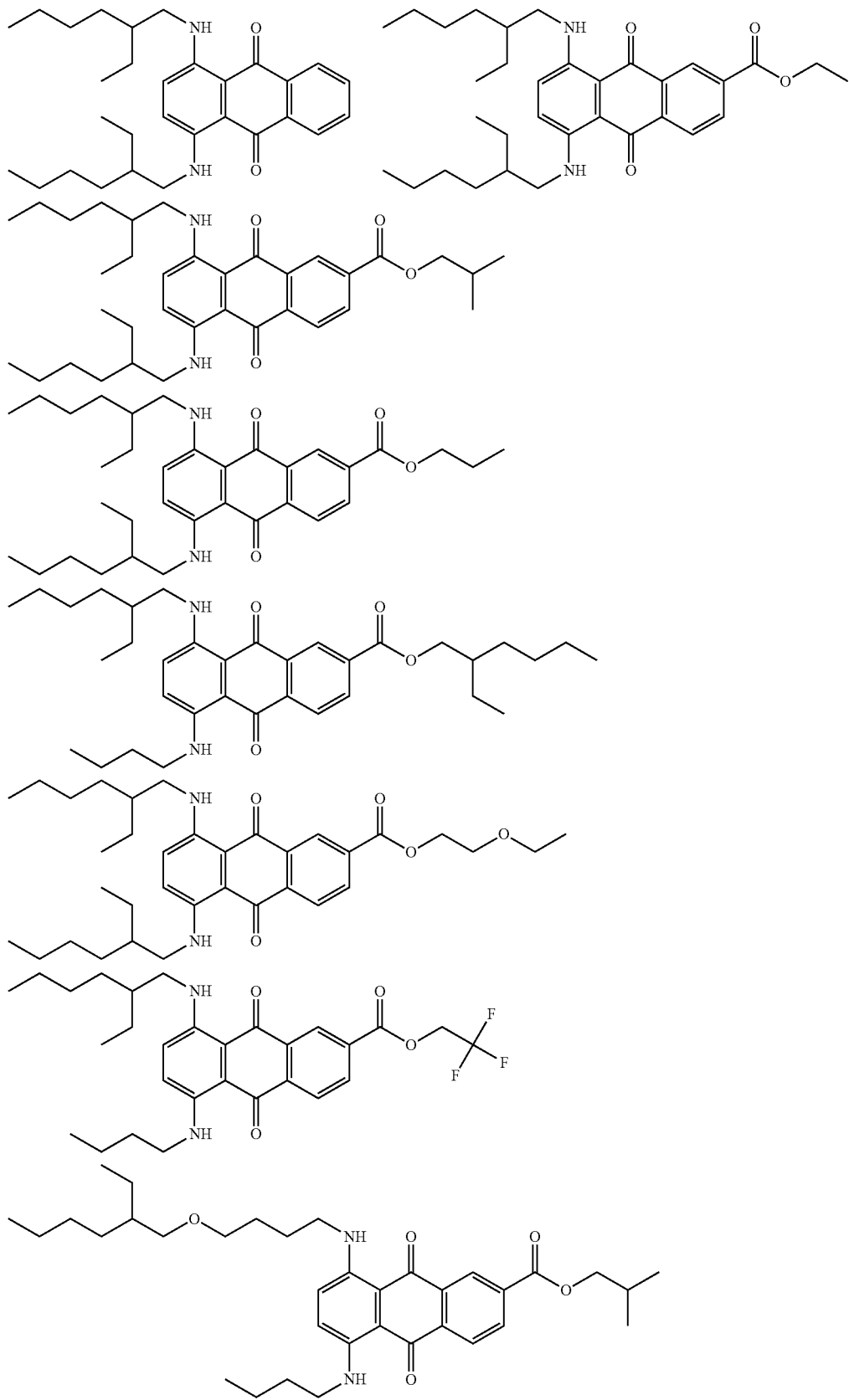

-continued
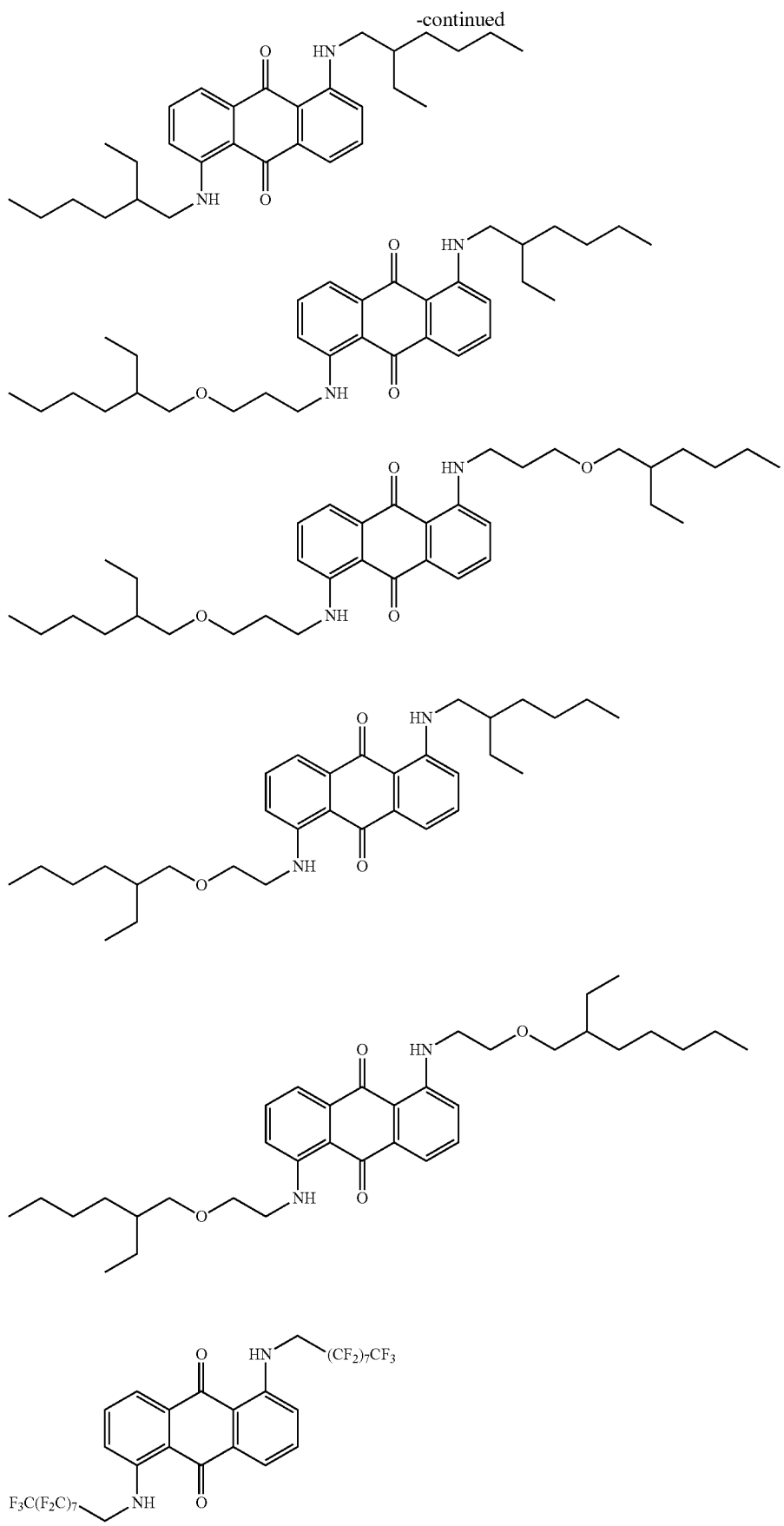

-continued
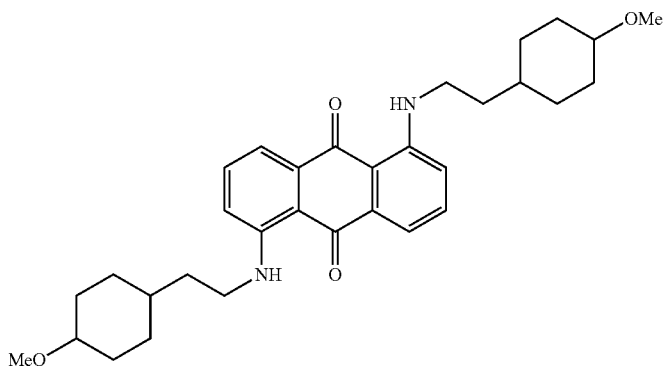
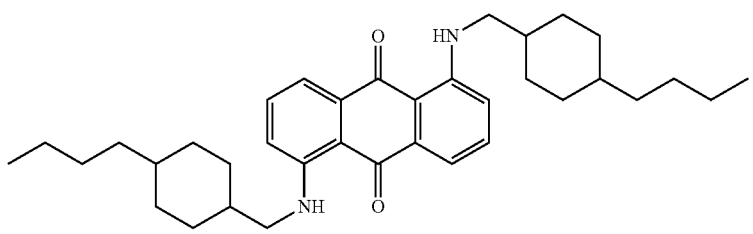
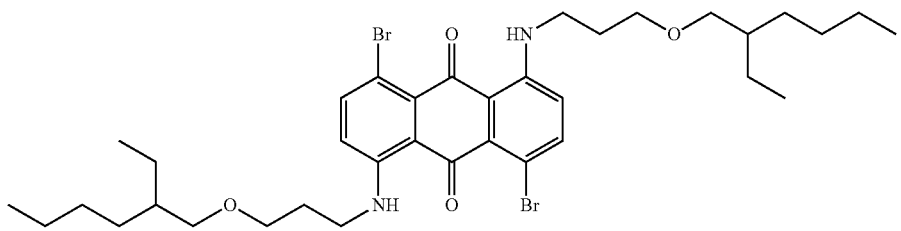
[Chem. 28]
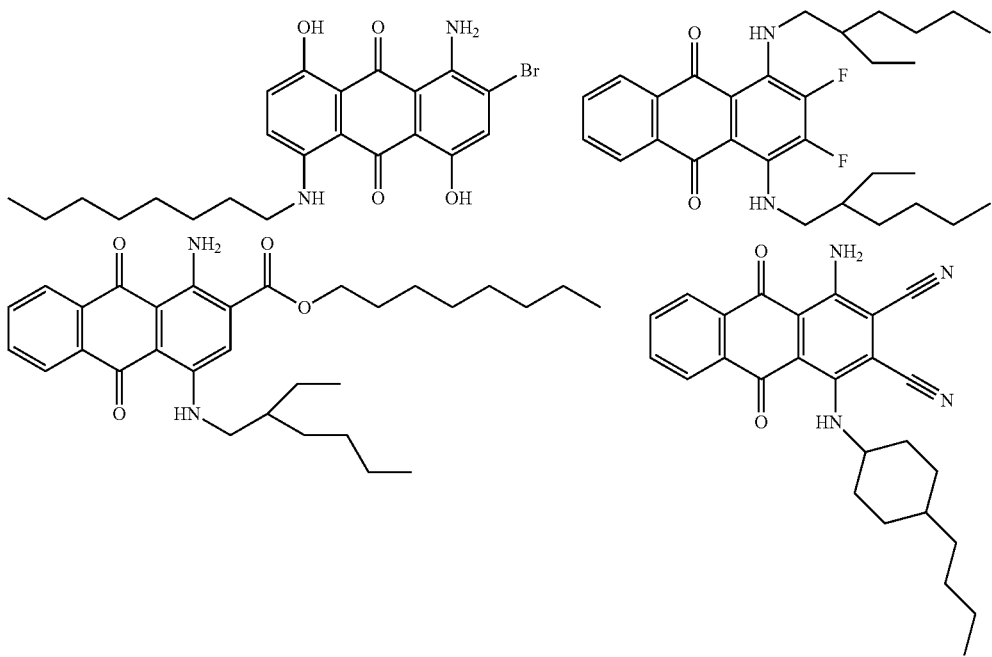

89
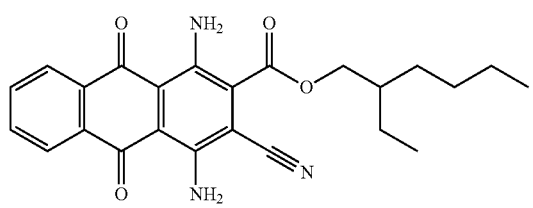
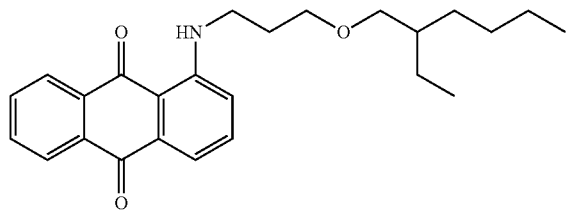
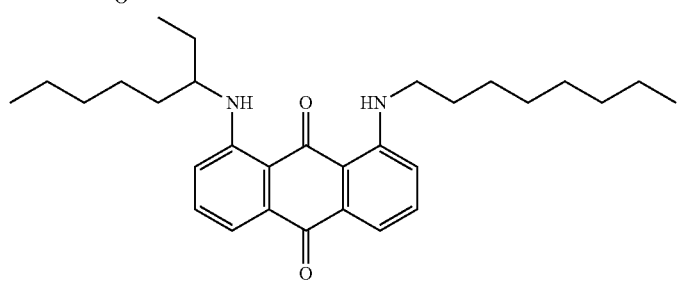
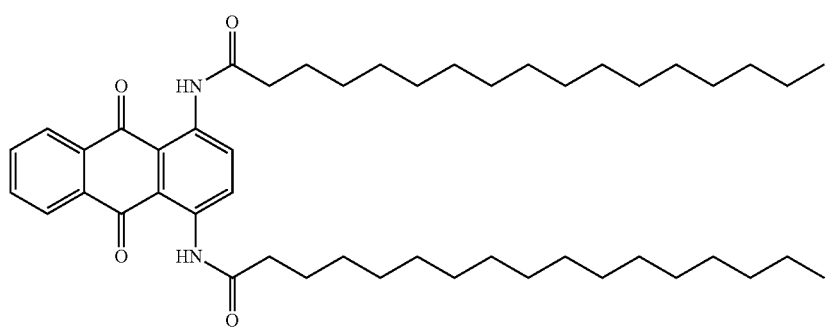
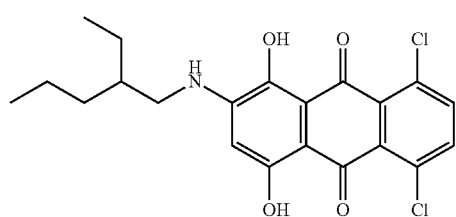
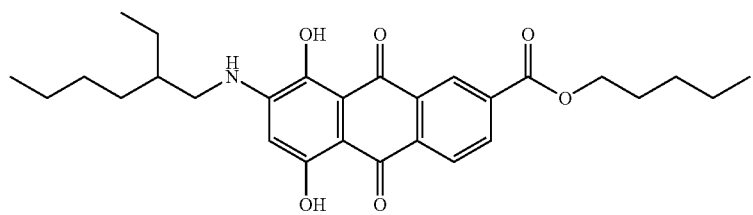
90
-continued
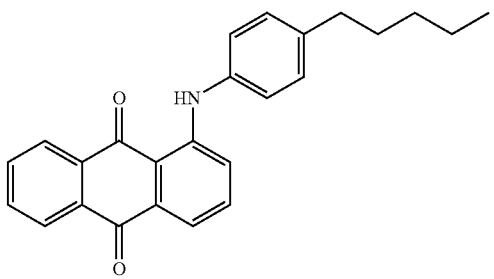
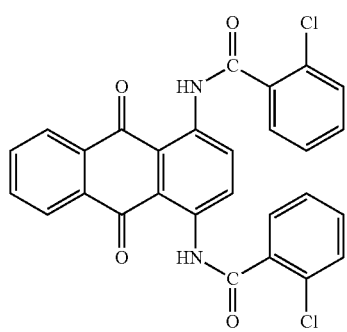

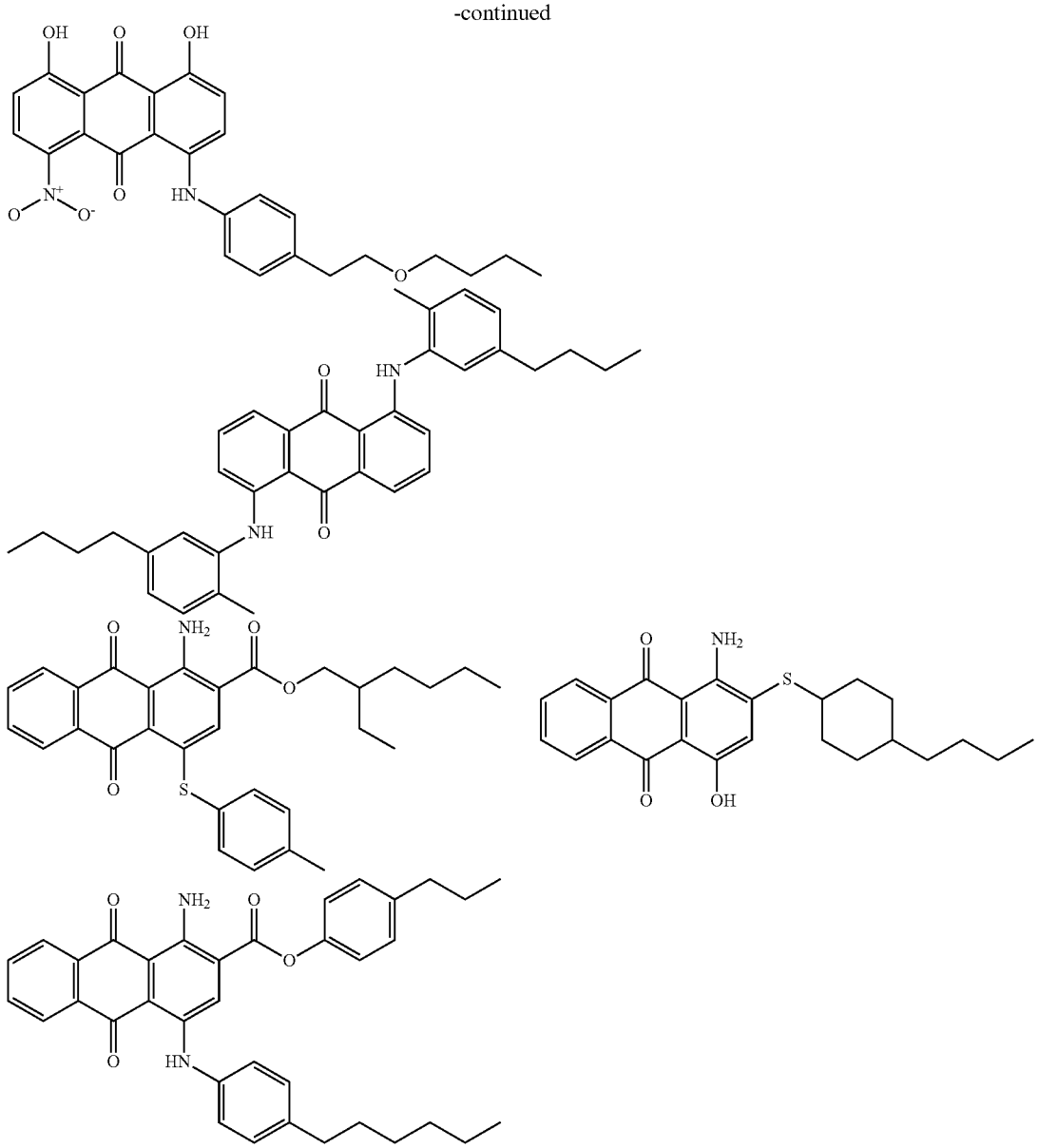

The anthraquinone compounds represented by the above-mentioned general formula (7) can be synthesized, for example, according to the method described in U.S. Pat. No. 5,558,808 and JP-T 11-506151

In general, the molecular weight of the anthraquinone compounds represented by the above-mentioned general formula (7) is 2000 or less, including the substituents, if any, therein, and preferably 1000 or less, and is generally 300 or more and preferably 400 or more, from the viewpoint of the gram absorbance coefficient thereof.

The compounds represented by the above-mentioned general formulae (1) to (7) are compounds having an absorption maximum wavelength falling within a specific range and are not specifically defined; however, for producing an ink having a high OD and a low viscosity, it is desirable that the compounds have an excellent solubility in solvent, especially an excellent solubility in a solvent having a relative permittivity of 3 or less and having a solubility in water at 25° C. of 20 mg/L or less.

Preferably, the solubility of the compounds represented by the general formulae (1) to (7) in an n-decane solution at 5° C. is 1% by mass or more, more preferably 3% by mass or more, even more preferably 5% by mass or more. The solubility is preferably higher, but is generally about 80% by mass or less. Having a solubility not lower than a specific value, the compounds could make it possible to provide good displays in display devices.

In case where the compounds represented by the general formulae (1) to (7) are used in electrowetting displays, the compounds are preferably insoluble in water in view of the principles of the displays. Here, "insolubility in water" means that the solubility of the compounds in water at 25° C. and under one atmospheric pressure is 0.1% by mass or less, preferably 0.01% by mass or less.

Preferably, the molar absorbance coefficient of the compounds represented by the general formulae (1) to (7) is 40000 (L·mol$^{-1}$·cm$^{-1}$) or more, more preferably 50000 (L·mol$^{-1}$·cm$^{1}$) or more for satisfying the performance of display devices.

In an ink containing a compound represented by the general formulae (1) to (7), the concentration of the compound may be suitably controlled according to its objective. In case where the compounds are used in electrowetting displays, in general, the concentration is 0.2% by mass or more, and the compound may be diluted in a solvent in accordance with the necessary εC value thereof. Preferably, the concentration is 1% by mass or more, more preferably 5% by mass or more. Also preferably, the concentration is, in general, preferably about 80% by mass or less.

In case where the ink of the present invention is black, it is desirable that the ink contains at least one of the compounds of (2) to (7) in addition to the compound of the general formula (1). Containing these compounds, the ink can realize a high light absorption in a broad wavelength range falling within a visible light region. Even when these compounds are used as mixed here, the solubility thereof in solvent does not lower, or that is, the compounds are excellent in exhibiting high solubility even in such a case.

Further, the ink of the present invention may contain, if desired, any arbitrary additives suitable to various uses within a range not detracting from the advantageous effects of the present invention.

The hue of ink can be quantitatively evaluated on a CIE color system chromaticity L*a*b*. L* means a brightness, L*=0 means a diffuse color of black, and L*=100 means a diffuse color of white. a*b* means a hue, and a saturation is represented by C* to be calculated from a*b* and according to $C^* = \sqrt{(a^{*2} + b^{*2})}$. C* of nearer to 0 means colorless.

In case where the ink of the present invention is black, it provides a good hue since the value of L* as well as C* is nearer to 0. When measured with a cell having a measurement optical length of 0.01 mm, C* is preferably 2 or less, more preferably 1.5 or less. The lower limit is not defined, and C* is preferably nearer to 0. Similarly, when measured with a cell having a measurement optical length of 0.01 mm, the value of L* is preferably 3 or less, more preferably 2 or less. The lower limit is not defined, and L* is preferably nearer to 0.

The optical density (OD) of the ink of the present invention is preferably higher, and the upper limit thereof is not defined. Under the same measurement optical length, the OD value of the ink depends on the compound concentration, the compound absorption wavelength, etc. For example, when the compound concentration is high, then the OD value of the ink is also high. However, increasing the compound concentration would increase the ink viscosity.

On the other hand, the ink of the present invention contains a compound having an absorption in the wavelength region of high luminosity, and therefore the concentration of the compound in the ink needed for the desired OD could be low, or that is, the ink of the present invention is a high-OD and low-viscosity ink and is therefore especially useful in use applications to be mentioned below.

The ink of the present invention is characterized by containing a solvent having a relative permittivity at a measurement frequency of 1 kHz of 3 or less and having a solubility in water at 25° C. of 25 mg/L or less, and at least one each of the following compounds (I) to (IV):

(I) A compound of which a decane solution has an absorption maximum wavelength of from 400 nm to less than 500 nm, (II) A compound of which a decane solution has an absorption maximum wavelength of from 500 nm to less than 570 nm, (III) A compound of which a decane solution has an absorption maximum wavelength of from 570 nm to less than 630 nm, (IV) A compound of which a decane solution has an absorption maximum wavelength of from 640 nm to 700 nm.

The ink of the present invention contains at least one each of the above-mentioned compounds (I) to (IV), and therefore has a high absorption in a broad wavelength region, and is especially useful as a black ink. In addition, the concentration of the compound needed for making the ink have a desired OD can be lowered, and therefore, the ink is a high-OD and low-viscosity ink and is especially useful in use applications to be mentioned below.

Not specifically defined, the above-mentioned compounds (I) to (IV) may be any compounds having an absorption maximum wavelength in a specific range, but are preferably those excellent in solubility in solvent, especially excellent in solubility in a solvent having a relative permittivity of 3 or less and having a solubility in water at 25° C. of 20 mg/L or less, for obtaining the high-OD and low-viscosity ink.

The compounds (I) to (IV) preferably have a solubility in n-decane at 5° C. of 1% by mass or more, more preferably 3% by mass or more, even more preferably 5% by mass or more. The solubility is preferably higher, but is generally about 80% by mass or less. Having a solubility not lower than a specific value, the compounds could make it possible to provide displays on display devices, etc.

When used in electrowetting displays, the compounds (I) to (IV) are preferably insoluble in water in view of the principles of the displays. Here, "insolubility in water" means that the solubility of the compounds in water at 25° C. and under one atmospheric pressure is 0.1% by mass or less, preferably 0.01% by mass or less.

Preferably, the molar absorbance coefficient of the compounds (I) to (IV) is 40000 (L·mol$^{-1}$·cm$^{-1}$) or more, more preferably 50000 (L·mol$^{-1}$·cm$^{-1}$) or more for satisfying the performance of display devices.

A value of the product, εC, of the molar absorbance coefficient at the absorption maximum wavelength of an n-decane solution of the compounds (I) to (IV), ε(L·mol$^{-1}$·cm$^{-1}$), and the saturation solubility of the solution at 5° C., C (mol·L$^{-1}$), is generally 500 cm$^{-1}$ or more, preferably 1000 cm$^{-1}$ or more, more preferably 2000 cm$^{-1}$ or more. Not specifically defined, the upper limit is generally 60000 cm$^{-1}$ or less.

The concentration of the compounds (I) to (IV) in the ink of the present invention may be controlled at any desired value in accordance with the intended purpose thereof. For example, in case where the compound is used as a dye for electrowetting displays, the concentration thereof is generally 1% by mass or more, or that is, the compound may be diluted in a nonpolar solvent in accordance with the desired concentration thereof. Preferably, the concentration is 3% by mass or more, more preferably 5% by mass or more. Also preferably, the concentration is generally about 80% by mass or less.

Of the ink of the present invention containing at least one each of the compounds (I) to (IV), the lower limit of the ink viscosity at an ink temperature of 25° C. is, in general, preferably 0.1 mPa·s or more, though not specifically defined. Also preferably, the upper limit is 10000 mPa·s or less, more preferably 1000 mPa·s or less, even more preferably 100 mPa·s or less. When the viscosity thereof is too large, then the ink would interfere with operation of display devices.

Not specifically defined, the above-mentioned compounds (I) to (IV) may be any compounds having an absorption maximum wavelength in a specific range. For example, as (I), there are mentioned the compounds represented by the general formula (2), etc.; as (II), there are mentioned the compounds represented by the general formulae (3) and (4), etc.; as (III), there are mentioned the compounds represented by the general formulae (1), (3), (4) and (5), etc.; and as (IV), there are mentioned the compounds represented by the general formula (5), etc.

If desired but within a range not detracting from the advantageous effects of the present invention, the ink of the present invention may contain any arbitrary additive suitable for various use applications. Regarding the relative permittivity and the viscosity of the solvent for use in the present invention and the ink containing the solvent and a dye of the present invention, when the difference in the value between the solvent and the ink is smaller, then the influence thereof on the operation characteristics in use in display devices and others could be small, and therefore, it is desirable that the additive does not change the characteristics of the solvent.

As the solvent for use in the ink containing at least one each of the compounds (I) to (IV) of the present invention, usable is the same solvent as in the ink described hereinabove, and the preferred range and the reason thereof are also the same.

(Use Applications)

The ink of the present invention is favorably used as an ink for displays. As displays, the present invention is especially useful as a display which has a display area containing an ink and which displays an image by controlling the voltage application to the display area, a display which displays an image by changing the coloration state through control of voltage application, and an display which displays an image using at least either one of electrophoretic particles and an aqueous medium in the display area thereof.

As the display which displays an image by changing the coloration state through voltage application, for example, there may be mentioned those where a colored or colorless ink or a solvent is moved through development, aggregation thereof or the like under voltage application thereto whereby the color is changed to display images, to which, however, the present invention is not limited.

Here, the electrophoretic particles are electrically-charged particles which may be colored, and the display area may contain different types of electrophoretic particles. The aqueous medium is a fluid that may be colored, and the display area may contain different types of aqueous media. The aqueous medium includes water, non-charged liquids, liquids having an affinity to water, and liquids similar to water in point of the surface tension thereof. Concretely, for example, there are mentioned alcohols, liquids that contain an inorganic salt such as an alkali metal halide, etc.

The azo compound and the ink of the present invention are especially useful as an ink for use for electrowetting-mode displays or for electrophoresis-mode displays.

Combining the azo compound of the present invention with any other compound, the present invention can provide good inks having an excellent hue, such as black ink or the like, and for example, the black ink is useful also as a member capable of functioning as an optical shutter.

The ink of the present invention is applicable to any display devices having a displaying unit, but is especially useful for electronic papers.

As display modes, there are exemplified an electrowetting mode, an electrophoretic mode, etc. As display use applications, there are mentioned various types of displays for computers, digital signage boards, electronic papers, electronic inks, etc. There is a possibility that the present invention is replaceable for almost all use applications of already-existing liquid-crystal displays. Above all, the ink of the present invention is especially favorable for an ink for electrowetting displays.

EXAMPLES

The present invention is described more concretely with reference to Examples thereof and Comparative Examples given below; however, the present invention is not whatsoever limited to the following Examples.

Synthesis of Intermediate A-1

Synthesized according to the method described in WO2012/033177.

Synthesis of Intermediate A-2

Synthesized according to the method described in WO2012/033177.

Synthesis of Intermediate A-3

A mixture of the intermediate A-1 (14.1 g, 38 mmol), methanol (42 ml), water (70 ml) and 35% hydrochloric acid (63 ml) was stirred at 65° C. for 3.5 hours, then restored to room temperature, poured into an aqueous sodium acetate solution cooled in an ice bath, and extracted with hexane, then the hexane layer was dried with anhydrous sodium sulfate and concentrated under reduced pressure to give 16.9 g of an oily substance. 4 g of the substance was metered, dissolved in toluene (24 ml), and cooled in an ice bath, to which triethylamine (3.4 ml, 24 mmol) and butanoic acid chloride (2.9 ml, 24 mmol) were dropwise added. After this was stirred with cooling with ice for 1 hour, water was added thereto, and this was extracted with chloroform. The chloroform layer was washed with 1 N hydrochloric acid, dried with anhydrous sodium sulfate, and concentrated under reduced pressure. This was purified through silica gel column chromatography to give an intermediate A-3 (2.36 g).

Synthesis of Intermediate B-1

With cooling with ice, 4-nitrobenzoyl chloride (60.00 g, 0.323 mol) was added to a mixture of 2-ethyl-1-hexanol (54.3 mL, 0.346 mol), toluene (200 mL) and triethylamine (56.8 mL, 0.407 mol). After the addition, this was stirred still at 0° C. for 1 hour, then water was added thereto, and the aqueous layer was extracted with chloroform. The chloroform layer was dried with anhydrous sodium sulfate, and the filtrate after filtration was concentrated. Hexane (300 mL) was added thereto, and the precipitated solid was removed through filtration, and the filtrate was concentrated to give an oily substance. Ethanol (400 ml) was added to the resultant oily substance, then 10% palladium carbon (containing 55% water, manufactured by Tokyo Chemical Industry, 5 g) was added thereto, cooled in an ice bath, and while the internal temperature was kept at 20° C. or lower, hydrazine monohydrate (25.9 g, 808 mmol) was dropwise added thereto, taking 40 minutes, and thereafter while the internal temperature was kept at 40 to 50° C., this was stirred for 1 hour. After cooled in an ice bath, the palladium carbon was removed through filtration, the filtrate was concentrated under reduced pressure, water was added to the resultant oily substance, the formed agglomerate was collected through filtration, washed with methanol/water=2/1 (by volume)

(400 ml), and dried under reduced pressure to give an intermediate B-1 (65.8 g) as a white solid.

Synthesis of Intermediate B-2

The intermediate B-1 (2.0 g, 8.02 mmol) was dissolved in N,N-dimethylformamide (60 mL), heated up to 45° C., and N-bromosuccinimide (2.997 g, 16.84 mmol) was added thereto little by little. After the addition, this was stirred for 30 minutes, and then restored to room temperature. Water (60 mL) was added thereto, and the aqueous layer was extracted with hexane. The hexane layer was dried with anhydrous sodium sulfate, and the filtrate after filtration was concentration. The resultant crude substance was purified through column chromatography to give an intermediate B-2 (3.03 g, yield 93%).

Synthesis of Intermediate C-1

A mixture of 2,6-dibromo-4-trifluoromethylaniline (manufactured by Wako Pure Chemicals, 0.78 g, 2.45 mmol) and 95% sulfuric acid (1.5 mL) was cooled to an internal temperature of 0° C., and 40% nitrosylsulfuric acid (0.85 g, 2.67 mmol) was dropwise added thereto at the internal temperature kept at 0° C. This was stirred for 1 hour at an internal temperature of from −2° C. to 0° C., and with cooling with ice, this was poured into 5 mL of ice in water to give a diazo liquid. In a separate vessel, the intermediate A-1 (1.00 g, 2.67 mmol) was dissolved in acetic acid (2 mL), and dropwise added to the resultant diazo liquid at an internal temperature of 0° C. or lower. After the addition, this was left at 0° C. for 1 hour, then extracted with toluene, and the toluene layer was washed with water and saturated saline water, and dried with anhydrous sodium sulfate. This was concentrated under reduced pressure, and purified through silica gel column chromatography to give an intermediate C-1 (0.33 g, yield 19%) as a reddish tar-like substance.

Synthesis of Intermediate C-2

A mixture of the intermediate B-2 (3.03 g, 7.44 mmol), acetic acid (9 mL) and propionic acid (4.5 mL) was cooled to −5° C., and 40% nitrosylsulfuric acid (2.60 g, 8.18 mmol) was dropwise added thereto. After the addition and still at −5° C. or lower, this was stirred for 30 minutes to give a diazo liquid. In a separate vessel, a mixture of the intermediate A-2 (2.89 g, 7.44 mmol), tetrahydrofuran (15 mL), methanol (15 mL) and sulfamic acid (0.144 g, 1.48 mmol) was cooled to −5° C., and the prepared diazo liquid was dropwise added thereto. After the addition and still at −5° C. or lower, this was stirred for 30 minutes, added to an aqueous saturated sodium acetate solution (45 mL), and stirred for 30 minutes. The reaction solution as restored to room temperature, and the aqueous layer was extracted with hexane. The organic layer was dried with anhydrous sodium acetate, and the filtrate after filtration was concentrated. The resultant crude substance was purified through column chromatography to give an intermediate C-2 (3.81 g, yield 64%) as an oily substance.

Synthesis of Intermediate C-3

A mixture of 2,6-dibromo-4-trifluoromethylaniline (1.61 g, 5.04 mmol), acetic acid (4.8 ml) and propionic acid (2.4 ml) was cooled to an internal temperature of −5° C. or lower, and 40% nitrosylsulfuric acid (1.76 g, 5.54 mmol) was dropwise added thereto. After the addition and still at −5° C. or lower, this was stirred for 30 minutes to give a diazo liquid. In a separate vessel, a mixture of the intermediate A-3 (2.10 g, 5.04 mmol), tetrahydrofuran (10 mL), methanol (10 mL) and sulfamic acid (0.073 g, 0.76 mmol) was cooled to −5° C., and the diazo liquid was dropwise added thereto. This was stirred for 30 minutes still at −5° C., then restored to room temperature, and water was added thereto, and extracted with hexane. The hexane layer was dried with anhydrous sodium sulfate, concentrated under reduced pressure, and purified through silica gel column chromatography to give an intermediate C-3 (1.71 g, yield 46%) as an oily substance.

Synthesis of Intermediate C-4

A mixture of the intermediate B-1 (2.00 g, 4.91 mmol), acetic acid (6 mL) and propionic acid (3 mL) was cooled to −5° C. or lower, and 40% nitrosylsulfuric acid (1.72 g, 5.40 mmol) was dropwise added thereto. After the addition and still at −5° C. or lower, this was stirred for 30 minutes to give a diazo liquid. In a separate vessel, a mixture of the intermediate A-2 (1.84 g, 4.91 mmol), tetrahydrofuran (9 mL), methanol (9 mL) and sulfamic acid (0.095 g, 0.98 mmol) was metered, cooled to −5° C. or lower, and the diazo liquid was dropwise added thereto. At this time, an aqueous saturated sodium acetate solution was dropwise added so that the resultant mixture could have a pH of from 3.8 to 4.5. After the addition and still at −5° C. or lower, this was stirred for 30 minutes. The reaction liquid was restored to room temperature, and the aqueous layer was extracted with toluene. The organic layer was dried with anhydrous sodium sulfate, and the filtrate after filtration was concentrated to give an intermediate C-4 as an oily substance. Not purified, the total volume of the product was used in the next reaction.

The structures of the intermediates A-1 to A-3, B-1, B-2 and C-1 to C-4 are shown below.

[Chem. 29]

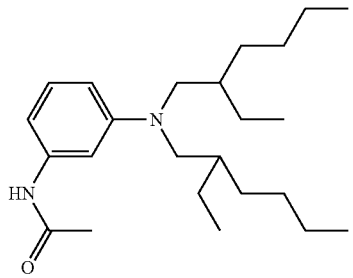

Intermediate A-1

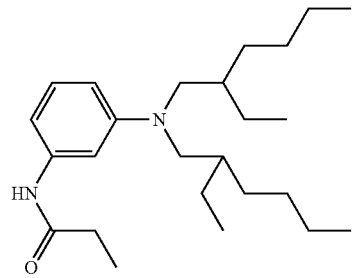

Intermediate A-2

Intermediate A-3

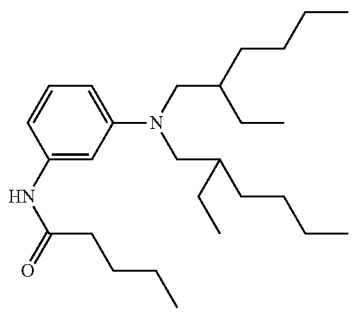

Intermediate B-1

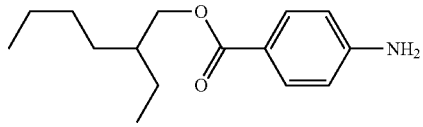

Intermediate B-2

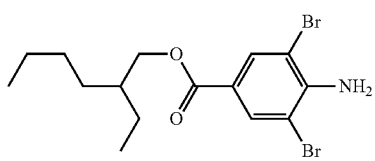

Intermediate C-1

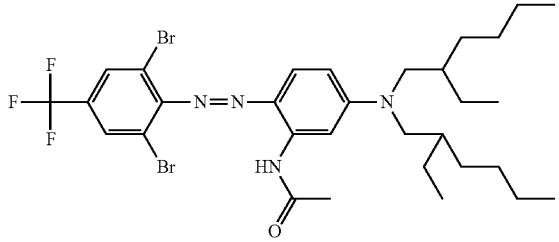

Intermediate C-2

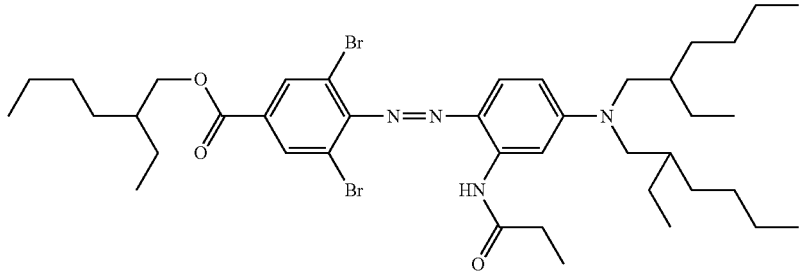

Intermediate C-3

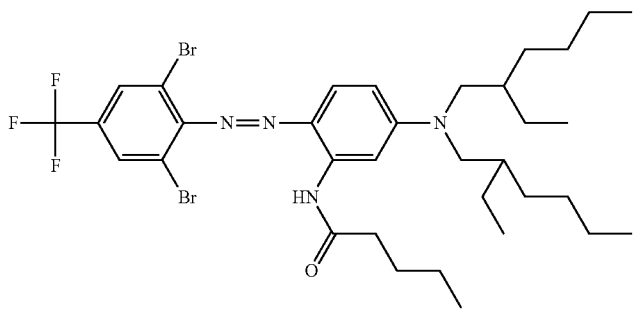

Intermediate C-4

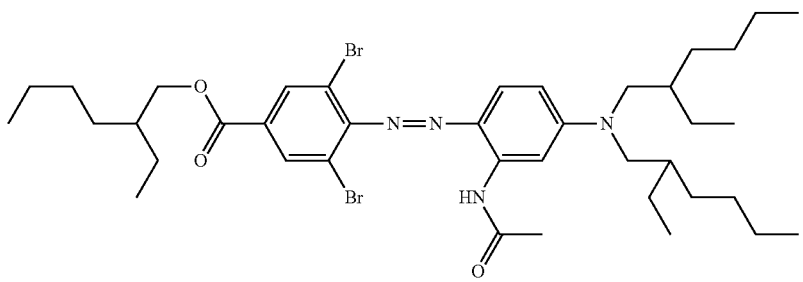

Synthesis of Example Compound 1

Copper(I) cyanide (0.11 g, 1.17 mmol) was added to a mixture of the intermediate C-1 (0.33 g, 0.47 mmol) and N,N-dimethylformamide (4 ml) to be washed with N,N-dimethylformamide (4 ml). After this was stirred at 80° C. for 4 hours, copper(I) cyanide (0.042 g, 0.47 mmol) was added thereto, and stirred at 100° C. for 2.5 hours. After left cooled, this was poured into water (10 ml) and stirred for 15 minutes, and the precipitated solid was taken out through filtration. This was purified through silica gel column chromatography, and the resultant powder was washed with water to give Example Compound 1 (0.078 g, yield 28%) as a solid.

Synthesis of Example Compound 2

A mixture of the intermediate C-2 (3.812 g, 4.73 mmol), copper(I) cyanide (1.057 g, 11.81 mmol) and N,N-dimethylformamide (60 mL) was stirred at room temperature for 2 hours. Water (60 mL) was added thereto, and the precipitate was taken out through filtration. The resultant crude matter was purified through column chromatography, and the resultant oily substance was solidified by processing it with methanol to give Example Compound 2 (0.305 g) as a solid.

Synthesis of Example Compound 3

A mixture of the intermediate C-3 (1.71 g, 2.29 mmol), copper(I) cyanide (0.513 g, 5.74 mmol) and N,N-dimethylformamide (28 mL) was stirred at 80° C. for 2 hours. Copper(I) cyanide (0.308 g, 3.43 mmol) was added thereto and stirred at 80° C. for 4 hours. This was cooled to room temperature, water was added thereto, the precipitate was taken out through filtration, and purified through silica gel column chromatography to give Example Compound 3 (0.30 g) as an oily substance.

Synthesis of Example Compound 4

Copper(I) cyanide (1.099 g, 12.28 mmol) and N,N-dimethylformamide (32 mL) were added to the entire volume of the oily substance obtained in synthesis of intermediate C-4, and stirred at room temperature for 2 hours. Water (32 mL) was added thereto, and the precipitate was taken out through filtration. The resultant crude matter was purified through column chromatography, and processed with methanol for solidification to give Example Compound 4 (1.478 g).

Comparative Example Compound

Compound M-2 in JP-A 01-136787 was used as Comparative Example Compound.

The structures of Example Compounds 1 to 4 and Comparative Example Compound are shown below.

[Chem. 30]

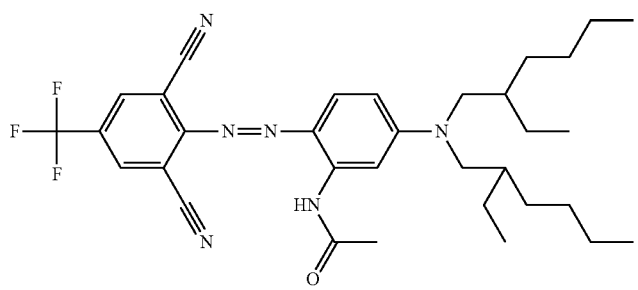

Example Compound 1

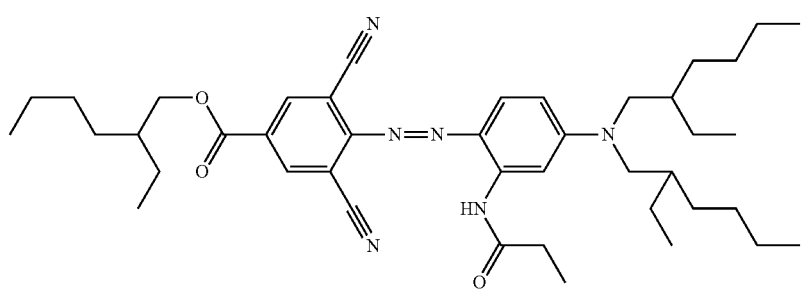

Example Compound 2

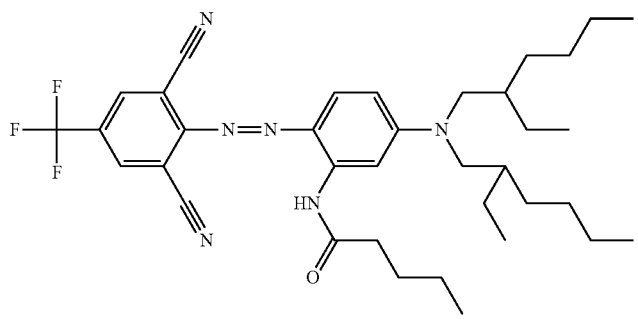

Example Compound 3

-continued

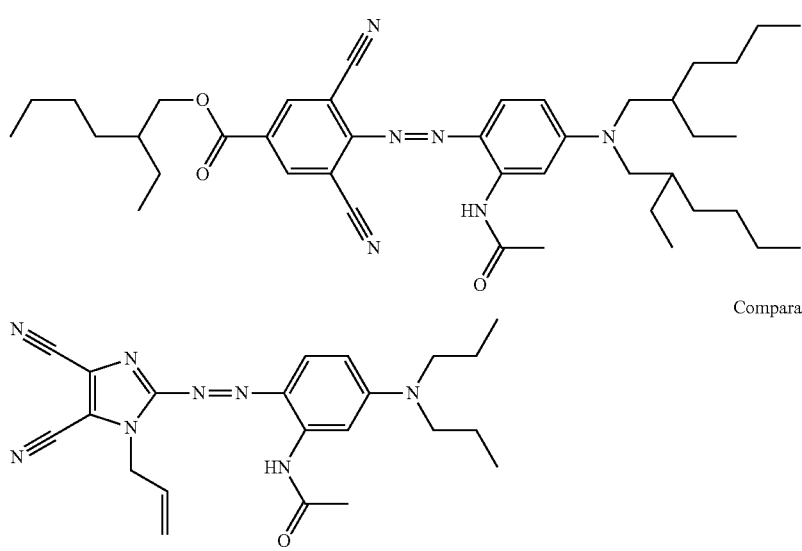

Example Compound 4

Comparative Example Compound

One of Example Compounds 1 to 4 and Comparative Example Compound was combined with a solvent of n-decane (having a relative permittivity at 22° C. and at a measurement frequency of 1 kHz of 2.0 and having a solubility in water at 25° C. of 1 mg/L or less) to prepare an ink.

The color of the solution of each compound, and the absorption maximum wavelength (λmax), the solubility C at 5° C., ε and ε·C thereof are summarized in Table 4.

<Method for Measurement of Relative Permittivity of Solvent>

The solvent was sandwiched between opposed parallel-plate ITO electrode-attached glass substrates having an electrode spacing of 50 μm, and using LCR Meter ZN2371 (manufactured by NF Corporation), the equivalent parallel capacitance thereof was measured at a measurement temperature of 22° C. and at a frequency of 1 kHz, given a test signal voltage of 5 V. Through calculation according to the following equation, the relative permittivity of the solvent was determined.

Relative Permittivity=(equivalent parallel capacitance)×(electrode spacing)/(electrode area)/vacuum permittivity($\varepsilon_0$)

<Method for Measurement of Solubility of Solvent in Water>

30 g of pure water and 8 g of the solvent were put into a 110 ml-vial, and shaken in a thermostat bath at 25° C. at 200 shake/min for 4 hours. After thus shaken, the liquid was centrifuged (6000×g, 5 minutes), the aqueous layer was sampled, and the concentration of the dissolved solvent was quantified through gas chromatography.

For a mixed solvent comprising two or more different types of solvents, the solubility in water was determined by multiplying the solubility in water of each solvent constituting the mixed solvent by the molar fraction of each solvent, followed by totaling the resultant data.

In case where the solvent species used is unknown, the solvent species is identified through mass spectrometry or the like, and the solubility of the solvent in water is determined according to the above-mentioned method.

<Method for Measurement of Absorption Maximum Wavelength λMax, Molar Absorbance Coefficient ε>

One mg of each of Example Compounds 1 to 4 and Comparative Example Compound was dissolved in 100 ml of n-decane solution to prepare a solution thereof, and using a quartz cell, the absorption spectrum thereof was measured with Hitachi Spectrophotometer U-4100. The resultant spectrum of the compound gave the absorption maximum wavelength λmax (nm) and the molar absorbance coefficient $\varepsilon(L \cdot mol^{-1} \cdot cm^{-1})$ thereof.

<Method for Measurement of Solubility C>

The solubility C of Example Compounds 1 to 4 and Comparative Example Compound in n-decane solution was measured as follows.

The compound was added to the solvent until the undissolved residue remained, and ultrasonically treated at 30° C. for 30 minutes. After left at 5° C. for 24 hours, this was centrifuged and filtered through a 0.1 μm-filter using an ultracompact centrifuge (centrifugal force, 5200×g). The resultant saturated solution was diluted to have a suitable concentration, and using a quartz cell having an optical length of 10 mm, the absorption spectrum thereof was measured with Hitachi Spectrophotometer U-4100. From the relationship between the absorbance at the absorption maximum wavelength λmax (nm) and the previously-determined molar absorbance coefficient $\varepsilon(L \cdot mol \cdot L^{-1})$ thereof, the concentration of each compound was determined, and the solubility C $(mol \cdot L^{-1})$ at 5° C. and εC $(cm^{-1})$ thereof were calculated.

TABLE 4

| Compound | Color Tone | Maximum Absorption Wavelength (nm) | ε (L · mol$^{-1}$ · cm$^{-1}$) | C (mol · L$^{-1}$) | ε · C (cm$^{-1}$) |
|---|---|---|---|---|---|
| Example Compound 1 | violet | 584 | 80,000 | 0.02 | 1,600 |
| Example Compound 2 | violet | 591 | 80,000 | 0.16 | 13,000 |
| Example Compound 3 | violet | 585 | 75,000 | 0.35 | 26,000 |

TABLE 4-continued

| Compound | Color Tone | Maximum Absorption Wavelength (nm) | $\epsilon$ (L·mol$^{-1}$·cm$^{-1}$) | C (mol·L$^{-1}$) | $\epsilon \cdot C$ (cm$^{-1}$) |
|---|---|---|---|---|---|
| Example Compound 4 | violet | 590 | 80,000 | 0.075 | 6,000 |
| Comparative Example Compound | red | 512 | 34,000 | $1.0 \times 10^{-5}$ or less | 10 or less |

From Table 4, it is known that Example Compounds 1 to 4 have a higher absorbance coefficient ($\epsilon$) and a higher $\epsilon C$ as compared with Comparative Example Compound.

<Preparation of Black Ink>

A composition 1 comprising Example Compound 4 and an yellow compound A, a red compound A and blue compound A shown below was dissolved in n-decane (relative permittivity 2.0, solubility in water 1 mg/L or less, manufactured by Tokyo Chemical Industry) to prepare a black ink as in Table 5. Besides, a composition 2 comprising the yellow compound A, the red compound A and the blue compound A was dissolved in the same n-decan as in the black ink to prepare a comparative ink as in Table 5. In both the black ink and the comparative ink, the amount of each compound was so controlled that the optical density (OD) of the ink through an optical path of 0.010 mm could be 2.7.

TABLE 5

| | Example Compound 4 (g) | Yellow Compound A (g) | Red Compound A (g) | Blue Compound A (g) | Total Weight of Compounds (g) | N-decane (g) |
|---|---|---|---|---|---|---|
| Black Ink | 0.031 | 0.075 | 0.046 | 0.279 | 0.431 | 1.569 |
| Comparative Ink | — | 0.0956 | 0.05 | 0.356 | 0.502 | 1.498 |

<Yellow Compound A>

The compound (1-1) described in WO2009/063880 was used. Its structure is shown below.

[Chem. 31]

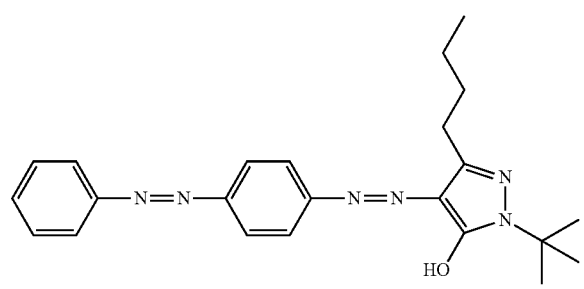

Yellow Compound A

Synthesis of Intermediate H-2

A mixture of m-toluidine (51.1 g, 477 mmol), 1-bromo-2-ethylhexane (357.3 g, 1.86 mol) and potassium carbonate (221.5 g, 1.6 mol) was stirred at 140° C. for 17 hours. After left cooled, this was filtered, and the resultant organic layer was concentrated and then purified through silica gel column chromatography to give an intermediate H-2 (52 g, yield 33%).

[Chem. 32]

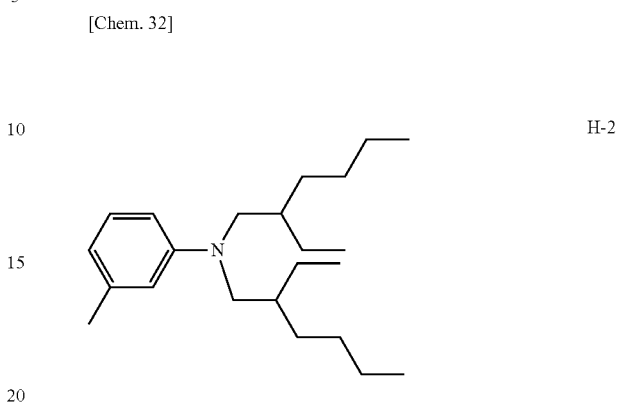

H-2

<Red Compound A>

A compound represented by the following formula H-1 (0.50 g, 3.3 mmol), glacial acetic acid (3 ml), propionic acid (0.7 ml), sulfuric acid (2.7 ml) and desalted water (0.3 ml) was cooled in an ice bath, and 44 wt. % nitrosylsulfuric acid (1.0 g, 3.6 mmol) was dropwise added thereto at an internal system temperature of 1° C. While kept at an internal system temperature of 0±5° C., this was stirred for 1 hour to give a diazo liquid. In a separate chamber, the synthesized intermediate H-2 (0.81 g, 3.1 mmol), tetrahydrofuran (40 ml), sulfamic acid (0.06 g, 0.6 mmol) and sodium acetate (5.7 g) were metered, and while the internal system temperature was kept at 0±5° C. with cooling with ice, the diazo liquid was dropwise added thereto. During the course of addition, ice and tetrahydrofuran (40 ml) were added. After the addition, an aqueous sodium acetate solution was added to make the liquid have a pH of 4. This was extracted with toluene, concentrated under reduced pressure and purified through silica gel column chromatography, and the resultant solid was washed with methanol/water (1/1 by volume) to give a red compound A (0.45 g, yield 32%).

[Chem. 33]

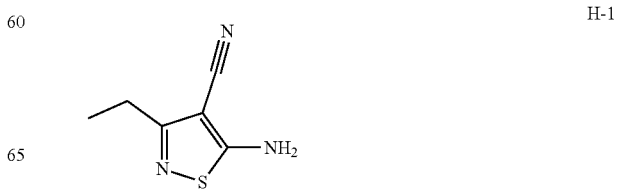

H-1

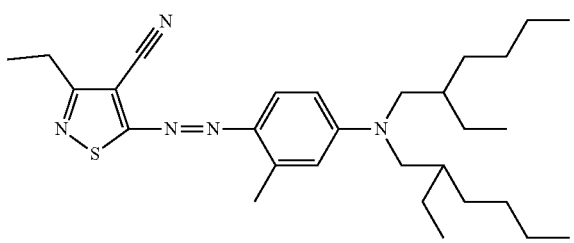

Red Compound A

<Blue Compound A>

The compound described in JP-A 2000-313174 was used. Its structure is shown below.

[Chem. 34]

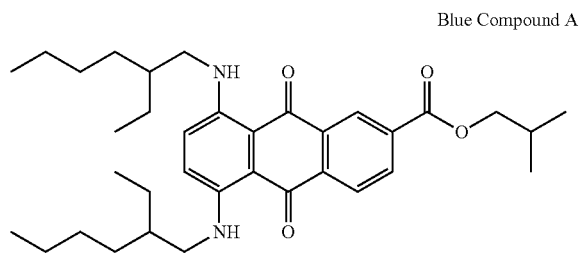

Blue Compound A

Of the yellow compound A, the red compound A and the blue compound A, the absorption maximum wavelength (λmax), the molar absorbance coefficient ε, the solubility C at 5° C., and εC are shown in Table 6. The values were determined in the same manner as that for Example Compound 1.

TABLE 6

| | λmax (nm) | ε (L · mol$^{-1}$ · cm$^{-1}$) | C (mol · L$^{-1}$) | εC (cm$^{-1}$) |
|---|---|---|---|---|
| Yellow Compound A | 417 | 25000 | 0.076 | 1900 |
| Red Compound A | 530 | 4600 | 0.086 | 3900 |
| Blue Compound A | 668 | 19000 | 0.170 | 3200 |

<Hue Evaluation>

Using a cell having a measurement optical length of 0.01 mm, the black ink and the comparative ink were analyzed to measure the spectrum thereof. Using a saturation computation program attached to Hitachi Spectrophotometer U-4100, each ink was analyzed for colorimetry with a light source of D65 and under the condition of a viewing angle of 2 degrees, and the hue thereof was quantitatively evaluated.

The hue evaluation results of the black ink 1 and the comparative ink are shown in Table 7.

<Viscosity Measurement>

Using a rotary viscometer (BROOKFIELD LV-1), the viscosity at 25° C. of the black ink and the comparative ink was measured. The measured results are shown in Table 7.

TABLE 7

| | Measurement Optical Length (mm) | Hue Evaluation Results | | | | | Ink Viscosity (mPa · s) |
|---|---|---|---|---|---|---|---|
| | | L* | a* | B* | C* | OD | |
| Black Ink | 0.01 | 1.78 | 1.11 | −1.33 | 1.70 | 2.7 | 1.62 |
| Comparative Ink | 0.01 | 1.94 | −0.21 | 1.79 | 1.80 | 2.7 | 1.85 |

Though both the black ink and the comparative ink have the same OD, the values L* and C* of the black ink are smaller than those of the comparative ink, and it is known that the black ink has an excellent black hue and is good. In addition, the ink viscosity of the black ink is smaller than that of the comparative ink, and it is known that the black ink has excellent properties.

While the present invention has been described in detail and with reference to specific embodiments thereof, it will be apparent to one skilled in the art that various changes and modifications can be made therein without departing from the spirit and scope thereof.

The present application is based upon a Japanese patent application filed on Aug. 1, 2012 (Patent Application 2012-171276) and a Japanese patent application filed on Nov. 28, 2012 (Patent Application 2012-260018), the contents of which are incorporated herein by reference.

INDUSTRIAL APPLICABILITY

The ink of the present invention is favorably used for displays and optical shutters, and in particular, especially favorably used, for example, for electrowetting displays and electrophoretic displays such as electronic papers, etc.

The invention claimed is:

1. An ink, comprising:
a solvent having a relative permittivity at 22° C. and at a measurement frequency of 1 kHz of 3 or less and having a solubility in water at 25° C. of 20 mg/L or less; and
an azo compound represented by formula (1):

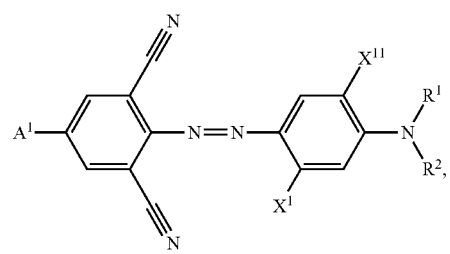

wherein:
$R^1$ and $R^2$ each independently represent a hydrocarbon group optionally having a substituent, wherein at least one of $R^1$ and $R^2$ is a branched alkyl group having from 6 to 20 carbon atoms; and
$X^1$, $X^{11}$ and $A^1$ each independently represent a hydrogen atom or a substituent.

2. The ink of claim 1, wherein the solvent comprises at least one solvent selected from a group consisting of a hydrocarbon solvent, a silicone oil and a fluorocarbon solvent.

3. The ink of claim 1, wherein a product εC of a molar absorbance coefficient ε(L·mol$^{-1}$·cm$^{-1}$) at absorption maximum wavelength of an n-decane solution of the azo compound, and a saturation solubility C (mol·L$^{-1}$) of the solution at 5° C. is 1000 cm$^{-1}$ or more.

4. The ink of claim 1, further comprising:
at least one compound selected from a group consisting of a heterocyclic compound, a cyanovinyl compound and an anthraquinone compound.

5. The ink of claim 4, wherein the heterocyclic compound is at least one compound selected from a group consisting of formulae (2) to (5):

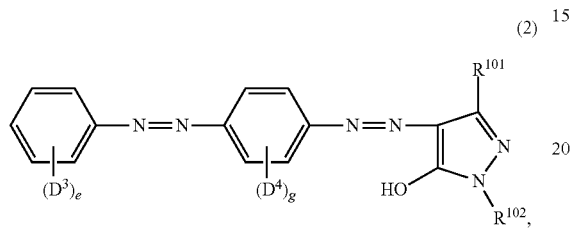

(2)

wherein:
$R^{101}$ and $R^{102}$ each independently represent a hydrogen atom or an arbitrary substituent:
$D^3$ and $D^4$ each independently represent an arbitrary substituent,
e represents an integer of from 0 to 5, and when e is 2 or more, 2 or more $D^3$s existing in one molecule may be the same or different;
g represents an integer of from 0 to 4, and when g is 2 or more, 2 or more $D^4$s existing in one molecule may be the same or different,

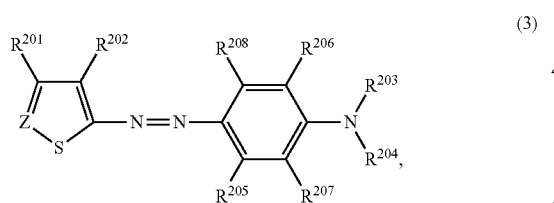

(3)

wherein:
$R^{201}$ to $R^{208}$ each independently represent a hydrogen atom or a substituent;
Z represents a nitrogen atom or a methine group optionally having a substituent,

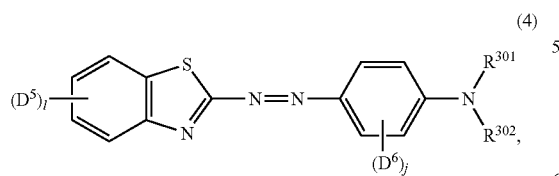

(4)

wherein:
$R^{301}$, $R^{302}$, $D^5$ and $D^6$ each independently represent a substituent;
l represents an integer of from 0 to 4, and when l is 2 or more, 2 or more $D^5$s existing in one molecule may be the same or different;
j represents an integer of from 0 to 4, and when j is 2 or more, 2 or more $D^6$s existing in one molecule may be the same or different, and

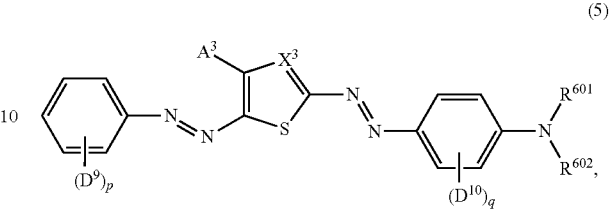

(5)

wherein:
$R^{601}$, $R^{602}$, $D^9$ and $D^{10}$ each independently represent a substituent;
$A^3$ represents a hydrogen atom or a substituent;
p represents an integer of from 0 to 5, and when p is 2 or more, 2 or more $D^9$s existing in one molecule may be the same or different;
q represents an integer of from 0 to 4, and when q is 2 or more, 2 or more $D^{10}$s existing in one molecule may be the same or different;
$X^3$ represents a nitrogen atom, or a methine group having a halogen atom, a cyano group or a group —COOR$^{605}$ as a substituent;
$R^{605}$ represents a hydrogen atom, an alkyl group having a carbon number of from 1 to 20 and optionally having a substituent, an aryl group having a carbon number of from 6 to 20 and optionally having a substituent, or a heteroaryl group having a carbon number of from 2 to 20 and optionally having a substituent.

6. The ink of claim 4, comprising an anthraquinone compound represented by formula (7):

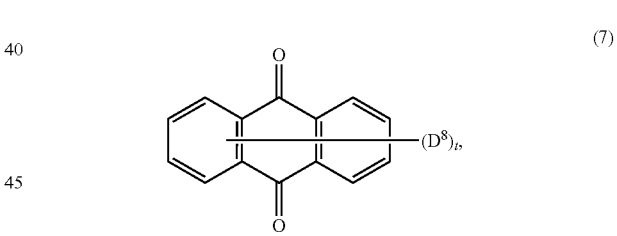

(7)

wherein:
$D^8$ represents a substituent;
t represents an integer of from 0 to 8, and when t is 2 or more, 2 or more $D^8$s existing in one molecule may be the same or different.

7. The ink of claim 1, which is adapted to function in displays or optical shutters.

8. A display, comprising a display area comprising the ink of claim 1, and which displays an image by controlling a voltage application to the display area.

9. The display of claim 8, wherein the display area further comprises at least either one of electrophoretic particles and an aqueous medium.

10. The display of claim 8, which displays an image by changing the coloration state through control of voltage application.

11. The display of claim 8, which displays an image according to an electrowetting system or an electrophoretic system.

12. An electronic paper, comprising the display of claim 8.

13. An azo compound represented by formula (8):

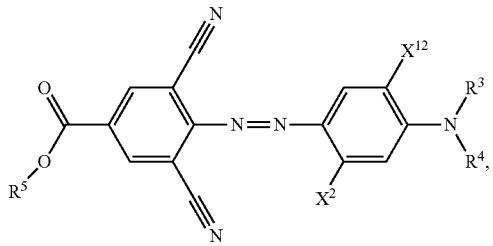

(8)

wherein:
$R^3$ and $R^4$ each independently represent an alkyl group having a carbon number of from 1 to 20 and optionally having a substituent, wherein at least one of $R^3$ and $R^4$ is a branched alkyl group having from 6 to 20 carbon atoms;

$R^5$ represents an alkyl group having a branched chain and having a carbon number of from 4 to 20 and optionally having a substituent;

$X^2$ and $X^{12}$ each independently represent a hydrogen atom or a substituent.

14. The ink of claim 1, wherein $R^1$ and $R^2$ are each independently a branched alkyl group having from 6 to 20 carbon atoms, $X^{11}$ is hydrogen, and $X^1$ is an acylamino group having from 1 to 20 carbon atoms and optionally having a branched chain and a cyclic structure.

15. The azo compound of claim 13, wherein $R^3$ and $R^4$ are each independently a branched alkyl group having from 6 to 20 carbon atoms, $X^{12}$ is hydrogen, and $X^2$ is an acylamino group having from 1 to 20 carbon atoms and optionally having a branched chain and a cyclic structure.

* * * * *